US007955802B2

(12) United States Patent
Whitman et al.

(10) Patent No.: US 7,955,802 B2
(45) Date of Patent: Jun. 7, 2011

(54) SYSTEMS AND METHODS FOR MULTIPLEX ANALYSIS OF PCR IN REAL TIME

(75) Inventors: Douglas F. Whitman, Round Rock, TX (US); Charles J. Collins, Austin, TX (US)

(73) Assignee: Luminex Corporation, Austin, TX (US)

( * ) Notice: Subject to any disclaimer, the term of this patent is extended or adjusted under 35 U.S.C. 154(b) by 271 days.

(21) Appl. No.: 11/956,257

(22) Filed: Dec. 13, 2007

(65) Prior Publication Data

US 2008/0305481 A1    Dec. 11, 2008

Related U.S. Application Data

(60) Provisional application No. 60/869,742, filed on Dec. 13, 2006.

(51) Int. Cl.
*C12Q 1/68* (2006.01)
*C12P 19/34* (2006.01)

(52) U.S. Cl. ........................................ 435/6; 435/91.2
(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,942,124 A | 7/1990 | Church | 435/6 |
| 4,965,188 A | 10/1990 | Mullis et al. | 435/6 |
| 4,996,143 A | 2/1991 | Heller et al. | 435/6 |
| 5,038,852 A | 8/1991 | Johnson et al. | 165/12 |
| 5,210,015 A | 5/1993 | Gelfand et al. | 435/6 |
| 5,219,727 A | 6/1993 | Wang et al. | 435/6 |
| 5,333,675 A | 8/1994 | Mullis et al. | 165/12 |
| 5,432,272 A | 7/1995 | Benner | 536/25.3 |
| 5,436,134 A | 7/1995 | Haugland et al. | 435/34 |
| 5,475,610 A | 12/1995 | Atwood et al. | 364/500 |
| 5,476,774 A | 12/1995 | Wang et al. | 435/91.2 |
| 5,487,972 A | 1/1996 | Gelfand et al. | 435/6 |
| 5,525,494 A | 6/1996 | Newton | 435/91.2 |
| 5,532,129 A | 7/1996 | Heller | 435/6 |
| 5,538,848 A | 7/1996 | Livak et al. | 435/5 |
| 5,565,322 A | 10/1996 | Heller | 435/6 |
| 5,654,413 A | 8/1997 | Brenner | 536/22.1 |
| 5,656,493 A | 8/1997 | Mullis et al. | 435/286.1 |
| 5,658,751 A | 8/1997 | Yue et al. | 435/34 |
| 5,665,539 A | 9/1997 | Sano et al. | 435/6 |
| 5,716,784 A | 2/1998 | Di Cesare | 435/6 |
| 5,723,591 A | 3/1998 | Livak et al. | 536/22.1 |
| 5,736,330 A | 4/1998 | Fulton | 435/6 |
| 5,804,375 A | 9/1998 | Gelfand et al. | 435/6 |
| 5,866,336 A | 2/1999 | Nazarenko et al. | 435/6 |
| 5,871,908 A | 2/1999 | Henco et al. | 435/6 |
| 5,925,517 A | 7/1999 | Tyagi et al. | 435/6 |
| 5,981,180 A | 11/1999 | Chandler et al. | 435/6 |
| 5,994,056 A | 11/1999 | Higuchi | 435/6 |
| 6,030,787 A | 2/2000 | Livak et al. | 435/6 |
| 6,046,807 A | 4/2000 | Chandler | 356/318 |
| 6,057,107 A | 5/2000 | Fulton | 435/6 |
| 6,103,463 A | 8/2000 | Chetverin | 435/6 |
| 6,139,800 A | 10/2000 | Chandler | 422/82.08 |
| 6,140,054 A | 10/2000 | Wittwer | 435/6 |
| 6,140,496 A | 10/2000 | Benner | 536/27.1 |
| 6,171,785 B1 | 1/2001 | Higuchi | 435/6 |
| 6,174,670 B1 | 1/2001 | Wittwer et al. | 435/6 |
| 6,232,079 B1 | 5/2001 | Wittwer et al. | 435/6 |
| 6,258,569 B1 | 7/2001 | Livak et al. | 435/91.1 |
| 6,268,222 B1 | 7/2001 | Chandler et al. | 436/523 |
| 6,270,967 B1 | 8/2001 | Whitcombe et al. | 435/6 |
| 6,303,305 B1 | 10/2001 | Wittwer et al. | 435/6 |
| 6,322,971 B1 | 11/2001 | Chetverin et al. | 435/6 |
| 6,326,145 B1 | 12/2001 | Whitcombe et al. | 435/6 |
| 6,366,354 B1 | 4/2002 | Chandler | 356/318 |
| 6,410,235 B1 | 6/2002 | Weindel et al. | 435/6 |
| 6,411,904 B1 | 6/2002 | Chandler | 702/21 |
| 6,449,562 B1 | 9/2002 | Chandler et al. | 702/19 |
| 6,503,720 B2 | 1/2003 | Wittwer et al. | 435/6 |
| 6,514,295 B1 | 2/2003 | Chandler et al. | 8/607 |
| 6,524,793 B1 | 2/2003 | Chandler et al. | 435/6 |
| 6,528,165 B2 | 3/2003 | Chandler | 428/402.2 |
| 6,569,627 B2 | 5/2003 | Wittwer et al. | 435/6 |
| 6,592,822 B1 | 7/2003 | Chandler | 422/82.05 |
| 6,617,106 B1 | 9/2003 | Benner | 435/6 |
| 6,635,427 B2 | 10/2003 | Wittwer et al. | 435/6 |
| 6,703,236 B2 | 3/2004 | Atwood | 435/286.1 |
| 6,790,623 B2 | 9/2004 | Weindel et al. | 435/6 |

(Continued)

FOREIGN PATENT DOCUMENTS

WO    WO 93/17126    9/1993

(Continued)

OTHER PUBLICATIONS

Bengtsson et al., "A new minor groove binding asymmetric cyanine reporter dye for real-time PCR," *Nucleic Acids Res.*, 31:e45, 2003.
Bernard et al., "Homogeneous multiplex genotyping of hemochromatosis mutations with fluorescent hybridization probes," *Am. J. Pathol.*, 153:1055-1061, 1998.
Bernard et al., "Integrated amplification and detection of the C677T point mutation in the methylenetetrahydrofolate reductase gene by fluorescence resonance energy transfer and probe melting curves," *Anal. Biochem.*, 255:101-107, 1998.
Bortolin et al., "Analytical validation of the tag-it high-throughput microsphere-based universal array genotyping platform: application to the multiplex detection of a panel of thrombophilia-associated single-nucleotide polymorphisms," *Clin. Chem.*, 50:2028-2036, 2004.
Bustin et al., "Pitfalls of quantitative real-time reverse-transcription polymerase chain reaction," *J. Biomol. Tech.*, 15:155-166, 2004.

(Continued)

*Primary Examiner* — Kenneth R. Horlick
*Assistant Examiner* — David C Thomas
(74) *Attorney, Agent, or Firm* — Fulbright & Jaworski LLP

(57) ABSTRACT

The present invention provides methods and systems for real-time measurements of PCR with multiplexing capability. Certain embodiments relate to methods and systems that use fluorescently encoded superparamagnetic microspheres for the immobilization of amplification products during the PCR process, and an imaging chamber of a measurement device that is also capable of controllable thermal cycling for assisting the PCR process.

37 Claims, 14 Drawing Sheets

U.S. PATENT DOCUMENTS

| | | | |
|---|---|---|---|
| 6,814,934 B1 | 11/2004 | Higuchi | 422/82.08 |
| 6,818,437 B1 | 11/2004 | Gambini et al. | 435/288.7 |
| 6,939,720 B2 | 9/2005 | Chandler et al. | 436/518 |
| 7,157,228 B2 | 1/2007 | Hashmi et al. | 435/6 |
| 7,205,105 B2 | 4/2007 | Afonina et al. | 435/6 |
| 7,226,737 B2 | 6/2007 | Pancoska et al. | 435/6 |
| 7,235,406 B1 | 6/2007 | Woudenberg et al. | 436/518 |
| 7,238,321 B2 | 7/2007 | Wittwer et al. | 422/50 |
| 7,288,997 B2 | 10/2007 | Chen | 331/16 |
| 7,387,887 B2 | 6/2008 | Wittwer et al. | 435/91.2 |
| 2004/0175704 A1* | 9/2004 | Sorge et al. | 435/6 |
| 2005/0164219 A1 | 7/2005 | Whitcombe et al. | 435/6 |
| 2005/0191625 A1 | 9/2005 | Kobler et al. | 435/6 |
| 2005/0244850 A1 | 11/2005 | Huang | 435/6 |
| 2006/0019253 A1 | 1/2006 | Wittwer et al. | 435/6 |
| 2006/0051789 A1* | 3/2006 | Kazakov et al. | 435/6 |
| 2006/0105395 A1 | 5/2006 | Pempsell | 435/29 |
| 2006/0211028 A1 | 9/2006 | Mao et al. | 435/6 |
| 2007/0020672 A1 | 1/2007 | Wittwer et al. | 435/6 |
| 2007/0064990 A1 | 3/2007 | Roth | 382/100 |

FOREIGN PATENT DOCUMENTS

| | | |
|---|---|---|
| WO | WO 97/31256 | 8/1997 |
| WO | WO 2006/028987 | 3/2006 |

OTHER PUBLICATIONS

Bustin, "Quantification of mRNA using real-time reverse transcription PCR (RT-PCR): trends and problems," *J. Mol. Endocrinol.*, 29(1):23-39, 2002.

Cardullo et al., "Detection of nucleic acid hybridization by nonradiative fluorescence resonance energy transfer," *Proc. Natl. Acad. Sci. USA*, 85:8790-8804, 1988.

Chen et al., "Development of a novel real-time RT-PCR assay with LUX primer for the detection of swine transmissible gastroenteritis virus," *J. Virol. Methods*, 122(1):57-61, 2004.

Espy et al., "Real-time PCR in clinical microbiology: applications for routine laboratory testing," *Clin. Microbiol. Rev.*, 19(1):165-256, 2006.

Flagella et al., "A multiplex branched DNA assay for parallel quantitative gene expression profiling," *Anal. Biochem.*, 352:50-60, 2006.

Guo et al., "Enhanced discrimination of single nucleotide polymorphisms by artificial mismatch hybridization," *Nat. Biotechnol.*, 4:331-335, 1997.

International Search Report and Written Opinion issued in International Application No. PCT/US2007/087492, mailed Jun. 27, 2008.

Ishiguro et al., "Homogeneous quantitative assay of hepatitis C virus RNA by polymerase chain reaction in the presence of a fluorescent intercalater," *Anal. Biochemistry*, 229(2): 207-213, 1995.

Johnson et al., "A third base pair for the polymerase chain reaction: inserting isoC and isoG," *Nucl. Acids Res.*, 32:1937-1941, 2004.

Lay and Wittwer, "Real-time fluorescence genotyping of factor V Leiden during rapid-cycle PCR," *Clin. Chem.*, 43:2262-2267, 1997.

Marras et al., "Real-time assays with molecular beacons and other fluorescent nucleic acid hybridization probes," *Clinica Chimica Acta*, 363:48-60, 2006.

Morrison et al., "Sensitive fluorescence-based thermodynamic and kinetic measurements of DNA hybridization in solution," *Biochemistry*, 32:3095-3104, 1993.

Morrison et al., "Solution-phase detection of polynucleotides using interacting fluorescent labels and competitive hybridization," *Anal. Biochem.*, 183:231-244, 1989.

Moser et al., "Enzymatic repair of an expanded genetic information system," *Nucl. Acids Res.*, 31:5048-5053, 2003.

Moser et al., "Microsphere sedimentation arrays for multiplexed bioanalytics," *Analytica Chicica Acta*, 558:102-109, 2006.

Nazarenko et al., "A closed tube format for amplification and detection of DNA based on energy transfer," *Nucleic Acids Res.*, 25(12):2516-2521, 1997.

Nazarenko et al., "Multiplex quantitative PCR using self-quenched primers labeled with a single fluorophore," *Nucleic Acids Res.*, 30(9):e37, 2002.

Peyret et al., "Nearest-neighbor thermodynamics and NMR of DNA sequences with internal A.A, C.C, G.G, and T.T mismatches," *Biochemistry*, 38:3468-3477, 1999.

Sims et al., "Immunopolymerase chain reaction using real-time polymerase chain reaction for detection," *Anal Biochem.* 281:230-232, 2000.

Straub et al., "Automated methods for multiplexed pathogen detection," *J. Microbiol. Methods*, 62:303-316, 2005.

U.S. Appl. No. 60/984,982, entitled "One-Step Target Detection Assay," by Barbara Galvan-Goldman et al., filed Nov. 2, 2007.

Whitcombe et al., "Detection of PCR products using self-probing amplicons and fluorescence," *Nat. Biotechnol.*, 17:804-807, 1999.

Wilson et al., "A multiplexed PCR-coupled liquid bead array for the simultaneous detection of four biothreat agents," *Mol. Cell Probes*, 19:137-144, 2005.

Zipper et al., "Investigations on DNA intercalation and surface binding by SYBR Green I, its structure determination and methodological implications," *Nucleic Acids Res.*, 32(12):e103, 2004.

* cited by examiner

The Factor V Leiden genomic gene sequence:
Factor V Leiden (FVL)          [gi:2769646 and gi:488109]

```
         v         v         V         v         v         v         v
CACAGAAAATGATGCCCAGTGCTTAACAAGACCATACTACAGTGACGTGGACATCATGAGAGACATCGCC    70
GTGTCTTTTACTACGGGTCACGAATTGTTCTGGTATGATGTCACTGCACCTGTAGTACTCTCTGTAGCGG
         v         v         v         v         v         v         v
TCTGGGCTAATAGGACTACTTCTAATCTGTAAGAGCAGATCCCTGGACAGGC[G]AGGAATACAGGTATTTT   140
AGACCCGATTATCCTGATGAAGATTAGACATTCTCGTCTAGGGACCTGTCCG[C]TCCTTATGTCCATAAAA
         v         v         v         v         v         v         v
GTCCTTGAAGTAACCTTTCAGAAATTCTGAGAATTTCTTCTGGCTAGAACATGTTAGGTCTCCTGGCTAA   210
CAGGAACTTCATTGGAAAGTCTTTAAGACTCTTAAAGAAGACCGATCTTGTACAATCCAGAGGACCGATT
         v         v         v         v         v         v         v
ATAATGGGGCATTTCCTTCAAGAGAACAGTAATTGTCAAGTAGTCCTTTTTAGCACCAGTGTGATAACAT   280
TATTACCCCGTAAAGGAAGTTCTCTTGTCATTAACAGTTCATCAGGAAAAATCGTGGTCACACTATTGTA
         v         v
TTATTCTTTTTTTTTTTTG  (SEQ ID NO. 6)      300
AATAAGAAAAAAAAAAAAC  (SEQ ID NO. 7)
```

FIG. 13

CFTR EXON 20
CAGCTTTTTTGAGACTACTGAACACTGAAGGAGAAATCCAGATCGATGGTGTGTCTTGGGATT
CAATAACTTTGCAACAGTG[G]AGGAAAGCCTTTGGAGTGATACCACAGGTGAGCAAAAGGACT
TAGCCAGAAAAAAGGCAACT (SEQ ID NO: 8)
CFTR INTRON 10
TCAAATTCAGATTGAGCATACTAAAAGTGACTCTCTAATTTTCTATTTTTGGTAATAGGACATC
TCCAAGTTTGCAGAGAAAGACAATATAGTTCTTGGAGAAGGTGGAATCAC (SEQ ID NO: 9)
CFTR EXON 11
ATCTCCAAGTTTGCAGAGAAAGACAATATAGTTCTTGGAGAAGGTGGAATCACACTGAGTGG
AGGTCAACGAGCAAGAATTTCTTTAGCAAGGTGAATAACTAATTATTGGTCTAGCAAGCATTT
GCTGTAAATGTCATTCATGTAAAA (SEQ ID NO: 10)
CFTR EXON 4
TCCCCTTTTGTAGGAAGTCACCAAAGCAGTACAGCCTCTCTTACTGGGAAGAATCATAGCTTC
CTATGACCCGGATAACAAGGAGGAACGCTCTATCGCGATTTATCTAGGCATAGGCTTATGCCT
TCTCTTTATTGTGAGGACACTGCTCCTACACCCA (SEQ ID NO: 11)
CFTR EXON 21
TTTTTTGCTATAGAAAGTATTTATTTTTTCTGGAACATTTAGAAAAAACTTGGATCCCTATGAA
CAGTGGAGTGATCAAGAAATATGGAAAGTTGCAGATGAGGTAAGGCTGCTAACT (SEQ ID NO: 12)
CFTR EXON 7
TTTTATAGAACAGAACTGAAACTGACTCGGAAGGCAGCCTATGTGAGATACTTCAATAGCTCA
GCCTTCTTCTTCTCAGGGTTCTTTGTGGTGTTTTTATCTGTGCTTCCCTATGCACTAATCAAAGG
AATCATCCTCCGGAAAATATTCACCACCATCTCATTC (SEQ ID NO: 13)
CHROMOSOME 7q31.2
AATTTCAGTTGACTTGTCATCTTGATTTCTGGAGACCACAAGGTAATGAAAAATAATTACAAG
AGTCTTCCATCTGTTGCAGTATTAAAATGGCGAGTAAGACACCCTGAAAGGAAATGTTCTATT
CATGGTACAATGCAATTACAGCTAGCACCAAATTCAACACTGT (SEQ ID NO: 14)
CFTR EXON 9
TAATTTCTCACTTCTTGGTACTCCTGTCCTGAAAGATATTAATTTCAAGATAGAAAGAGGACA
GTTGTTGGCGGTTGCTGGATCCACTGGAGCAGGCAAGGTAGTTCTTTTGTTCTTCACTAT (SEQ ID NO: 15)

FIG. 15

SYSTEMS AND METHODS FOR MULTIPLEX ANALYSIS OF PCR IN REAL TIME

This application claims priority to U.S. provisional patent application 60/869,742, filed Dec. 13, 2006, the entire disclosure of which is incorporated by reference.

BACKGROUND OF THE INVENTION

1. Field of the Invention

This invention generally relates to systems and methods for performing measurements of DNA amplification such as PCR. In particular, this invention relates to "real time" measurements of PCR with multiplexing capability. Certain embodiments relate to a system which uses particles, such as paramagnetic microspheres, and an imaging chamber of a measurement device which is also capable of controllable thermal cycling for assisting the PCR process.

2. Description of Related Art

Polymerase chain reaction (PCR) is a molecular biology technique for enzymatically replicating DNA without using a living organism. PCR is commonly used in medical and biological research labs for a variety of tasks, such as the detection of hereditary diseases, the identification of genetic fingerprints, the diagnosis of infectious diseases, the cloning of genes, paternity testing, and DNA computing. PCR has been accepted by molecular biologists as the method of choice for nucleic acid detection because of its unparalleled amplification and precision capability. DNA detection is typically performed at the end-point, or plateau phase of the PCR reaction, making it difficult to quantify the starting template. Real-time PCR or kinetic PCR advances the capability of end-point PCR analysis by recording the amplicon concentration as the reaction progresses. Amplicon concentration is most often recorded via a fluorescent signal change associated with the amplified target. Real-time PCR is also advantageous over end-point detection in that contamination is limited because it can be performed in a closed system. Other advantages include greater sensitivity, dynamic range, speed, and fewer processes required.

Several assay chemistries have been used in real-time PCR detection methods. These assay chemistries include using double-stranded DNA binding dyes, dual-labeled oligonucleotides, such as hairpin primers, and hairpin probes. Other chemistries include exonuclease based probes such as hydrolysis probes. Various PCR and real-time PCR methods are disclosed in U.S. Pat. Nos. 5,656,493; 5,994,056; 6,174,670; 5,716,784; 6,030,787; and 6,174,670, which are incorporated herein by reference.

A drawback of current real-time PCR is its limited multiplexing capability. Current real-time PCR technologies use reporter fluorochromes that are free in solution. This design necessitates the use of spectrally distinct fluorochromes for each assay within a multiplex reaction. For example, a multiplex reaction designed to detect 4 target sequences would require an instrument capable of distinguishing 4 different free floating fluorochromes by spectral differentiation, not including controls. These requirements not only limit the practical multiplexing capability, but also increase costs since such instruments typically require multiple lasers and filters. Current real-time PCR technologies have multiplexing capabilities from about 1-6 plex.

SUMMARY OF THE INVENTION

The present invention relates to systems and methods for amplification and detection of DNA. In particular, the present invention provides systems and methods that greatly increase multiplexing capabilities of real-time PCR. In one embodiment, the present invention provides a method of amplifying and detecting a plurality of nucleic acid targets in a sample comprising: (a) combining in a chamber a sample comprising the plurality of nucleic acid targets, a plurality of primer pairs for priming amplification of the plurality of nucleic acid targets, a labeling agent, and a plurality of probes complementary to the plurality of nucleic acid targets, wherein the probes are immobilized on a plurality of encoded particles such that the identity of each probe is known from the encoded particle on which it is immobilized; (b) performing an amplification cycle to form amplification products for each of the plurality of nucleic acid targets amplified with the plurality of primer pairs; (c) hybridizing the amplification products to the probes immobilized on the encoded particles; (d) attracting the encoded particles and the amplification products hybridized to the probes immobilized on the encoded particles to the surface of the chamber; (e) detecting a signal from the encoded particles and detecting a signal directly (e.g., a label incorporated into the amplification product) or indirectly (e.g., a labeled complementary nucleic acid sequence hybridized to the amplification product) from the amplification products; (f) dispersing the encoded particles and the amplification products hybridized to the probes immobilized on the encoded particles from the surface of the chamber prior to performing a further amplification cycle; and (g) repeating steps (b) through (f) at least once; wherein the plurality of nucleic acid targets in the sample are amplified and detected. In certain aspects of the invention, steps (b) through (f) are repeated between 10 to 40 times.

The particles may be particles with magnetic properties and/or particles with a density that allows them to rest upon a two dimensional surface in solution. The particles may in one way or another rest upon a two dimensional surface by magnetic, gravitational, or ionic forces, or by chemical bonding, or by any other means known to those skilled in the art. Particles may consist of glass, polystyrene, latex, metal, quantum dot, polymers, silica, metal oxides, ceramics, or any other substance suitable for binding to nucleic acids, or chemicals or proteins which can then attach to nucleic acids. The particles may be rod shaped or spherical or disc shaped, or comprise any other shape. The particles may also be distinguishable by their shape or size or physical location. The particles may be spectrally distinct by virtue of having a composition containing dyes or ratios or concentrations of one or more dyes or fluorochromes, or may be distinguishable by barcode or holographic images or other imprinted forms of particle coding. Where the particles are magnetic particles, they may be attracted to the surface of the chamber by application of a magnetic field. Likewise, magnetic particles may be dispersed from the surface of the chamber by removal of the magnetic field. The magnetic particles are preferably paramagnetic or superparamagnetic. Paramagnetic and superparamagnetic particles have negligible magnetism in the absence of a magnetic field, but application of a magnetic field induces alignment of the magnetic domains in the particles, resulting in attraction of the particles to the field source. When the field is removed, the magnetic domains return to a random orientation so there is no interparticle magnetic attraction or repulsion. In the case of superparamagnetism, this return to random orientation of the domains is nearly instantaneous, while paramagnetic materials will retain domain alignment for some period of time after removal of the magnetic field. Where the particles have a sufficient density they may be attracted to the bottom surface of the chamber by gravity, and dispersed from the bottom surface of the chamber by agitation of the chamber, such as by vortexing, sonication, or fluidic movement. Agitation of the chamber may also be used to further assist in dispersing particles in methods and systems in which the particles were attracted to a surface of the chamber by other forces, such as magnetic or ionic forces, or suction forces, or vacuum filtration, or affinity, or hydrophilicity or hydrophobicity, or any combination thereof.

In one embodiment, the present invention provides a method of amplifying and detecting a plurality of nucleic acid targets in a sample comprising: (a) combining in a chamber a sample comprising the plurality of nucleic acid targets, a plurality of primer pairs for priming amplification of the plurality of nucleic acid targets, a labeling agent, and a plurality of probes complementary to the plurality of nucleic acid targets, wherein the probes are immobilized on a plurality of encoded magnetic beads such that the identity of each probe is known from the encoded magnetic bead on which it is immobilized; (b) performing an amplification cycle to form labeled amplification products for each of the plurality of nucleic acid targets amplified with the plurality of primer pairs; (c) hybridizing the labeled amplification products to the probes immobilized on the encoded magnetic beads; (d) applying a magnetic field to a surface of the chamber to draw the encoded magnetic beads and the labeled amplification products hybridized to the probes immobilized on the encoded magnetic beads to the surface of the chamber; (e) detecting the encoded magnetic beads and the labeled amplification products; (f) removing the magnetic field from the surface of the chamber prior to performing a further amplification cycle; and (g) repeating steps (b) through (f) at least once; wherein the plurality of nucleic acid targets in the sample are amplified and detected. In certain aspects of the invention, steps (b) through (f) are repeated between 10 to 40 times.

A labeling agent, which may also be referred to as a reporter, is a molecule that facilitates the detection of a molecule (e.g., a nucleic acid sequence) to which it is attached. Numerous reporter molecules that may be used to label nucleic acids are known. Direct reporter molecules include fluorophores, chromophores, and radiophores. Non-limiting examples of fluorophores include, a red fluorescent squarine dye such as 2,4-Bis[1,3,3-trimethyl-2-indolinylidenemethyl] cyclobutenediylium-1,3-dioxolate, an infrared dye such as 2,4 Bis[3,3-dimethyl-2-(1H-benz[e]indolinylidenemethyl)] cyclobutenediylium-1,3-dioxolate, or an orange fluorescent squarine dye such as 2,4-Bis[3,5-dimethyl-2-pyrrolyl]cyclobutenediylium-1,3-diololate. Additional non-limiting examples of fluorophores include quantum dots, Alexa Fluor® dyes, AMCA, BODIPY® 630/650, BODIPY® 650/665, BODIPY®-FL, BODIPY®-R6G, BODIPY®-TMR, BODIPY®-TRX, Cascade Blue®, CyDye™, including but not limited to Cy2™, Cy3™, and Cy5™, a DNA intercalating dye, 6-FAM™, Fluorescein, HEX™, 6-JOE, Oregon Green® 488, Oregon Green® 500, Oregon Green® 514, Pacific Blue™, REG, phycobilliproteins including, but not limited to, phycoerythrin and allophycocyanin, Rhodamine Green™, Rhodamine Red™, ROX™, TAMRA™, TET™, Tetramethylrhodamine, or Texas Red®. A signal amplification reagent, such as tyramide (PerkinElmer), may be used to enhance the fluorescence signal. Indirect reporter molecules include biotin, which must be bound to another molecule such as streptavidin-phycoerythrin for detection. Pairs of labels, such as fluorescence resonance energy transfer pairs or dye-quencher pairs, may also be employed.

Labeled amplification products may be labeled directly or indirectly. Direct labeling may be achieved by, for example, using labeled primers, using labeled dNTPs, using labeled nucleic acid intercalating agents, or combinations of the above. Indirect labeling may be achieved by, for example, hybridizing a labeled probe to the amplification product.

Encoded particles, such as encoded magnetic beads, may be encoded with fluorescent dyes. Encoding with fluorescent dyes may employ fluorescent dyes with different fluorescent emission wavelengths and/or different fluorescent intensities.

In another embodiment, the present invention provides a method of amplifying and detecting a plurality of nucleic acid targets in a sample comprising: (a) combining in a chamber a sample comprising the plurality of nucleic acid targets, a plurality of primer pairs for priming amplification of the plurality of nucleic acid targets, wherein one primer of each primer pair is labeled, and a plurality of probes complementary to the plurality of nucleic acid targets, wherein the probes are immobilized on a plurality of encoded magnetic beads such that the identity of each probe is known from the encoded magnetic bead on which it is immobilized; (b) performing an amplification cycle to form labeled amplification products for each of the plurality of nucleic acid targets amplified with the plurality of primer pairs; (c) hybridizing the labeled amplification products to the probes immobilized on the encoded magnetic beads; (d) applying a magnetic field to a surface of the chamber to draw the encoded magnetic beads and the labeled amplification products hybridized to the probes immobilized on the encoded magnetic beads to the surface of the chamber; (e) detecting the encoded magnetic beads and the labeled amplification products; (f) removing the magnetic field from the surface of the chamber prior to performing a further amplification cycle; and (g) repeating steps (b) through (f) at least once; wherein the plurality of nucleic acid targets in the sample are amplified and detected. In certain aspects of the invention, steps (b) through (f) are repeated between 10 to 40 times.

In yet another embodiment, the present invention provides a method of amplifying and detecting a plurality of nucleic acid targets in a sample comprising: (a) combining in a chamber a sample comprising the plurality of nucleic acid targets, a plurality of primer pairs for priming amplification of the plurality of nucleic acid targets, and a plurality of molecular beacons complementary to the plurality of nucleic acid targets, wherein the molecular beacons are immobilized on a plurality of encoded magnetic beads such that the identity of each molecular beacon is known from the encoded magnetic bead on which it is immobilized; (b) performing an amplification cycle to form amplification products for each of the plurality of nucleic acid targets amplified with the plurality of primer pairs; (c) hybridizing the amplification products to the molecular beacons immobilized on the encoded magnetic beads; (d) applying a magnetic field to a surface of the chamber to draw the encoded magnetic beads and the amplification products hybridized to the molecular beacons immobilized on the encoded magnetic beads to the surface of the chamber; (e) detecting a signal from the encoded magnetic beads and a signal from the molecular beacons; (f) removing the magnetic field from the surface of the chamber prior to performing a further amplification cycle; and (g) repeating steps (b) through (f) at least once; wherein the plurality of nucleic acid targets in the sample are amplified and detected. In certain aspects of the invention, steps (b) through (f) are repeated between 10 to 40 times.

In one embodiment, the present invention provides a method of amplifying and detecting a plurality of nucleic acid targets in a sample comprising: (a) combining in a chamber a sample comprising the plurality of nucleic acid targets, a plurality of primer pairs for priming amplification of the plurality of nucleic acid targets, and a plurality of probe sets complementary to the plurality of nucleic acid targets, wherein each probe set comprises a first probe labeled with a first member of a fluorescent energy transfer pair and immobilized on an encoded magnetic bead such that the identity of the first probe is known from the encoded magnetic bead on which it is immobilized, and a second probe with a second member of the fluorescent energy transfer pair; (b) performing an amplification cycle to form amplification products for each of the plurality of nucleic acid targets amplified with the plurality of primer pairs; (c) hybridizing the amplification products to the probe sets; (d) applying a magnetic field to a surface of the chamber to draw the encoded magnetic beads and the amplification products hybridized to the probes immobilized on the encoded magnetic beads to the surface of the chamber; (e) detecting a signal from the encoded magnetic beads and a signal from the fluorescent energy transfer pair hybridized to the amplification products; (f) removing the magnetic field from the surface of the chamber prior to performing a further amplification cycle; and (g) repeating steps (b) through (f) at least once; wherein the plurality of nucleic acid targets in the sample are amplified and detected. In certain aspects of the invention, steps (b) through (f) are repeated between 10 to 40 times. In certain aspects, the signal from the fluorescent energy transfer pair is an increase in fluorescence. In other aspects, the signal from the fluorescent energy transfer pair is a decrease in fluorescence.

In another embodiment, the present invention provides a method of amplifying and detecting a nucleic acid target in a sample comprising: (a) combining in a chamber a sample comprising the nucleic acid target, a primer pair for priming amplification of the nucleic acid target, and a probe set complementary to the nucleic acid target, wherein the probe set comprises a first probe immobilized on a magnetic bead, and a second probe comprising a label; (b) performing an amplification cycle to form amplification products for the nucleic acid target amplified with the primer pair; (c) hybridizing the amplification products to the probe set; (d) applying a magnetic field to a surface of the chamber to draw the magnetic bead and the amplification products hybridized to the probe immobilized on the encoded magnetic bead to the surface of the chamber; (e) detecting a signal from the second probe hybridized to the amplification products; (f) removing the magnetic field from the surface of the chamber prior to performing a further amplification cycle; and (g) repeating steps (b) through (f) at least once; wherein the nucleic acid target in the sample is amplified and detected. This method may be performed as a single-plex or multi-plex. Multi-plexing may be achieved by using different labels on the second probes and/or by labeling or encoding the particles on which the first probes are immobilized.

In another embodiment, the present invention provides a method of amplifying and detecting a nucleic acid target in a sample comprising: (a) combining in a chamber a sample comprising the nucleic acid target, a primer pair for priming amplification of the nucleic acid target, a dNTP coupled to a quencher molecule, and a fluorescently labeled probe complementary to the nucleic acid target, wherein the probe is immobilized on a magnetic beads; (b) performing an amplification cycle to form amplification products of the nucleic acid target, the amplification products comprising quencher molecules; (c) hybridizing the amplification products to the probe immobilized on the magnetic bead; (d) applying a magnetic field to a surface of the chamber to draw the magnetic bead and the amplification products hybridized to the probe immobilized on the encoded magnetic bead to the surface of the chamber; (e) detecting a signal from the labeled probe, wherein a decrease in the signal from the labeled probe indicates hybridization of the labeled probe to the amplification products comprising quencher molecules; (f) removing the magnetic field from the surface of the chamber prior to performing a further amplification cycle; and (g) repeating steps (b) through (f) at least once; wherein the nucleic acid target in the sample is amplified and detected. This method may be performed as a single-plex or multi-plex. Multi-plexing may be achieved by using different labels on the probes and/or by labeling or encoding the particles on which the probes are immobilized.

In another embodiment, the present invention provides a method of amplifying and detecting a plurality of nucleic acid targets in a sample comprising: (a) combining in a chamber a sample comprising the plurality of nucleic acid targets, a plurality of primer pairs for priming amplification of the plurality of nucleic acid targets, and a plurality of probe sets complementary to the plurality of nucleic acid targets, wherein each probe set comprises a first probe immobilized on an encoded magnetic bead such that the identity of the first probe is known from the encoded magnetic bead on which it is immobilized, and a second probe comprising a label; (b) performing an amplification cycle to form amplification products for each of the plurality of nucleic acid targets amplified with the plurality of primer pairs; (c) hybridizing the amplification products to the probe sets; (d) applying a magnetic field to a surface of the chamber to draw the encoded magnetic beads and the amplification products hybridized to the probes immobilized on the encoded magnetic beads to the surface of the chamber; (e) detecting a signal from the encoded magnetic beads and a signal from the second probe hybridized to the amplification products; (f) removing the magnetic field from the surface of the chamber prior to performing a further amplification cycle; and (g) repeating steps (b) through (f) at least once; wherein the plurality of nucleic acid targets in the sample are amplified and detected. In certain aspects of the invention, steps (b) through (f) are repeated between 10 to 40 times.

In a further embodiment, the present invention provides a method of amplifying and detecting a plurality of nucleic acid targets in a sample comprising: (a) combining in a chamber a sample comprising the plurality of nucleic acid targets, a plurality of primer pairs for priming amplification of the plurality of nucleic acid targets, a dNTP coupled to a quencher molecule, and a plurality of fluorescently labeled probes complementary to the plurality of nucleic acid targets, wherein the probes are immobilized on a plurality of encoded magnetic beads such that the identity of each probe is known from the encoded magnetic bead on which it is immobilized; (b) performing an amplification cycle to form amplification products comprising quencher molecules for each of the plurality of nucleic acid targets amplified with the plurality of primer pairs; (c) hybridizing the amplification products to the probes immobilized on the encoded magnetic beads; (d) applying a magnetic field to a surface of the chamber to draw the encoded magnetic beads and the amplification products hybridized to the probes immobilized on the encoded magnetic beads to the surface of the chamber; (e) detecting a signal from the encoded magnetic beads and a signal from the labeled probes, wherein a decrease in the signal from the labeled probes indicates hybridization of the labeled probes to the amplification products comprising quencher molecules; (f) removing the magnetic field from the surface of the chamber prior to performing a further amplification cycle; and (g) repeating steps (b) through (f) at least once; wherein the plurality of nucleic acid targets in the sample are amplified and detected. In certain aspects of the invention, steps (b) through (f) are repeated between 10 to 40 times.

In another embodiment, the present invention provides a method of amplifying and detecting a plurality of nucleic acid targets in a sample comprising: (a) combining in a chamber a sample comprising the plurality of nucleic acid targets; a plurality of primer pairs for priming amplification of the plurality of nucleic acid targets, wherein each primer pair comprises a first primer comprising a target specific sequence, a tag sequence 5' of the target specific sequence, and optionally a blocker between the target specific sequence and the tag sequence, and a second primer comprising a target specific sequence; a labeling agent; and a plurality of probes complementary to the tag sequences of the plurality of primer pairs, wherein the probes are immobilized on a plurality of encoded magnetic beads such that the identity of each probe is known from the encoded magnetic bead on which it is immobilized; (b) performing an amplification cycle to form tagged and labeled amplification products for each of the plurality of nucleic acid targets amplified with the plurality of primer pairs; (c) hybridizing the tagged and labeled amplification products to the probes immobilized on the encoded magnetic beads; (d) applying a magnetic field to a surface of the chamber to draw the encoded magnetic beads and the tagged and labeled amplification products hybridized to the probes immobilized on the encoded magnetic beads to the surface of the chamber; (e) detecting the encoded magnetic beads and the tagged and labeled amplification products; (f) removing the magnetic field from the surface of the chamber prior to performing a further amplification cycle; and (g) repeating steps (b) through (f) at least once; wherein the plurality of nucleic acid targets in the sample are amplified and detected. In certain aspects of the invention, steps (b) through (f) are repeated between 10 to 40 times. In certain aspects, the labeling agent is a reporter molecule attached to the second primer of the primer pair. In other aspects, the labeling agent is a nucleic acid intercalating dye. It should be noted that the nucleic acid intercalating agent will label the hybridized complementary tags even in the absence of amplification. This would be problematic in PCR where only an end-point detection is performed because it would be unclear whether amplification was successful or whether the detected signal was only from the intercalating agent labeling the complementary tags. With PCR performed in real time according to the methods disclosed herein, the signal from the intercalating agent would be observed to increase as the number of amplification cycles increased in a successful amplification. Thus allowing the differentiation between successful amplification and the labeling only of the complementary tags.

The methods disclosed herein may further comprise quantifying the initial amount of the nucleic acid target(s) in the sample. The quantification may comprise, for example, determining the relative concentrations of DNA present during the exponential phase of the real-time PCR by plotting fluorescence against cycle number on a logarithmic scale. The amounts of DNA may then be determined by comparing the results to a standard curve produced by real-time PCR of serial dilutions of a known amount of DNA. Additionally, real-time PCR may be combined with reverse transcription polymerase chain reaction to quantify RNAs in a sample, including low abundance RNAs.

The methods disclosed herein provide multiplexing capabilities such that a plurality of primer pairs may amplify a plurality of target nucleic acids in a single PCR reaction. In certain embodiments there are at least 6, 7, 8, 9, 10, 11, or 12 different primer pairs in a PCR reaction. In some embodiments there are between 8 to 100, 8 to 80, 8 to 60, 8 to 40, 8 to 20, 8 to 18, 8 to 16, 8 to 12, 10 to 100, 10 to 80, 10 to 60, 10 to 40, 10 to 20, 10 to 18, 10 to 16, 10 to 12, 12 to 100, 12 to 80, 12 to 60, 12 to 40, 12 to 20, 12 to 18, or 12 to 16 different primer pairs in a PCR reaction. In certain embodiments there are at least 6, 7, 8, 9, 10, 11, or 12 different target nucleic acids in a PCR reaction. In some embodiments there are between 8 to 100, 8 to 80, 8 to 60, 8 to 40, 8 to 20, 8 to 18, 8 to 16, 8 to 12, 10 to 100, 10 to 80, 10 to 60, 10 to 40, 10 to 20, 10 to 18, 10 to 16, 10 to 12, 12 to 100, 12 to 80, 12 to 60, 12 to 40, 12 to 20, 12 to 18, or 12 to 16 different target nucleic acids in a PCR reaction. Probes present in the PCR reaction may comprise a blocked 3' hydroxyl group to prevent extension of the probes by the polymerase. The 3' hydroxyl group may be blocked with, for example, a phosphate group or a 3' inverted dT.

The target nucleic acid sequence may be any sequence of interest. The sample containing the target nucleic acid sequence may be any sample that contains nucleic acids. In certain aspects of the invention the sample is, for example, a subject who is being screened for the presence or absence of one or more genetic mutations or polymorphisms. In another aspect of the invention the sample may be from a subject who is being tested for the presence or absence of a pathogen. Where the sample is obtained from a subject, it may be obtained by methods known to those in the art such as aspiration, biopsy, swabbing, venipuncture, spinal tap, fecal sample, or urine sample. In some aspects of the invention, the sample is an environmental sample such as a water, soil, or air sample. In other aspects of the invention, the sample is from a plant, bacteria, virus, fungi, protozoan, or metazoan.

Each amplification cycle has three phases: a denaturing phase, a primer annealing phase, and a primer extension phase. The amplification cycle can be repeated until the desired amount of amplification product is produced. Typically, the amplification cycle is repeated between about 10 to 40 times. For real-time PCR, detection of the amplification products will typically be done after each amplification cycle. Although in certain aspects of the invention, detection of the amplification products may be done after every second, third, fourth, or fifth amplification cycle. Detection may also be done such that as few as 2 or more amplification cycles are analyzed or detected. The amplification cycle may be performed in the same chamber in which the detection of the amplification occurs, in which case this chamber would need to comprise a heating element so the temperature in the chamber can be adjusted for the denaturing phase, primer annealing phase, and a primer extension phase of the amplification cycle. The heating element would typically be under the control of a processor. The amplification cycle may, however, be performed in a different chamber from the chamber in which detection of the amplification occurs, in which case the "amplification" chamber would need to comprise a heating element but the "detection" or "imaging" chamber would not be required to have a heating element. Where amplification and detection occur in separate chambers, the fluid in which the amplification reaction occurs may be transferred between the chambers by, for example, a pump or piston. The pump or piston may be under the control of a processor. Alternatively, the fluid may be transferred between the chambers manually using, for example, a pipette.

The chamber may be for example, a quartz chamber. A magnetic field may be applied to the chamber to attract magnetic particles within the chamber to a surface of the chamber by placing a permanent magnet adjacent to the surface of the chamber or by turning on an electromagnet adjacent to the surface of the chamber. The magnet need not be in physical contact with the chamber as long as it is close enough for its magnetic field to attract the magnetic particles within the chamber to the chamber surface. The magnetic field may be removed from the chamber by moving the permanent magnet away from the chamber or by turning off the electromagnetic. Of course, an electromagnet that is turned on may also be applied or removed from the chamber by moving closer or farther from the chamber as described above for a permanent magnet. In embodiments where the amplification and detection occur in the same chamber, the magnetic field may be applied during the primer annealing phase of the amplification cycle, during the primer extension phase of the amplification cycle, or following the amplification cycle. In embodiments, where the amplification and detection occur in different chambers, the magnetic field will typically be applied following the amplification cycle when the amplification reaction fluid is transferred into the detection chamber.

The encoded particles and amplification products on the surface of the chamber may be detected using an imaging system such as those described herein. For example, detecting the encoded magnetic beads and the labeled amplification products may comprise imaging fluorescent wavelengths and/or fluorescent intensities emitted from the encoded magnetic beads and the labeled amplification products. The imaging may comprise taking a decoding image to identify the beads on the surface of the chamber and taking an assay imaging to detect amplification products on the surface of the chamber. A comparison of the decoding image and the assay image shows which beads have amplification products bound to them. Since the identities of the probes attached to the beads is known by encoding of the beads, the identity of the amplification product hybridized to the probe may also be determined. The methods of the present invention may further comprise correlating the signal from the directly or indirectly labeled amplification product with the concentration of DNA or RNA in a sample. This correlation may comprise the steps of determining the relative concentrations of DNA present during the exponential phase of real-time PCR by plotting fluorescence against cycle number on a logarithmic scale and comparing the results to a standard curve produced by real-time PCR of serial dilutions of a known amount of DNA or RNA.

In one embodiment, the present invention provides a system for performing multiplexed, real-time PCR comprising: a thermal cycler; an imaging system coupled to the thermal cycler; encoded magnetic particles adapted to be introduced into the thermal cycler; a magnet for selectively introducing a magnetic field to the thermal cycler for immobilizing the encoded magnetic particles.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 13 shows the Factor V Leiden genomic gene sequence (SEQ ID NO: 6 and 7).

FIG. 15 shows various Cystic Fibrosis gene sequences (SEQ ID NO: 8-15).

DESCRIPTION OF ILLUSTRATIVE EMBODIMENTS

A. Imaging Systems

Figure 1:
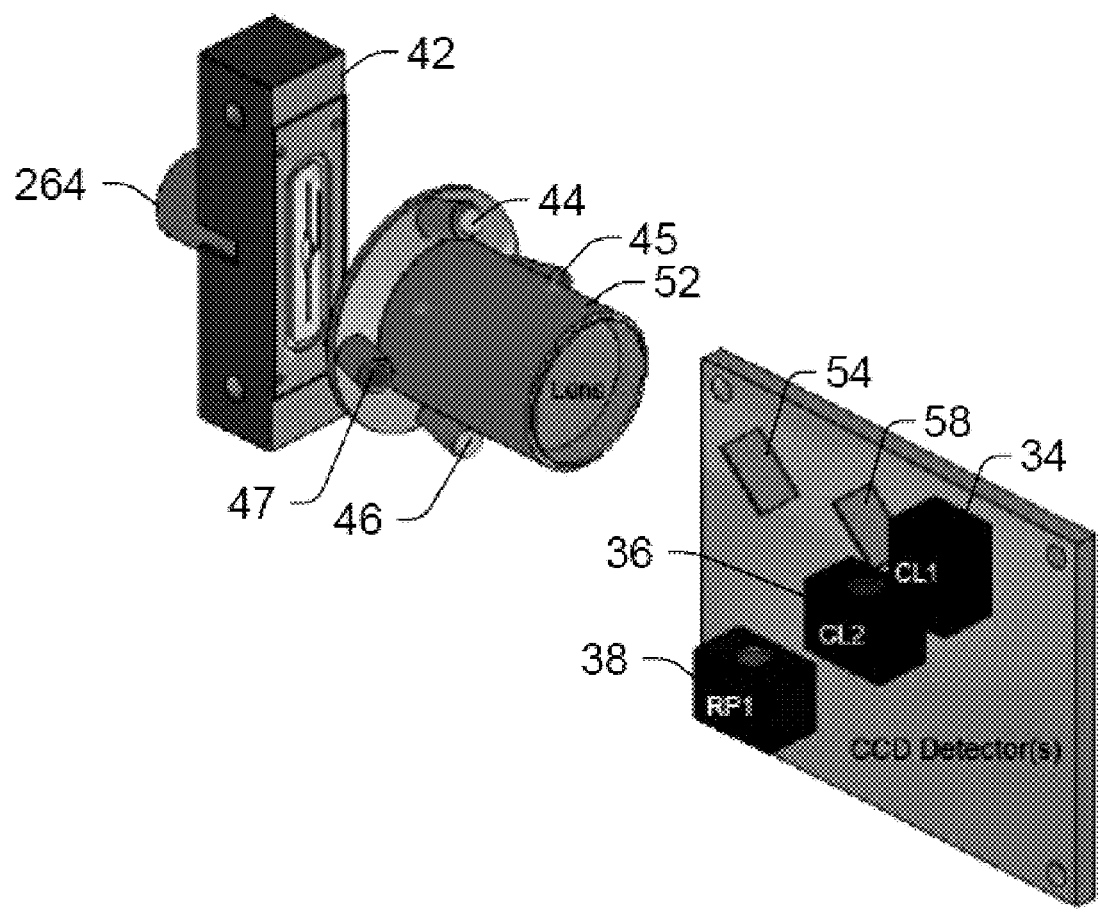
FIG. 1 is a schematic drawing of an imaging system.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 2:
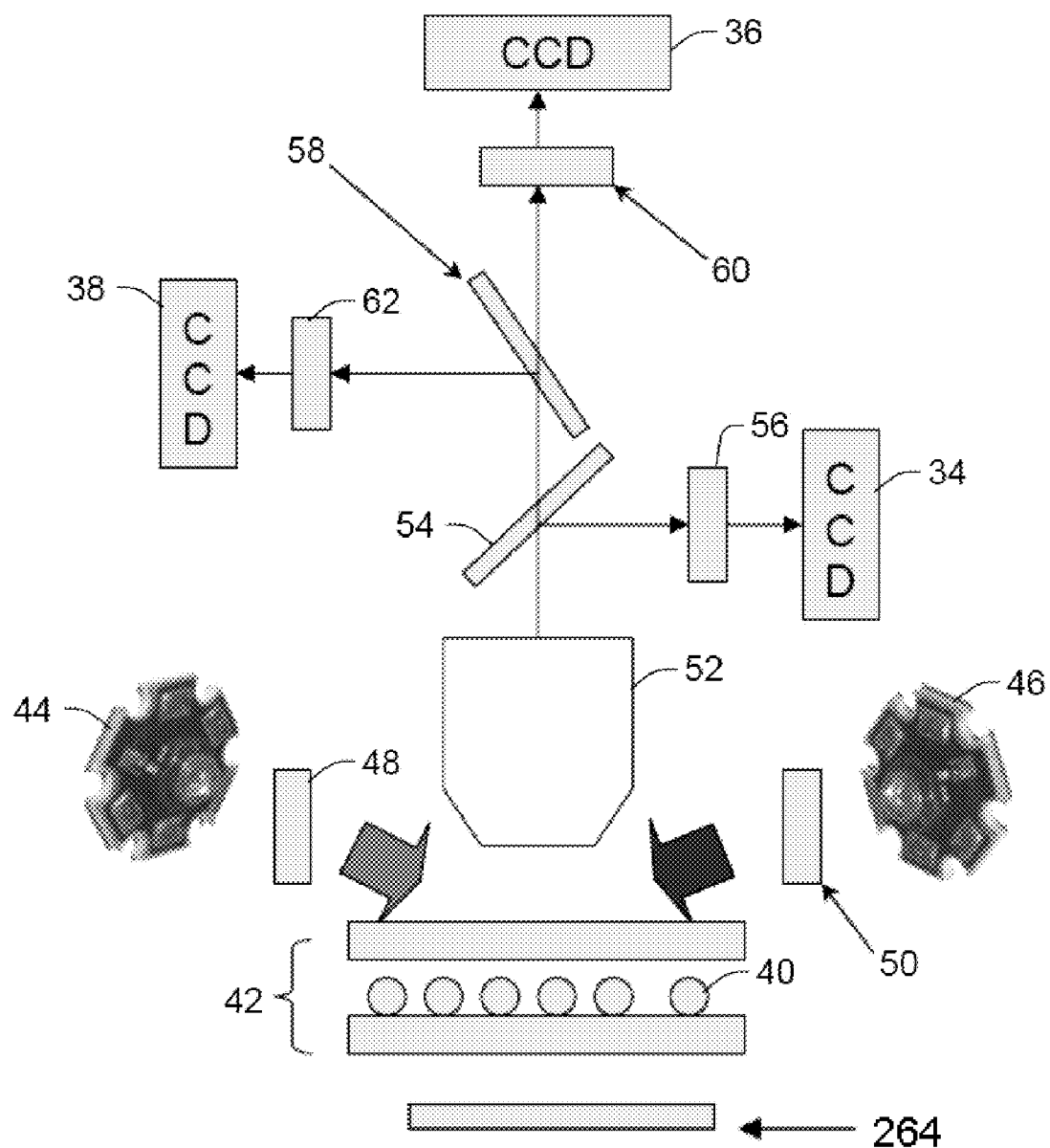
FIG. 2 is a block diagram showing functional details of the system shown in FIG. 1.
Figure 9:
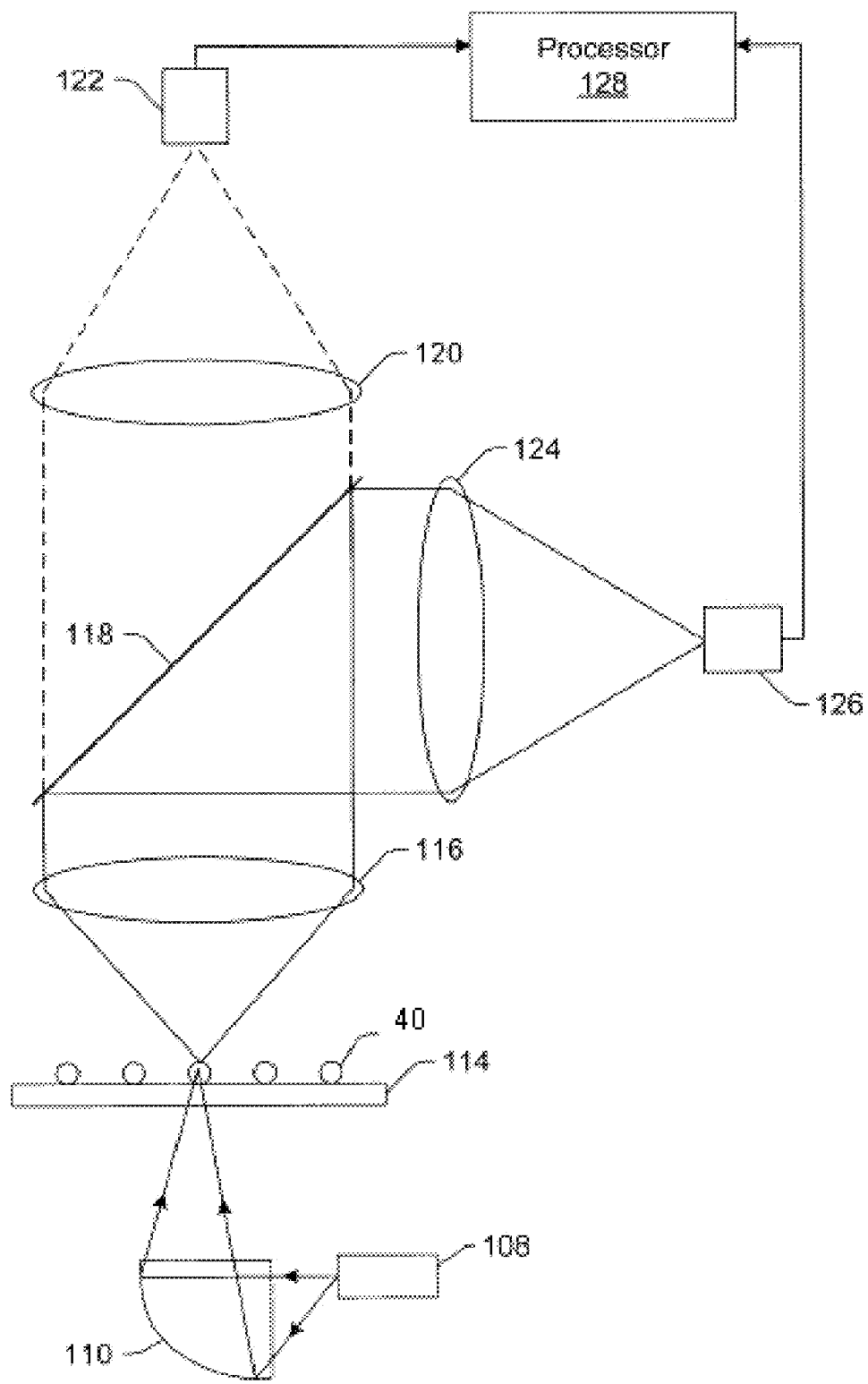
FIG. 9 is a block diagram of an imaging system.

The embodiments of the imaging system of FIGS. 1, 2, and 9 include several configurations using two broad based imaging methods. For fluorescence detection, a single sensor such as a photomultiplier tube (PMT) or avalanche photodiode (APD) per detected wavelength may be employed. Alternatively, a one- or two-dimensional charge coupled device (CCD) or another suitable array detector may be used for fluorescence detection. The excitation source may be configured to provide widespread illumination (i.e., illumination provided over a relatively large area of the imaging volume of the measurement device (such as the entire imaging volume of the measurement device) simultaneously) using light emitted by light sources such as light emitting diodes (LEDs) and delivered to one or more materials in the imaging volume of the measurement device directly or via fiber optics. Alternatively, the excitation source may be configured to provide illumination of a relatively small spot in the imaging volume of the measurement device, and the system may be configured to scan the relatively small spot across the imaging volume. In this manner, the illumination may be configured as a relatively "tiny flying spot" of focused light generated from one or more LEDs, one or more lasers, one or more other suitable light sources, or some combination thereof.

FIGS. 1 and 2 illustrate one embodiment of a system configured to image one or more materials in an imaging volume of a measurement device. This system embodiment includes detectors 34, 36, and 38. Detectors 34, 36, and 38 may be CCD cameras or any other suitable imaging devices. Each of the detectors may have the same configuration or different configurations. Each of the detectors may be configured to detect light (e.g., light fluoresced from particles 40 in imaging volume defined by imaging or detection chamber 42) at a different wavelength or wavelength band. In addition, each of the detectors may be configured to generate images or "capture fluorescent pictures" of particles 40 in imaging chamber 42 (e.g., particles at the bottom of imaging chamber 42).

In FIGS. 1 and 2, the microspheres 40 are fed into the imaging chamber which may be coupled to a thermal cycling element (not shown), such that, the microspheres are contained in the same solution as the PCR reaction, during the PCR reaction. Microspheres 40 may be pulled to a surface of imaging chamber 42 at any phase of the PCR cycle by applying a magnetic field with a magnet 264. Microspheres 40 may be released from the surface by removing the magnetic field. During the next detection phase, the microspheres will again be pulled to the surface for imaging. In FIGS. 1 and 2, the microspheres 40 may also be fed directly to the imaging chamber 42 from a thermal cycler (not shown). Microspheres 40 may be introduced to the imaging chamber 42 and pulled to a surface at any phase of the PCR cycle.

FIGS. 1 and 2 illustrate a magnet 264 for selectively pulling the magnetic microspheres 40 to a surface. The system of FIGS. 1 and 2 also includes light sources 44 and 46 configured to emit light having different wavelengths or different wavelength bands (e.g., one of the light sources may be configured to emit red light and the other light source may be configured to emit green light). The light emitted by light sources 44 and 46 may include, for example, light in any part of the visible wavelength regime. Light sources 44 and 46 may include LEDs or any other suitable light sources known in the art. Light sources 44 and 46 are arranged above the periphery of imaging chamber 42. In addition, the light sources are arranged above the imaging chamber such that each light source directs light to particles 40 in imaging chamber 42 at different directions. The system also includes filters 48 and 50 coupled to light sources 44 and 46, respectfully. Filters 48 and 50 may be bandpass filters or any other suitable spectral filters known in the art. In this manner, the system may use light sources 44 and 46 and filters 48 and 50 to sequentially illuminate the particles with different wavelengths or different wavelength bands of light. For example, red light may be used to excite classification dyes (not shown) that may be internal to the particles, and green light may be used to excite reporter molecules (not shown) coupled to the surface of the particles. Since the classification illumination is dark during reporter measurements (i.e., in the above example, red light is not directed to the particles while green light is directed to the particles), the analyte measurement sensitivity of the system will not be reduced due to crosstalk from out of band light.

The system may also include single lens 52 positioned at the center (or approximately the center) of the illumination "ring." Lens 52 may include any suitable refractive optical element known in the art. Lens 52 is configured to image light scattered and/or fluoresced from the particles onto one or more monochrome CCD detector(s) (e.g., detectors 34, 36, and 38) via one or more optical elements, which may include one or more dichroic and one or more optical bandpass filters. For example, light exiting lens 52 is directed to dichroic filter 54, which may include any suitable dichroic optical element known in the art. Dichroic filter 54 is configured to reflect light of one wavelength or wavelength band and to transmit light of other wavelengths or wavelength bands. Light reflected by dichroic filter 54 is directed to filter 56, which may be a bandpass filter or other suitable spectral filter. Light exiting filter 56 is directed to detector 34. Light transmitted by dichroic filter 54 is directed to dichroic filter 58, which may include any suitable dichroic optical element known in the art. Dichroic filter 58 may be configured to reflect light of one wavelength or wavelength band and to transmit light of other wavelengths or wavelength bands. Light transmitted by dichroic filter 58 is directed to filter 60, which may be a bandpass filter or other suitable spectral filter. Light exiting filter 60 is directed to detector 36. Light reflected by dichroic filter 58 is directed to filter 62, which may be a bandpass filter or other suitable spectral filter. Light exiting filter 62 is directed to detector 38.

Furthermore, although the system shown in FIGS. 1 and 2 includes two light sources, it is to be understood that the system may include any suitable number of light sources. For example, the system may include multiple light sources arranged around the periphery of lens 52. In this manner, light sources may be configured to provide an illumination "ring" surrounding lens 52. Although the system shown in FIGS. 1 and 2 includes three detectors configured to image light scattered and/or fluoresced from the particles at different wavelengths or wavelength bands, it is to be understood that the system may include two or more detectors. For example, the system may include two or more CCD detectors (and optionally fixed filters) that can be used to simultaneously measure the classification channel(s) and reporter channel(s) thereby providing higher throughput for the measurements along with additional hardware cost.

The imaging system may further comprise a fluid handling subsystem for transferring fluids (e.g., PCR reaction, wash buffers) into the detection chamber from a storage vessel or from a thermal cycler or other heated chamber if the detection chamber is not capable of thermal cycling. The storage vessel may be configured as a centrifuge tube, injection syringe, micro titer plate or any other suitable sample container known in the art.

The fluid handling subsystem also includes a pump configured to move fluid from the storage vessel, thermal cycler, or other heated chamber to the detection chamber. The pump may have any suitable configuration known in the art. The fluid handling system may also include one or more valves configured to control the flow of fluid through the system. The fluid handling subsystem may also include a wash reservoir for storing fresh water (or other suitable reagent), which may be transferred by the pump to the detection chamber. The pump may also be configured to transfer materials and any other fluid in the detection chamber to a waste vessel. The waste vessel may have any suitable configuration known in the art. The pumps and valves of the fluid handling subsystem may be controlled by a processor or operated manually.

The system shown in FIGS. 1 and 2 is, therefore, configured to generate a plurality or series of images representing the fluorescent emission of particles 40 at several wavelengths of interest. In addition, the system may be configured to supply a plurality or series of digital images representing the fluorescence emission of the particles to a processor (i.e., a processing engine). The system may or may not include a processor (see e.g. FIG. 9). The processor may be configured to acquire (e.g., receive) image data from detectors 34, 36, and 38. For example, the processor may be coupled to detectors 34, 36, and 38 in any suitable manner known in the art (e.g., via transmission media (not shown), each coupling one of the detectors to the processor, via one or more electronic components (not shown) such as analog-to-digital converters, each coupled between one of the detectors and the processor, etc.). Preferably, the processor is configured to process and analyze these images to determine one or more characteristics of particles 40 such as a classification of the particles and information about an analyte on the surface of the particles. The one or more characteristics may be output by the processor in any suitable format such as a data array with an entry for fluorescent magnitude for each particle for each wavelength. Specifically, the processor may be configured to perform one or more steps of a method for processing and analyzing the images. Examples of methods for processing and analyzing images generated by a system such as that shown in FIGS. 1 and 2 are illustrated in U.S. patent application Ser. No. 11/534,166 entitled "Methods and Systems for Image Data Processing" filed Sep. 21, 2006 by Roth, which is incorporated by reference herein.

The processor may be a processor such as those commonly included in a typical personal computer, mainframe computer system, workstation, etc. In general, the term "computer system" may be broadly defined to encompass any device having one or more processors, which executes instructions from a memory medium. The processor may be implemented using any other appropriate functional hardware. For example, the processor may include a digital signal processor (DSP) with a fixed program in firmware, a field programmable gate array (FPGA), or other programmable logic device (PLD) employing sequential logic "written" in a high level programming language such as very high speed integrated circuits (VHSIC) hardware description language (VHDL). In another example, program instructions (not shown) executable on the processor to perform one or more steps of the computer-implemented methods described in the above-referenced patent application may be coded in a high level language such as C#, with sections in C++ as appropriate, ActiveX controls, JavaBeans, Microsoft Foundation Classes ("MFC"), or other technologies or methodologies, as desired. The program instructions may be implemented in any of various ways, including procedure-based techniques, component-based techniques, and/or object-oriented techniques, among others. Program instructions may be transmitted over or stored on a carrier medium (not shown). The carrier medium may be a transmission medium such as a wire, cable, or wireless transmission link. The carrier medium may also be a storage medium such as a read-only memory, a random access memory, a magnetic or optical disk, or a magnetic tape.

Figure 3:
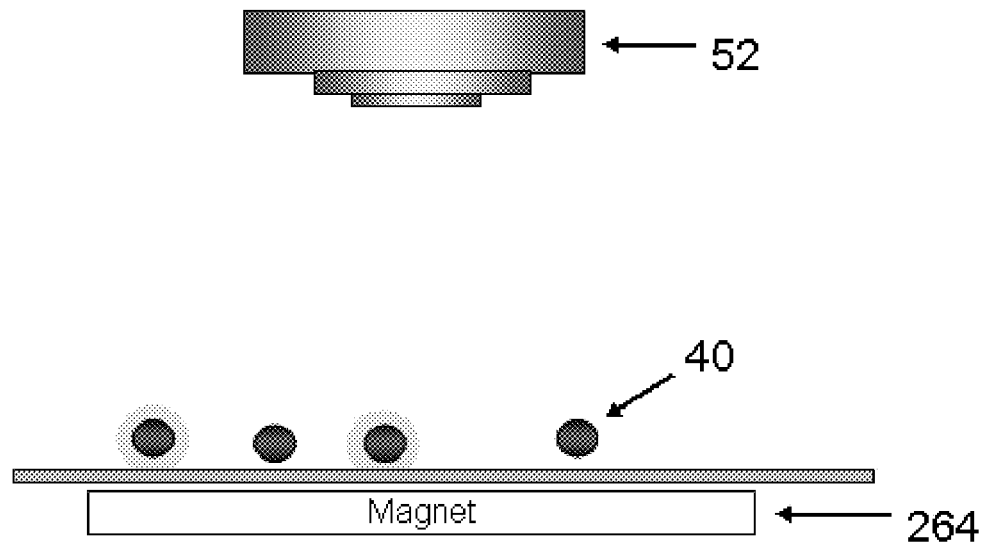
FIG. 3 is a schematic diagram illustrating the relation of microspheres in a detection chamber.
Figure 4:
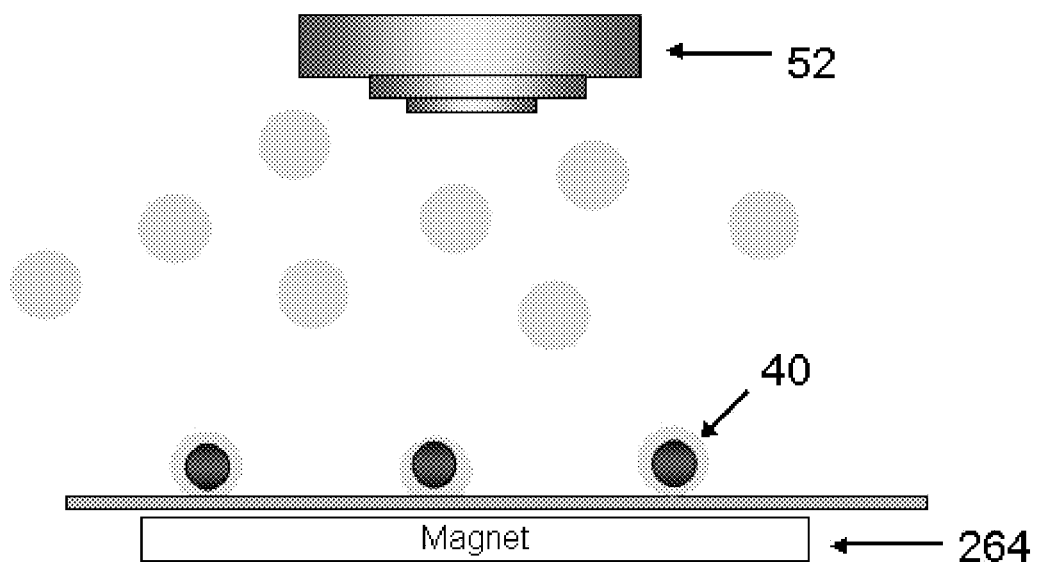
FIG. 4 is another schematic diagram illustrating the relation of microspheres in a detection chamber.

The embodiments of an imaging system of FIGS. 1-4 are configured to substantially immobilize one or more particles 40 in an imaging chamber 42 of the measurement device. Preferably, this system includes magnetic element 264 positioned on the side of imaging chamber 42 opposite the optics of the system. Magnetic element 264 may include any suitable magnetic element known in the art such as a permanent magnet or an electromagnet that can be used to generate a suitable magnetic field. In this manner, dyed particles with embedded magnetite may be used in the embodiments described herein such that the particles can be substantially immobilized in imaging chamber 42 (e.g., at the bottom of the chamber) using a magnetic field generated by magnetic element 264 at the back side of the chamber 42. Although magnetic element 264 is shown spaced from imaging chamber 42 in several figures, the magnetic element 264 may also be in contact with (or coupled to) imaging chamber 42 on the side of the imaging chamber opposite the optical elements of the system. Magnetic element 264 may be further configured as described above. FIG. 3 shows a side view of an imaging chamber with magnet 264 positioned proximate to a surface of the chamber such that beads 40 are substantially immobilized on the surface of the chamber. FIG. 3 illustrates an embodiment in which the fluorophores are attached to the surface of the beads. FIG. 4 also shows a side view of an imaging chamber with magnet 264 positioned proximate to a surface of the chamber such that beads 40 are substantially immobilized on the surface of the chamber. In FIG. 4, however, the fluorophores are attached to nucleic acid sequences (e.g., PCR primers) that are not directly coupled to beads 40, but rather associate with beads 40 via hybridization to sequences that are directly coupled to the beads. This results in "free floating" fluorophores when a complementary probe sequence on a bead is not available for hybridization with the nucleic acid sequence to which the fluorophore is attached. Signals from these free floating fluorophores can increase the background noise when imaging the beads immobilized on the surface of the chamber; however, since the free floating fluorophores are generally not in the focal plane of imaging system, successful imaging of the beads can be achieved. the In addition, although various FIGs show one magnetic element positioned proximate the imaging chamber, it is to be understood that the system may include more than one magnetic element, each of which is positioned proximate the side of the imaging chamber opposite the optics of the system.

The system may include a magnet that is affixed such that magnet is capable of moving to various distances with respect to the imaging chamber 42. After signal acquisition by the imaging system, the magnetic field may be removed (e.g., by using a solenoid to move a permanent magnet or by turning an electromagnet on and off with a switch), and the particles 40 may exit the imaging chamber, while new particles 40 from the next sample are brought into the chamber. The particles in the imaging chamber 42 may be removed and particles may be introduced to the imaging chamber using any of the embodiments described herein. In another embodiment, the particles in the imaging chamber 42 may be released from the surface and remain in the chamber, to interact with other elements in solution and then pulled to the surface again for imaging.

In one embodiment, the imaging chamber design is an imaging chamber that has a relatively smooth internal surface on the side of the imaging chamber proximate the magnetic element 264 such that the beads 40 are randomly distributed across this internal surface as the magnet 264 pulls them to the surface. However, the imaging chamber 42 can also be designed to "hold" the beads in particular spots when the magnetic field is applied. For example, the internal surface of the imaging chamber shown in FIG. 1 may have a square pattern of etched recesses formed therein such that a bead 40 is disposed in one of the etched recesses upon application of a magnetic field as described above. Such etched recesses assist in separating the beads as the magnetic field is applied. The "etched" recesses may be formed by an etching process or any other suitable process known in the art. Furthermore, the configuration and arrangement of the etched recesses may vary depending on, for example, the size of the beads 40 and the selected spacing between the beads.

In another example, an internal surface of an imaging chamber 42 may have a triangle pattern of etched recesses such that bead 40 is disposed in one of the etched recesses upon application of a magnetic field as described above. Therefore, etched recesses assist in separating the beads as the magnetic field is applied. In addition, the "etched" recesses may be formed by an etching process or any other suitable process known in the art. Furthermore, the configuration and arrangement of the etched recesses may vary depending on, for example, the size of the beads and the selected spacing between the beads. Although etched recesses are preferably two-dimensional in the sense that the beads 40 are confined by the recesses in two dimensions, these recesses can be replaced by trenches or any other suitable recesses that are configured to confine the beads in only one direction.

Other embodiments exist relating to methods for substantially immobilizing one or more particles 40 in an imaging volume of a measurement device. Substantially immobilizing the one or more particles may be performed as described herein using magnetic attraction, a vacuum filter substrate or in other ways known in the art. For example, substantially immobilizing the one or more particles in an imaging volume of a measurement device may include applying a magnetic field to one side of an imaging chamber that defines the imaging volume of the measurement device. In addition, this method may include any other step(s) described herein.

Furthermore, this method may be performed by any of the systems described herein. Examples of methods and systems for positioning microspheres for imaging are illustrated in U.S. patent application Ser. No. 11/270,786 to Pempsell filed Nov. 9, 2005, which is incorporated by reference herein. Regardless of the particle immobilization method, the particles are preferably substantially immobilized such that the particles do not move perceptibly during the detector integration period, which may be multiple seconds long.

A further embodiment relates to a system configured to transfer one or more particles to an imaging volume of a measurement device from one or more storage vessels (e.g., an aliquot introduced to the system of FIG. 10), to image the one or more particles in the imaging volume, to substantially immobilize the one or more materials in the imaging volume, or some combination thereof. The system may be configured to transfer the one or more particles as described herein, to image the one or more particles as described herein, to substantially immobilize the one or more particles as described herein, or some combination thereof.

The measurements described herein generally include image processing for analyzing one or more images of particles to determine one or more characteristics of the particles such as numerical values representing the magnitude of fluorescence emission of the particles at multiple detection wavelengths. Subsequent processing of the one or more characteristics of the particles such as using one or more of the numerical values to determine a token ID representing the multiplex subset to which the particles belong and/or a reporter value representing a presence and/or a quantity of analyte bound to the surface of the particles can be performed according to the methods described in U.S. Pat. No. 5,736,330 to Fulton, U.S. Pat. No. 5,981,180 to Chandler et al., U.S. Pat. No. 6,449,562 to Chandler et al., U.S. Pat. No. 6,524,793 to Chandler et al., U.S. Pat. No. 6,592,822 to Chandler, and U.S. Pat. No. 6,939,720 to Chandler et al, which are incorporated by reference herein.

In one example, techniques described in U.S. Pat. No. 5,981,180 to Chandler et al. may be used with the fluorescent measurements described herein in a multiplexing scheme in which the particles are classified into subsets for analysis of multiple analytes in a single sample. Additional examples of systems that may be configured as described herein (e.g., by inclusion of an embodiment of an illumination subsystem described herein) are illustrated in U.S. Pat. No. 5,981,180 to Chandler et al., U.S. Pat. No. 6,046,807 to Chandler, U.S. Pat. No. 6,139,800 to Chandler, U.S. Pat. No. 6,366,354 to Chandler, U.S. Pat. No. 6,411,904 to Chandler, U.S. Pat. No. 6,449,562 to Chandler et al, and U.S. Pat. No. 6,524,793 to Chandler et al, which are incorporated by reference herein. The system shown in FIG. 10 may also be further configured as described in these patents. The system shown in FIG. 10 may be further configured as described herein with respect to other systems and embodiments.

Another embodiment of the imaging systems of FIGS. 1 and 2 configured to perform measurements of particles is shown in FIG. 9. The system shown in FIG. 9 may be used in applications such as multi-analyte measurement of a sample. This embodiment of the system is configured as a fluorescence imaging system. The system includes an illumination subsystem configured to provide illumination of the particles 62 during measurement. In FIG. 9 the illumination subsystem includes LED or LED die 108. LED or LED die 108 may include any appropriate LED or LED die known in the art. In addition, the illumination subsystem may include more than one light source (not shown), each of which is configured to generate light of at least one wavelength or at least one wavelength band. One example of an appropriate combination of light sources for use in the system shown in FIG. 9 includes, but is not limited to, two or more LEDs or LED dies. It is to be understood that a single LED die may contain either a single emission area (of any shape) or multiple emission areas on a single die. Typically, if these multiple emission areas are rectangularly shaped they are referred to as "bars." The light sources, however, may include at least one LED die in combination with one or more other non-LED light sources such as those described above. Light generated by more than one light source may be combined into a common illumination path by a beamsplitter (not shown) or any other suitable optical element known in the art such that light from the light sources may be directed to the particles simultaneously.

Alternatively, the illumination subsystem may include an optical element (not shown) such as a reflecting mirror and a device (not shown) configured to move the optical element into and out of the illumination path depending on which light source is used to illuminate the particles. In this manner, the light sources may be used to sequentially illuminate the particles with different wavelengths or wavelength bands of light. The light source(s) may also illuminate the substrate from above (not shown), rather than from below the substrate.

The light source(s) may be selected to provide light at wavelength(s) or wavelength band(s) that will cause the particles or materials coupled thereto or incorporated therein to emit fluorescence. For instance, the wavelength(s) or wavelength band(s) may be selected to excite fluorophores, fluorescent dyes, or other fluorescent materials incorporated into the particles and/or coupled to a surface of the particles. In this manner, the wavelength(s) or wavelength band(s) may be selected such that the particles emit fluorescence that is used for classification of the particles. In addition, the wavelength(s) or wavelength band(s) may be selected to excite fluorophores, fluorescent dyes, quantum dots, fluorescent nanocrystals, or other fluorescent materials coupled to the particles via a reagent on the surface of the particles or internal to the particles. As such, the wavelength(s) or wavelength band(s) may be selected such that the particles emit fluorescence that is used to detect and/or quantify reaction(s) that have taken place on the surface of the particles or internal to the particles. Alternatively, the wavelength(s) or wavelength band(s) may be selected to excite the particles themselves such that the particles emit fluorescence that can be used to determine physical size characteristics of the particles and/or the existence of a type of particle such that subsequent testing may be selected. An example of an application for such a system is a biodefense application in which output responsive to the fluorescence and/or scattering of particles can be used to detect at a minimum, the potential presence of biological or chemical pathogens.

In addition to detection, a certain set of physical and/or optical characteristics may be analyzed using the output. The illumination subsystem also includes reflector 110 that is substantially elliptical and is disposed in an optical path of the light generated by LED or LED die 108. Reflector 110 is configured to direct light from the LED or LED die to an illumination volume such that an intensity of the light throughout the illumination volume is substantially uniform. LED or LED die 108 and reflector 110 may be further configured as described herein. Particles 40 are disposed in the illumination volume during measurement. In particular, reflector 110 is configured to direct light from LED or LED die 108 to substrate 114 on which particles 40 are immobilized. Particles 40 may include any of the particles described above. Substrate 114 may include any appropriate substrate known in the art. The particles immobilized on substrate 114 may be disposed in an imaging chamber (not shown) or any other device for maintaining a position of substrate 114 and particles 40 immobilized thereon with respect to the illumination subsystem. The device for maintaining a position of substrate 114 may also be configured to alter a position of the substrate (e.g., to focus the illumination onto the substrate) prior to imaging.

Immobilization of the particles 40 on the substrate 114 of FIG. 9 may be performed using magnetic attraction as discussed above, a vacuum filter plate, or any other appropriate method known in the art as discussed above. However, the particles 40 are preferably immobilized such that the particles do no move perceptibly during the detector integration period, which may be multiple seconds long.

The system shown in FIG. 9 also includes a detection subsystem that is configured to generate output responsive to light from (e.g., scattered from and/or emitted by) the particles in the imaging volume. For example, as shown in FIG. 9, the detection subsystem may include optical element 116 and dichroic beamsplitter 118. Optical element 116 is configured to collect and collimate light from substrate 114 and particles 40 immobilized thereon and to direct the light to beamsplitter 118. Optical element 116 may include any appropriate optical element known in the art. In addition, although optical element 116 is shown in FIG. 9 as a single optical element, it is to be understood that optical element 116 may include more than one optical element. Furthermore, although optical element 116 is shown in FIG. 9 as a refractive optical element, it is to be understood that optical element 116 may include one or more reflective optical elements, one or more refractive optical elements, one or more diffractive optical elements, or some combination thereof.

Beamsplitter 118 may include any appropriate beamsplitter known in the art. Beamsplitter 118 may be configured to direct light from optical element 116 to different detectors based on the wavelength of the light. For example, light having a first wavelength or wavelength band may be transmitted by beamsplitter 118, and light having a second wavelength or wavelength band different than the first may be reflected by beamsplitter 118. The detection subsystem may also include optical element 120 and detector 122. Light transmitted by beamsplitter 118 may be directed to optical element 120. Optical element 120 is configured to focus the light transmitted by the beamsplitter onto detector 122. The detection subsystem may further include optical element 124 and detector 126. Light reflected by beamsplitter 118 may be directed to optical element 124. Optical element 124 is configured to focus the light reflected by the beamsplitter onto detector 126. Optical elements 120 and 124 may be configured as described above with respect to optical element 116.

Detectors 122 and 126 may include, for example, charge coupled device (CCD) detectors or any other suitable imaging detectors known in the art such as CMOS detectors, two-dimensional arrays of photosensitive elements, time delay integration (TDI) detectors, etc. In some embodiments, a detector such as a two-dimensional CCD imaging array may be used to acquire an image of substantially an entire substrate or of all particles immobilized on a substrate simultaneously. The number of detectors included in the system may be equal to the number of wavelengths or wavelength bands of interest such that each detector is used to generate images at one of the wavelengths or wavelength bands. Each of the images generated by the detectors may be spectrally filtered using an optical bandpass element (not shown) or any other suitable optical element known in the art, which is disposed in the light path from the beamsplitter to the detectors. A different filter "band" may be used for each captured image. The detection wavelength center and width for each wavelength or wavelength band at which an image is acquired may be matched to the fluorescent emission of interest, whether it is used for particle classification or the reporter signal. In this manner, the detection subsystem of the system shown in FIG. 9 is configured to generate multiple images at different wavelengths or wavelength bands simultaneously.

Although the system shown in FIG. 9 includes two detectors, it is to be understood that the system may include more than two detectors (e.g., three detectors, four detectors, etc.). As described above, the detectors may be configured to generate images at different wavelengths or wavelength bands simultaneously by using one or more optical elements for directing light at different wavelengths or wavelength bands to the different detectors simultaneously. In addition, although the system is shown in FIG. 9 to include multiple detectors, it is to be understood that the system may include a single detector. The single detector may be used to generate multiple images at multiple wavelengths or wavelength bands sequentially. For example, light of different wavelengths or wavelength bands may be directed to the substrate sequentially, and different images may be generated during illumination of the substrate with each of the different wavelengths or wavelength bands.

In another example, different filters for selecting the wavelength or wavelength band of light directed to the single detector may be altered (e.g., by moving the different filters into and out of the imaging path) to generate images at different wavelengths or wavelength bands sequentially. The detection subsystem shown in FIG. 9, therefore, is configured to generate a plurality or series of images representing the fluorescent emission of particles 112 at several wavelengths of interest. In addition, the system may be configured to supply a plurality or series of digital images representing the fluorescence emission of the particles to a processor (i.e., a processing engine). In one such example, the system may include processor 128. Processor 128 may be configured to acquire (e.g., receive) image data from detectors 122 and 126. For example, processor 128 may be coupled to detectors 122 and 126 in any suitable manner known in the art (e.g., via transmission media (not shown), each coupling one of the detectors to the processor, via one or more electronic components (not shown) such as analog-to-digital converters, each coupled between one of the detectors and the processor, etc.). Preferably, processor 128 is configured to process and analyze the images to determine one or more characteristics of particles 40 such as a classification of the particles and information about an analyte on the surface of the particles. The one or more characteristics may be output by the processor in any suitable format such as a data array with an entry for fluorescent magnitude for each particle for each wavelength or wavelength band. Processor 128 may be a processor such as those commonly included in a typical personal computer, mainframe computer system, workstation, etc. In general, the term "computer system" may be broadly defined to encompass any device having one or more processors, which executes instructions from a memory medium. The processor may be implemented using any other appropriate functional hardware. For example, the processor may include a DSP with a fixed program in firmware, a field programmable gate array (FPGA), or other programmable logic device (PLD) employing sequential logic "written" in a high level programming language such as very high speed integrated circuits (VHSIC) hardware description language (VHDL).

In another example, program instructions (not shown) executable on processor 128 may be coded in a high level language such as C#, with sections in C++ as appropriate, ActiveX controls, JavaBeans, Microsoft Foundation Classes ("MFC"), or other technologies or methodologies, as desired. The program instructions may be implemented in any of various ways, including procedure-based techniques, component-based techniques, and/or object-oriented techniques, among others.

The system shown in FIG. 9 may be further configured as described herein with respect to other systems and embodiments.

Figure 10:
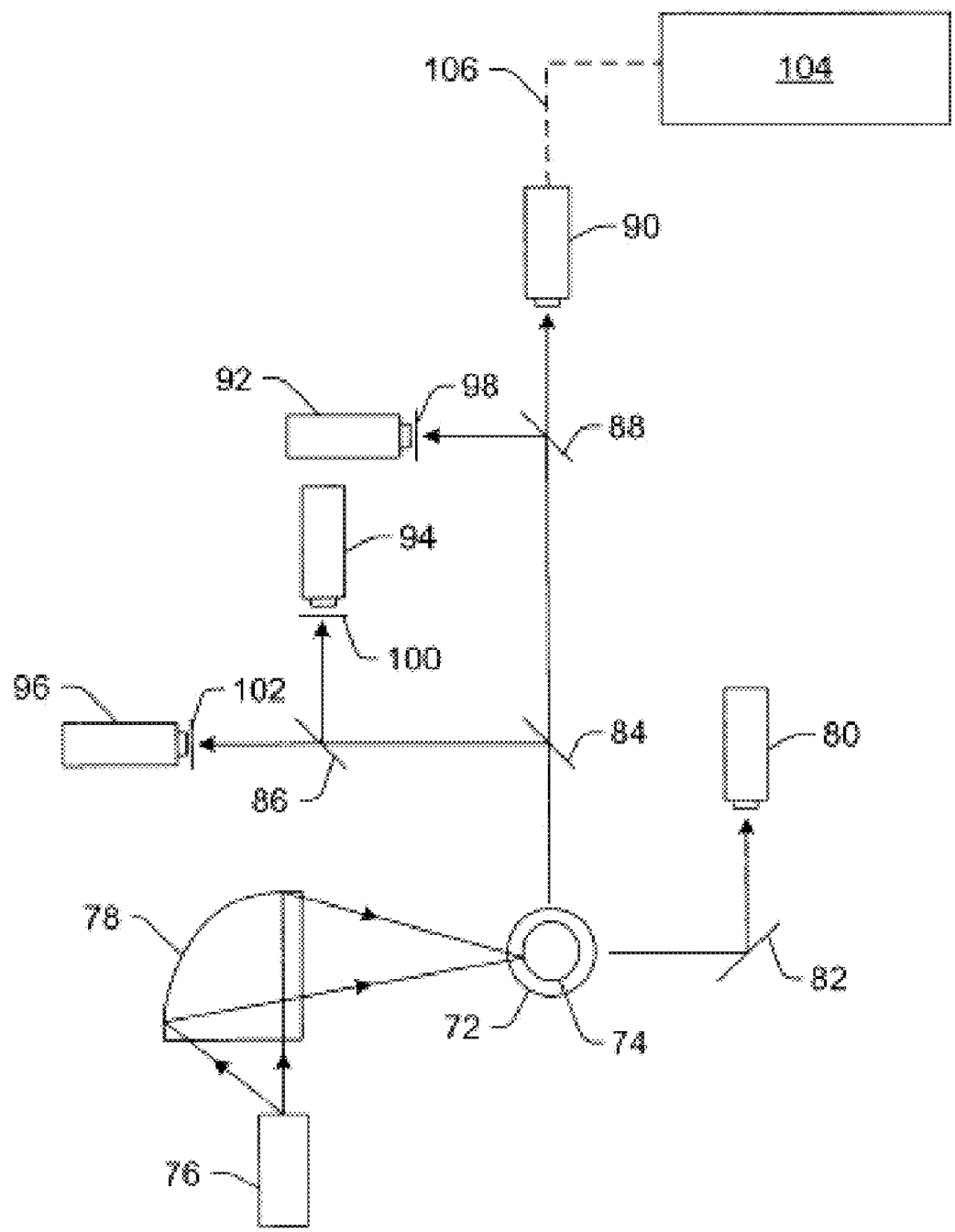
FIG. 10 is a block diagram of a flow cytometer used as an imaging system.

FIG. 10 illustrates a flow cytometer embodiment of an imaging system configured to perform measurements of particles in accordance with certain embodiments of the present invention. The system illustrated in FIG. 10 includes an illumination subsystem configured according to the embodiments described herein. In FIG. 10, the system is shown along a plane through the cross section of cuvette 72 through which particles 74 flow. In one example, the cuvette may be a standard fused silica cuvette such as that used in standard flow cytometers. However, any other suitable type of viewing or delivery configuration, such as a suitably confined sample air-flow stream may also be used to deliver the sample for analysis. Applying the method of real-time PCR to the system of FIG. 10 entails transferring an aliquot of the PCR solution from the thermal cycler to the detection system of FIG. 10. By taking an aliquot at different intervals of the PCR process, quantitation of the initial template or DNA is facilitated. This method may also manipulate the aliquots by adding additional buffers or reagents, or amplification methods that may improve detection. Other methods may include pre-aliquoting PCR reagents prior to loading in a thermal cycler, and removing these samples at separate intervals in the PCR process, or any other assay process.

The illumination subsystem is configured to illuminate particles 74 with light. The illumination subsystem includes LED or LED die 76. The LED or LED die may be any suitable LED or LED die known in the art. In addition, the illumination subsystem may include more than one LED or LED die (not shown). In other embodiments, the illumination subsystem includes LED or LED die 76 and one or more other light sources (not shown) such as LEDs, LED dies, lasers, arc lamps, fiber illuminators, light bulbs, or some combination thereof. The other light source(s) may include any suitable such light source(s) known in the art. In this manner, the illumination subsystem may include more than one light source. In one embodiment, the light sources may be configured to illuminate the particles with light having different wavelengths or wavelength bands (e.g., blue light and green light). In some embodiments, the light sources may be configured to illuminate the particles at different directions.

The illumination subsystem also includes reflector 78 that is substantially elliptical and is configured to direct light from LED or LED die 76 to an illumination volume such that an intensity of the light throughout the illumination volume is substantially uniform or has a selected illumination function in the illumination volume. LED or LED die 76 and reflector 78 may be further configured as described herein. Particles 74 flow through the illumination volume during measurement. In this manner, light exiting reflector 78 illuminates the particles as they flow through the cuvette. The illumination may cause the particles themselves or a fluorophore attached thereto or incorporated therein to emit fluorescent light having one or more wavelengths or wavelength bands. The fluorophore may include any appropriate fluorophore known in the art. In some embodiments, particles 74 themselves are configured to emit fluorescence or to naturally emit fluorescence when illuminated with light of appropriate intensity and wavelength. In one such embodiment, the light exiting reflector 78 causes the particles to emit fluorescence.

The system shown in FIG. 10 also includes a detection subsystem configured to generate output responsive to light from (e.g., scattered from and/or emitted by) particles in the illumination volume. For example, light scattered forwardly from the particles may be directed to detection system 80 by optical element 82, which may be a folding mirror, a suitable light directing component, or a dichroic reflecting component. Alternatively, detection system 80 may be placed directly in the path of the forwardly scattered light. In this manner, optical element 82 may not be included in the system. In one embodiment, the forwardly scattered light may be light scattered by the particles at an angle of about 180° from the direction of illumination by the illumination subsystem, as shown in FIG. 10. The angle of the forwardly scattered light may not be exactly 180° from the direction of illumination such that incident light may not impinge upon the photosensitive surface of the detection system. For example, the forwardly scattered light may be light scattered by the particles at angles less than or greater than 180° from the direction of illumination (e.g., light scattered at an angle of about 170°, about 175°, about 185°, or about 190°). Light scattered by the particles at an angle of about 90° from the direction of illumination may also be collected by the detection subsystem. Light scattered by the particles can also or alternatively be collected at any angle or orientation by the detection subsystem.

In one embodiment, this scattered light may be separated into more than one beam of light by one or more beamsplitters or dichroic mirrors. For example, light scattered at an angle of about 90° to the direction of illumination may be separated into two different beams of light by beamsplitter 84. The two different beams of light may be separated again by beamsplitters 86 and 88 to produce four different beams of light. Each of the beams of light may be directed to a different detection system, which may include one or more detectors. For example, one of the four beams of light may be directed to detection system 90. Detection system 90 may be configured to detect light scattered by the particles. Scattered light detected by detection system 80 and/or detection system 90 may generally be proportional to the volume of the particles that are illuminated by the light source. Therefore, output of detection system 80 and/or output of detection system 90 may be used to determine a diameter of the particles that are in the illumination volume.

In addition, the output of detection system 80 and/or detection system 90 may be used to identify more than one particle that are stuck together or that are passing through the illumination volume at approximately the same time. Therefore, such particles may be distinguished from other sample particles and calibration particles. The other three beams of light may be directed to detection systems 92, 94, and 96. Detection systems 92, 94, and 96 may be configured to detect fluorescence emitted by the fluorophore or the particles themselves. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence.

In some embodiments, spectral filters 98, 100, and 102 may be coupled to detection systems 92, 94, and 96, respectively. The spectral filters may be configured to block fluorescence of wavelengths other than that or those which the detection systems are configured to detect. In addition, one or more lenses (not shown) may be optically coupled to each of the detection systems. The lenses may be configured to focus the scattered light or emitted fluorescence onto a photosensitive surface of the detectors. The detector's output is proportional to the fluorescent light impinging on it and results in a current pulse. The current pulse may be converted to a voltage pulse, low pass filtered, and then digitized by an A/D converter (not shown). Processor 104 such as a digital signal processor (DSP) integrates the area under the pulse to provide a number that represents the magnitude of the fluorescence. As shown in FIG. 10, processor 104 may be coupled to detector 90 via transmission medium 106. Processor 104 may also be coupled to detector 90 indirectly via transmission medium 106 and one or more other components (not shown) such as the A/D converter. The processor may be coupled to other detectors of the system in a similar manner. Processor 104 may be further configured as described herein.

In some embodiments, the output responsive to fluorescence emitted by the fluorophore or particles may be used to determine an identity of the particles and information about a reaction taken or taking place on the surface of the particles. For example, output of two of the detection systems may be used to determine an identity of the particles, and output of the other detection system may be used to determine a reaction taken or taking place on the surface of the particles. Therefore, the selection of the detectors and the spectral filters may vary depending on the type of dyes or fluorophores incorporated into or bound to the particles and/or the reaction being measured (i.e., the dye(s) incorporated into or bound to the reactants involved in the reaction), or may depend upon the fluorescence characteristics of the particles themselves. The detection systems that are used to determine an identity of the sample particles (e.g., detection systems 92 and 94) may be avalanche photodiodes (APDs), photomultiplier tubes (PMTs), or another type of photodetector. The detection system that is used to identify a reaction taken or taking place on the surface of the particles (e.g., detection system 96) may be a PMT, an APD, or another type of photodetector. The measurement system may be further configured as described herein.

Although the system of FIG. 10 includes two detection systems for distinguishing between particles having different dye characteristics, it is to be understood that the system may include more than two detection systems (i.e., 3 detection systems, 4 detection systems, etc.) for distinguishing between particles having different dye characteristics. In such embodiments, the system may include additional beamsplitters and additional detection systems. In addition, spectral filters and/or lenses may be coupled to each of the additional detection systems.

In certain embodiments, the systems disclosed herein include a thermal control element coupled to the imaging chamber 42. With the thermal control element coupled to the imaging chamber 42 the temperature in the imaging chamber may be adjusted as needed for performing various biological reactions. Accordingly, by coupling a thermal control element coupled to the imaging chamber PCR may be performed within the imaging chamber 42. In certain aspects, the imaging chamber may be coupled to a device for release of microspheres from the surface of the chamber, including sonication or vortexing devices. Other embodiments include systems having multiple detection chambers and/or disposable detection chambers.

B. PCR

The polymerase chain reaction (PCR) is a technique widely used in molecular biology to amplify a piece of DNA by in vitro enzymatic replication. Typically, PCR applications employ a heat-stable DNA polymerase, such as Taq polymerase. This DNA polymerase enzymatically assembles a new DNA strand from nucleotides (dNTPs) using single-stranded DNA as template and DNA primers to initiate DNA synthesis. A basic PCR reaction requires several components and reagents including: a DNA template that contains the target sequence to be amplified; one or more primers, which are complementary to the DNA regions at the 5' and 3' ends of the target sequence; a DNA polymerase (e.g., Taq polymerase) that preferably has a temperature optimum at around 70° C.; deoxynucleotide triphosphates (dNTPs); a buffer solution providing a suitable chemical environment for optimum activity and stability of the DNA polymerase; divalent cations, typically magnesium ions ($Mg^{2+}$); and monovalent cation potassium ions.

The majority of PCR methods use thermal cycling to subject the PCR sample to a defined series of temperature steps. Each cycle typically has 2 or 3 discrete temperature steps. The cycling is often preceded by a single temperature step ("initiation") at a high temperature (>90° C.), and followed by one or two temperature steps at the end for final product extension ("final extension") or brief storage ("final hold"). The temperatures used and the length of time they are applied in each cycle depend on a variety of parameters. These include the enzyme used for DNA synthesis, the concentration of divalent ions and dNTPs in the reaction, and the melting temperature (Tm) of the primers. Commonly used temperatures for the various steps in PCR methods are: initialization step —94-96° C.; denaturation step —94-98° C.; annealing step —50-65° C.; extension/elongation step —70-74° C.; final elongation —70-74° C.; final hold —4-10° C.

Real-time polymerase chain reaction, also called quantitative real time polymerase chain reaction (QRT-PCR) or kinetic polymerase chain reaction, is used to amplify and simultaneously quantify a targeted DNA molecule. It enables both detection and quantification (as absolute number of copies or relative amount when normalized to DNA input or additional normalizing genes) of a specific sequence in a DNA sample. Real-time PCR may be combined with reverse transcription polymerase chain reaction to quantify low abundance RNAs. Relative concentrations of DNA present during the exponential phase of real-time PCR are determined by plotting fluorescence against cycle number on a logarithmic scale. Amounts of DNA may then be determined by comparing the results to a standard curve produced by real-time PCR of serial dilutions of a known amount of DNA.

Multiplex-PCR and multiplex real-time PCR use of multiple, unique primer sets within a single PCR reaction to produce amplicons of different DNA sequences. By targeting multiple genes at once, additional information may be gained from a single test run that otherwise would require several times the reagents and more time to perform. Annealing temperatures for each of the primer sets should be optimized to work within a single reaction.

The methods disclosed herein may also utilize asymmetric priming techniques during the PCR process, which may enhance the binding of the reporter probes to complimentary target sequences. Asymmetric PCR is carried with an excess of the primer for the chosen strand to preferentially amplify one strand of the DNA template more than the other.

C. Real-Time PCR Detection Chemistries

There are several commercially available nucleic acid detection chemistries currently used in real-time PCR. These chemistries include DNA binding agents, FRET based nucleic acid detection, hybridization probes, molecular beacons, hydrolysis probes, and dye-primer based systems. Each of these chemistries is discussed in more detail below.

1. DNA Binding Agents

The first analysis of kinetic PCR was performed by Higuchi et al. who used ethidium bromide to bind double-stranded DNA products (Higuchi et al., 1992; Higuchi et al., 1993; U.S. Pat. No. 5,994,056; U.S. Published Application No. 2001/6171785). Ethidium bromide, like all other DNA binding agents used in kinetic PCR, is able to increase in fluorescent intensity upon binding. The resulting increase in signal can be recorded over the course of the reaction, and plotted versus the cycle number. Recording the data in this way is more indicative of the initial concentration of the sample of interest compared to end-point analysis.

Binding dyes are relatively inexpensive as compared to other detection chemistries. The advantages of using these binding dyes are their low cost and excellent signal to noise ratios. Disadvantages include their non-specific binding properties to any double-stranded DNA in the PCR reaction, including amplicons created by primer-dimer formations (Wittwer et al., 1997). In order to confirm the production of a specific amplicon, a melting curve analysis should be performed (Ishiguro et al., 1995). Another drawback is that amplification of a longer product will generate more signal than a shorter one. If amplification efficiencies are different, quantification may be even more inaccurate (Bustin and Nolan, 2004).

SYBR® Green I from Invitrogen™ (Carlsbad, Calif.) is a popular intercalating dye (Bengtsson et al., 2003). SYBR® Green I is a cyclically substituted asymmetric cyanine dye (Zipper et al, 2004; U.S. Pat. Nos. 5,436,134; 5,658,751). A minor groove binding asymmetric cyanine dye known as BEBO, has been used in real-time PCR. BEBO causes a non-specific increase in fluorescence with time, perhaps due to a slow aggregation process and is less sensitive compared to SYBR® Green I. A similar dye called BOXTO has also been reported for use in qPCR (Bengtsson et al., 2003; U.S. Published Application No. 2006/0211028). Like BEBO, BOXTO is less sensitive than SYBR® Green I (U.S. Published Application No. 2006/0211028).

Other common reporters include YO-PRO-1 and thiazole orange (TO) which are intercalating asymmetric cyanine dyes (Nygren et al., 1998). While these dyes exhibit large increases in fluorescence intensity upon binding, TO and Oxazole Yellow (YO) have been reported to perform poorly in real-time PCR (Bengtsson et al., 2003). Other dyes that may be used include, but are not limited to, pico green, acridinium orange, and chromomycin A3 (U.S. Published Application No. 2003/6569627). Dyes that may be compatible with real-time PCR can be obtained from various vendors such as, Invitrogen, Cambrex Bio Science (Walkersville, Md.), Rockland Inc. (Rockland, Me.), Aldrich Chemical Co. (Milwaukee, Wis.), Biotium (Hayward, Calif.), TATAA Biocenter AB. (Goteborg, Sweden) and Idaho Technology (Salt Lake City, Utah) (U.S. Published Application No. 2007/0020672).

A dye known as EvaGreen™ (Biotium) has shown promise in that it is designed to not inhibit PCR, and is more stable in alkaline conditions as compared to SYBR® Green I (Dorak, 2006; U.S. Published Application No. 2006/0211028). Other newer dyes include the LCGreen® dye family (Idaho Technology). LCGreen® I and LCGreen® Plus are the most commercially competitive of these dyes. LCGreen® Plus is considerably brighter than LCGreen® (U.S. Published Application No. 2007/0020672; Dorak, 2006; U.S. Published Application No. 2005/0233335; U.S. Published Application No. 2066/0019253).

2. FRET Based Nucleic Acid Detection

Many real-time nucleic acid detection methods utilize labels that interact by Forster Resonance Energy Transfer (FRET). This mechanism involves a donor and acceptor pair wherein the donor molecule is excited at a particular wavelength, and subsequently transfers its energy non-radiatively to the acceptor molecule. This typically results in a signal change that is indicative of the proximity of the donor and acceptor molecules to one another.

Early methods of FRET based nucleic acid detection that lay a foundation for this technology in general, include work by Heller et al. (U.S. Pat. Nos. 4,996,143; 5,532,129; and 5,565,322, which are incorporated by reference). These patents introduce FRET based nucleic acid detection by including two labeled probes that hybridize to the target sequence in close proximity to each other. This hybridization event causes a transfer of energy to produce a measurable change in spectral response, which indirectly signals the presence of the target.

Cardullo et al. (incorporated by reference) established that fluorescence modulation and nonradiative fluorescence resonance energy transfer can detect nucleic acid hybridization in solution (Cardullo et al., 1988). This study used three FRET based nucleic acid detection strategies. The first includes two 5' labeled probes that were complementary to one another, allowing transfer to occur between a donor and acceptor fluorophore over the length of the hybridized complex. In the second method, fluorescent molecules were covalently attached to two nucleic acids, one at the 3' end and the other at the 5' end. The fluorophore-labeled nucleic acids hybridized to distinct but closely spaced sequences of a longer, unlabeled nucleic acid. Finally, an intercalating dye was used as a donor for an acceptor fluorophore that was covalently attached at the 5' end of the probe.

Morrison et al. (1989), incorporated by reference, used complementary labeled probes to detect unlabeled target DNA by competitive hybridization, producing fluorescence signals which increased with increasing target DNA concentration. In this instance, two probes were used that were complementary to one another and labeled at their 5' and 3' ends with fluorescein and fluorescein quencher, respectively. Later work also showed that fluorescence melting curves could be used to monitor hybridization (Morrison and Stols, 1993).

3. Hybridization Probes

Hybridization probes used in real-time PCR were developed mainly for use with the Roche LightCycler® instruments (U.S. Published Application No. 2001/6174670; U.S. Published Application No. 2000/6140054). These are sometimes referred to as FRET probes, LightCycler® probes, or dual FRET probes (Espy et al., 2006).

Hybridization probes are used in a format in which FRET is measured directly (Wilhelm and Pingoud, 2003). Each of the two probes is labeled with a respective member of a fluorescent energy transfer pair, such that upon hybridization to adjacent regions of the target DNA sequence, the excitation energy is transferred from the donor to the acceptor, and subsequent emission by the acceptor can be recorded as reporter signal (Wittwer et al., 1997). The two probes anneal to the target sequence so that the upstream probe is fluorescently labeled at its 3' end and the downstream probe is labeled at its 5' end. The 3' end of the downstream probe is typically blocked by phosphorylation or some other means to prevent extension of the probe during PCR. The dye coupled to the 3' end of the upstream probe is sufficient to prevent extension of this probe. This reporter system is different from other FRET based detection methods (molecular beacons, TaqMan®, etc.) in that it uses FRET to generate rather than to quench the fluorescent signal (Dorak, 2006).

Typical acceptor fluorophores include the cyanine dyes (Cy3 and Cy5), 6-carboxy-4,7,2',7'-tetrachlorofluorescein (TET), 6-carboxy-N,N,N',N'-tetramethylrhodamine (TAMRA), and 6-carboxyrhodamine X (ROX). Donor fluorophores are usually 6-carboxyfluoroscein (FAM) (Wilhelm and Pingoud, 2003). Hybridization probes are particularly advantageous for genotyping and mismatch detection. Melting curve analysis can be performed in addition to the per-cycle monitoring of fluorescence during the PCR reaction. A slow heating of the sample after probe hybridization can provide additional qualitative information about the sequence of interest (Lay and Wittwer, 1997; Bernard et al., 1998a; Bernard et al., 1998b). Base-pair mismatches will shift the stability of a duplex, in varying amounts, depending on the mismatch type and location in the sequence (Guo et al., 1997).

4. Molecular Beacons

Molecular beacons, also known as hairpin probes, are stem-loop structures that open and hybridize in the presence of a complementary target sequence, typically causing an increase in fluorescence (U.S. Pat. No. 5,925,517); U.S. Published Application No. 2006/103476). Molecular beacons typically have a nucleic acid target complement sequence flanked by members of an affinity pair that, under assay conditions in the absence of target, interact with one another to form a stem duplex. Hybridization of the probes to their preselected target sequences produces a conformational change in the probes, forcing the "arms" apart and eliminating the stem duplex and thereby separating the fluorophore and quencher.

5. Hydrolysis Probes

Hydrolysis probes, also known as the TaqMan® assay (U.S. Pat. No. 5,210,015), are popular because they only involve a single probe per target sequence, as opposed to two probes (as in hybridization probes). This results in a cost savings per sample. The design of these probes is also less complicated than that of molecular beacons. These are typically labeled with a reporter on the 5' end and a quencher on the 3' end. When the reporter and quencher are fixed onto the same probe, they are forced to remain in close proximity. This proximity effectively quenches the reporter signal, even when the probe is hybridized to the target sequence. During the extension or elongation phase of the PCR reaction, a polymerase known as Taq polymerase is used because of its 5' exonuclease activity. The polymerase uses the upstream primer as a binding site and then extends. Hydrolysis probes are cleaved during polymerase extension at their 5' end by the 5'-exonuclease activity of Taq. When this occurs, the reporter fluorophore is released from the probe, and subsequently, is no longer in close proximity to the quencher. This produces a perpetual increase in reporter signal with each extension phase as the PCR reaction continues cycling. In order to ensure maximal signal with each cycle, hydrolysis probes are designed with a Tm that is roughly 10° C. higher than the primers in the reaction.

However, the process of cleaving the 5' end of the probe need not require amplification or extension of the target sequence (U.S. Pat. No. 5,487,972). This is accomplished by placing the probe adjacent to the upstream primer, on the target sequence. In this manner, sequential rounds of annealing and subsequent probe hydrolysis can occur, resulting in a significant amount of signal generation in the absence of polymerization. Uses of the real-time hydrolysis probe reaction are also described in U.S. Pat. Nos. 5,538,848 and 7,205,105, both of which are incorporated by references.

6. Dye-Primer Based Systems

There are numerous dye-labeled primer based systems available for real-time PCR. These range in complexity from simple hairpin primer systems to more complex primer structures where the stem-loop portion of the hairpin probe is attached via a non-amplifiable linker to the specific PCR primer. These methods have the advantage that they do not require an additional intervening labeled probe that is essential for probe-based assay systems and they also allow for multiplexing that is not possible with DNA binding dyes. However, the success of each of these methods is dependent upon careful design of the primer sequences.

Hairpin primers contain inverted repeat sequences that are separated by a sequence that is complementary to the target DNA (Nazarenko et al., 1997; Nazarenko et al., 2002; U.S. Pat. No. 5,866,336). The repeats anneal to form a hairpin structure, such that a fluorophore at the 5'-end is in close proximity to a quencher at the 3'-end, quenching the fluorescent signal. The hairpin primer is designed so that it will preferentially bind to the target DNA, rather than retain the hairpin structure. As the PCR reaction progresses, the primer anneals to the accumulating PCR product, the fluorophore and quencher become physically separated, and the level of fluorescence increases.

Invitrogen's LUX™ (Light Upon eXtension) primers are fluorogenic hairpin primers which contain a short 4-6 nucleotide extension at the 5' end of the primer that is complementary to an internal sequence near the 3' end and overlaps the position of a fluorophore attached near the 3' end (Chen et al., 2004; Bustin, 2002). Basepairing between the complementary sequences forms a double-stranded stem which quenches the reporter dye that is in close proximity at the 3' end of the primer. During PCR, the LUX™ primer is incorporated into the new DNA strand and then becomes linearized when a new complementary second strand is generated. This structural change results in an up to 10-fold increase in the fluorescent signal. These primers can be difficult to design and secondary structure must be carefully analyzed to ensure that the probe anneals preferentially to the PCR product. Design and validation services for custom LUX™ primers are available from Invitrogen.

More recently, hairpin probes have become part of the PCR primer (Bustin, 2002). In this approach, once the primer is extended, the sequence within the hairpin anneals to the newly synthesized PCR product, disrupting the hairpin and separating the fluorophore and quencher.

Scorpion® primers are bifunctional molecules in which an upstream hairpin probe sequence is covalently linked to a downstream primer sequence (U.S. Published Application No. 2001/6270967; U.S. Published Application No. 2005/0164219; Whitcombe et al., 1999). The probe contains a fluorophore at the 5' end and a quencher at the 3' end. In the absence of the target, the probe forms a 6-7 base stem, bringing the fluorophore and quencher in close proximity and allowing the quencher to absorb the fluorescence emitted by the fluorophore. The loop portion of the scorpion probe section consists of sequence complementary to a portion of the target sequence within 11 bases downstream from the 3' end of the primer sequence. In the presence of the target, the probe becomes attached to the target region synthesized in the first PCR cycle. Following the second cycle of denaturation and annealing, the probe and the target hybridize. Denaturation of the hairpin loop requires less energy than the new DNA duplex produced. Thus, the scorpion probe loop sequence hybridizes to a portion of the newly produced PCR product, resulting in separation of the fluorophore from the quencher and an increase in the fluorescence emitted.

As with all dye-primer based methods, the design of Scorpion primers follows strict design considerations for secondary structure and primer sequence to ensure that a secondary reaction will not compete with the correct probing event. The primer pair should be designed to give an amplicon of approximately 100-200 bp. Ideally, the primers should have as little secondary structure as possible and should be tested for hairpin formation and secondary structures. The primer should be designed such that it will not hybridize to the probe element as this would lead to linearization and an increase in non-specific fluorescence emission. The Tm's of the two primers should be similar and the stem Tm should be 5-10° C. higher than the probe Tm. The probe sequence should be 17-27 bases in length and the probe target should be 11 bases or less from the 3' end of the scorpion. The stem sequence should be 6 to 7 bases in length and should contain primarily cytosine and guanine. The 5' stem sequence should begin with a cytosine as guanine may quench the fluorophore. Several oligonucleotide design software packages contain algorithms for Scorpion primer design and custom design services are available from some oligonucleotide vendors as well.

The Plexor™ system from Promega is a real-time PCR technology that has the advantage that there are no probes to design and only one PCR primer is labeled (U.S. Pat. No. 5,432,272; U.S. Published Application No. 2000/6140496; U.S. Published Application No. 2003/6617106). This technology takes advantage of the specific interaction between two modified nucleotides, isoguanine (iso-dG) and 5'-methylisocytosine (iso-dC) (Sherrill et al., 2004; Johnson et al., 2004; Moser and Prudent, 2003). Main features of this technology are that the iso-bases will only base pair with the complementary iso-base and DNA polymerase will only incorporate an iso-base when the corresponding complementary iso-base is present in the existing sequence. One PCR primer is synthesized with a fluorescently-labeled iso-dC residue as the 5'-terminal nucleotide. As amplification progresses, the labeled primer is annealed and extended, becoming incorporated in the PCR product. A quencher-labeled iso-dGTP (dabsyl-iso-dGTP), available as the free nucleotide in the PCR master mix, specifically base pairs with the iso-dC and becomes incorporated in the complementary PCR strand, quenching the fluorescent signal. Primer design for the Plexor system is relatively simple as compared to some of the other dye-primer systems and usually follows typical target-specific primer design considerations. A web-based Plexor Primer Design Software, available from Promega, assists in selecting the appropriate dye and quencher combinations, and provides links to oligonucleotide suppliers licensed to provide iso-base containing primers.

D. Exemplary Chemistries

As discussed above, there are several commercially available nucleic acid detection chemistries currently used in real-time PCR. Current real-time PCR technologies are, however, limited in their multiplexing capabilities to reactions of about 1-6 plex. The methods and systems of the present invention can achieve far greater real-time PCR multiplexing using commercially available nucleic acid detection chemistries, including detection chemistries not previously used for real-time PCR. Embodiments describing the use of several of these detection chemistries in the context of the present invention are discussed below.

1. Molecular Beacons

Molecular beacons, also known as hairpin probes, can be described as stem-loop structures that open and hybridize in the presence of a complementary target sequence, typically causing an increase in fluorescence but in the absence thereof, form a stem-loop structure resulting in decreased fluorescence (U.S. Pat. No. 5,925,517; U.S. Published Application No. 2006/103476). Probes according to one embodiment of the present invention are labeled probes that have a nucleic acid target complement sequence flanked by members of an affinity pair, or arms, that, under assay conditions in the absence of target, interact with one another to form a stem duplex. Hybridization of the probes to their preselected target sequences produces a conformational change in the probes, forcing the arms apart and eliminating the stem duplex. Embodiments of probes according to this invention employ interactive labels, whereby that conformational change can be detected, or employ a specially limited allele-discriminating structure, or both. A characteristic change in signal level depends on whether the label moieties are proximate due to the probes being in the closed position or are separated due to the probes being in the open position. According to this embodiment, molecular beacons are also bound to a spectrally or otherwise distinguishable particle, which provides for higher levels of multiplexing than were previously possible by using conventional methods wherein the dyes attached to the hairpin probes by distinguishing the color of the dye rather than the distinguishing properties of the particle attached to the capture probe.

Figure 5:
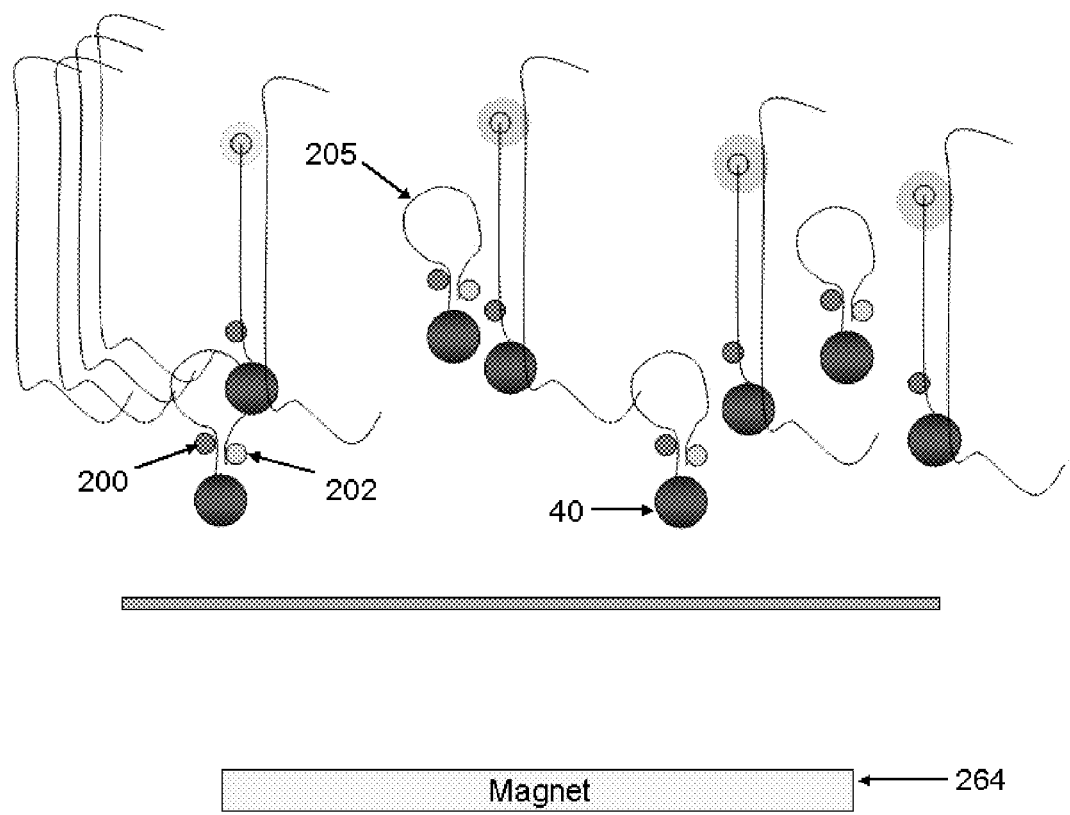
FIG. 5 is an illustration of molecular beacon probes in their hairpin conformation and in their open conformation when hybridized to a complementary nucleic acid sequence.
Figure 6:
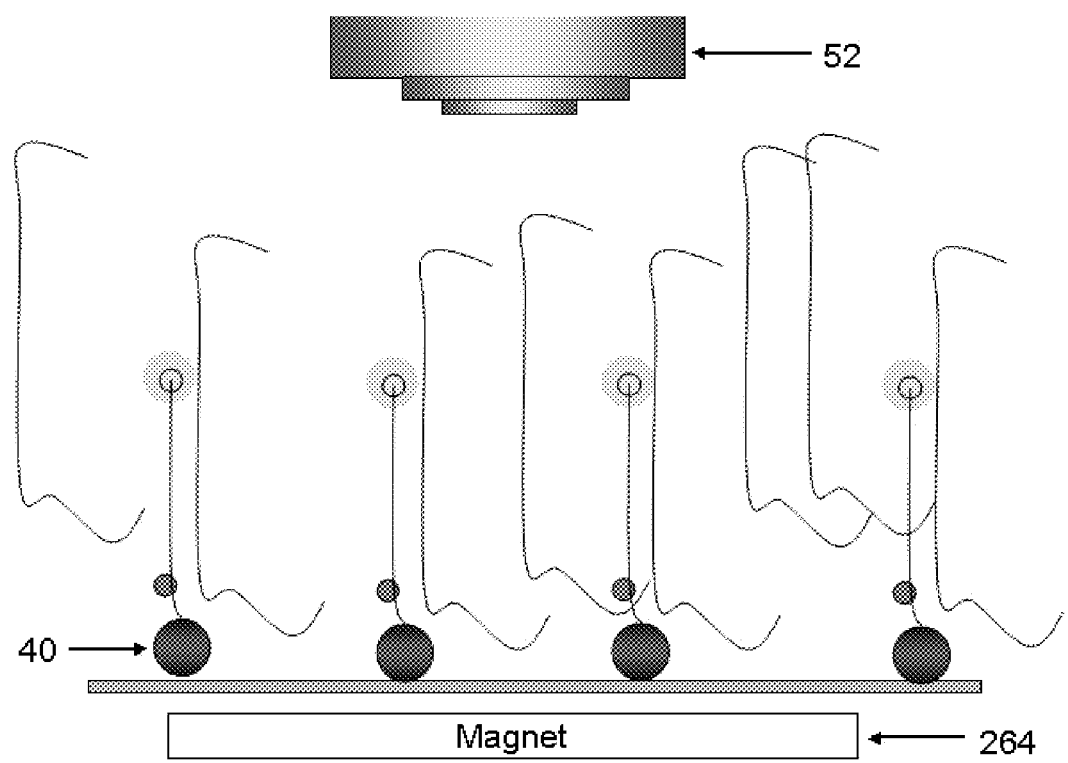
FIG. 6 is an illustration of molecular beacon probes in their open conformation when hybridized to a complementary nucleic acid sequence. Positioning of the magnet in proximity to the imaging chamber results in the molecular beacon probes being immobilized on the surface of the imaging chamber because they are attached to magnetically responsive microspheres.

FIGS. 5 and 6 illustrate how one embodiment of the present invention can separate the fluorochrome from the quenching molecule allowing for detectable fluorescence on the surface of a particle. In FIG. 5, hairpin probes coupled to a quenching molecule and a fluorochrome are homogeneous in solution. Quenching molecule 200 limits the amount of fluorescence emitted by the fluorochrome molecule 202 when the probe is in the hairpin formation. The oligonucleotide probe in the hairpin formation is denoted as 205 in FIG. 5. When the inner loop of the hairpin molecule hybridizes to a target amplicon, the fluorochrome and the quenching molecule are separated as illustrated in FIGS. 5 and 6 allowing for detectable fluorescence on the surface of the bead 40. To image this fluorescence, the beads 40 are pulled to the planar array by moving magnetic element 264 proximate to the array and detecting the fluorescence with an imaging system, such as the imaging systems illustrated in FIGS. 1-2, and 9.

2. Hybridization Probes

Hybridization probes used in real-time PCR are sometimes referred to as FRET probes, LightCycler® probes, or dual FRET probes (Espy et al., 2006). Hybridization probes are used in a format in which FRET is measured directly (Wilhelm and Pingoud, 2003). Each of the two probes is labeled with a respective member of a fluorescent energy transfer pair, such that upon hybridization to adjacent regions of the target DNA sequence, the excitation energy is transferred from the donor to the acceptor, and subsequent emission by the acceptor can be recorded as reporter signal (Wittwer et al., 1997). The two probes anneal to the target sequence so that the upstream probe is fluorescently labeled at its 3' end and the downstream probe is labeled at its 5' end. The 3' end of the downstream probe is typically blocked by phosphorylation or some other means to prevent extension of the probe during PCR. The dye coupled to the 3' end of the upstream probe is sufficient to prevent extension of this probe.

In this embodiment one of two of the hybridization probes can be coupled to the distinguishable particles (e.g., encoded beads). In this instance the capture probe coupled to the particle will be complimentary to the target nucleic acid sequence of interest and the uncoupled probe will hybridize to an adjacent region along the target sequence. In the context of a real-time PCR reaction, the target sequence is the amplicon. Either the donor or the acceptor fluorophores can be attached to the oligonucleotide sequence that is attached to the particle.

Typical acceptor fluorophores include the cyanine dyes (Cy3 and Cy5), 6-carboxy-4,7,2',7'-tetrachlorofluorescein (TET), 6-carboxy-N,N,N',N'-tetramethylrhodamine (TAMRA), and 6-carboxyrhodamine X (ROX). Donor fluorophores are usually 6-carboxyfluoroscein (FAM) (Wilhelm and Pingoud, 2003). Genotyping of the target sequence is accomplished by matching the reporter probes to their corresponding sequences.

Figure 7:
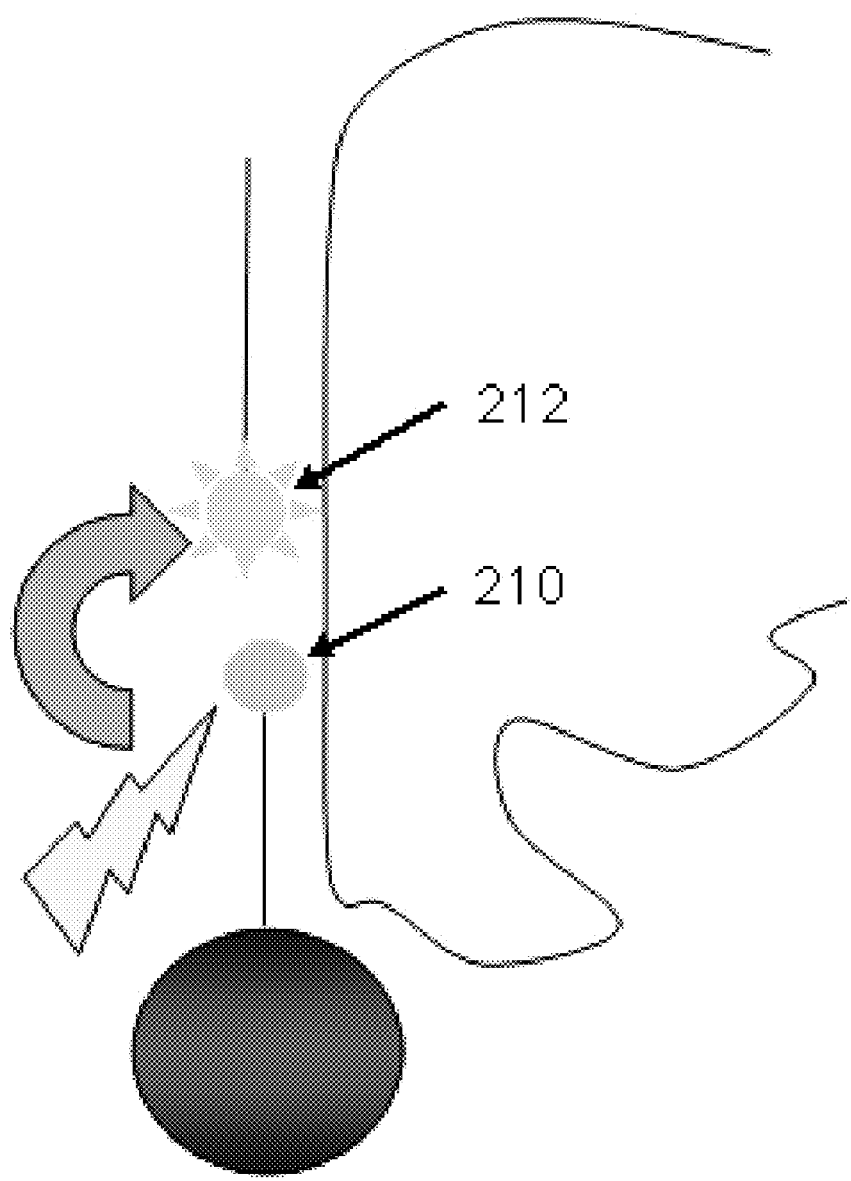
FIG. 7 illustrates a FRET detection chemistry.

FIG. 7 illustrates a modified FRET (Fluorescence Resonance Energy Transfer) hybridization probe in the context of the present invention. Donor fluorophore 210 is attached to the probe immobilized on the surface of paramagnetic microsphere 40. Upon reaching the detection phase of each PCR cycle, the temperature of the solution will be conducive to hybridization of both the donor-labeled probe and acceptor-labeled probe to the target sequence. The close proximity of the donor 210 and acceptor 212 pair will allow for Fluorescence Resonance Energy Transfer. This will result in fluorescence only near the surface of the bead 40, by allowing the acceptor molecule 212 to emit light at a different wavelength than the donor 210.

Thus, in one embodiment of performing a method for multiplexed, real-time amplification and detection of a plurality of nucleic acid targets in a sample using FRET hybridization probes, one would combine in a chamber a sample comprising the plurality of nucleic acid targets, a plurality of primer pairs for priming amplification of the plurality of nucleic acid targets, and a plurality of probe sets complementary to the plurality of nucleic acid targets, wherein each probe set comprises a first probe labeled with a first member of a fluorescent energy transfer pair and immobilized on an encoded magnetic bead such that the identity of the first probe is known from the encoded magnetic bead on which it is immobilized, and a second probe with a second member of the fluorescent energy transfer pair. One would then perform an amplification cycle to form amplification products for each of the plurality of nucleic acid targets amplified with the plurality of primer pairs. The amplification products would be hybridized to the probe sets. By applying a magnetic field to a surface of the chamber the encoded magnetic beads and the amplification products hybridized to the probes immobilized on the encoded magnetic beads are drawn to the surface of the chamber, where an imaging system, such as those described elsewhere herein, detects a signal from the encoded magnetic beads and a signal from the fluorescent energy transfer pair hybridized to the amplification products. The magnetic field may then removed from the surface of the chamber in order to performing a further amplification cycle. The amplification and detection may be repeated the desired number of times to obtain real-time quantitative data on the reaction. It should be noted that the signal from the fluorescent energy transfer pair may be an increase in fluorescence or a decrease in fluorescence depending on the reporter molecules employed.

This two probe system may also be used without a FRET pair. In this embodiment only the probe that is not coupled to the particle is labeled, and therefore the hybridization of both probes to the target sequence is detectable by virtue of the label on one of the two probes. For example, one would combine in a chamber a sample comprising a plurality of nucleic acid targets, a plurality of primer pairs for priming amplification of the plurality of nucleic acid targets, and a plurality of probe sets complementary to the plurality of nucleic acid targets, wherein each probe set comprises a first probe immobilized on an encoded magnetic bead such that the identity of the first probe is known from the encoded magnetic bead on which it is immobilized, and a second probe comprising a label. An amplification cycle is performed to form amplification products for each of the plurality of nucleic acid targets amplified with the plurality of primer pairs. The amplification products are hybridized to the probe sets, and a magnetic field is applied to a surface of the chamber to draw the encoded magnetic beads and the amplification products hybridized to the probes immobilized on the encoded magnetic beads to the surface of the chamber. The non-immobilized, labeled probe would also be pulled to the surface of the chamber because it is hybridized to a complementary sequence on the amplification product. An imaging system, such as those described elsewhere herein, may then be used to detect a signal from the encoded magnetic beads and a signal from the second probe hybridized to the amplification products. The magnetic field may then be removed from the surface of the chamber prior to performing a further amplification cycle. The amplification and detection may be repeated the desired number of times to obtain real-time quantitative data on the reaction.

Additional free floating FRET dyes or other reporter molecules which are attached to probes (e.g., a third probe, fourth probe, etc. of a probe set) may be included in certain embodiments, wherein more than one pair of probes is allowed to hybridize to the target nucleic acid sequence at any given time so long as one probe of the probe set is coupled to a particle or magnetic encoded particle. These additional probes can further increase the sensitivity, specificity, and multiplexing ability of the method by adding additional distinguishing features or additional reporter molecules which are attached to the target. For example, by having a probe which is coupled to a magnetic encoded particle, that probe may hybridize to a target which is longer than the probe, such that other probes which are modified with other reporter molecules may hybridize to a region of the target sequence that is either 5' or 3' to the probe that is coupled to the magnetic encoded particle.

Additional reagents may be used to improve the efficiency of any of the embodiments described herein. These reagents may improve the methods by using PCR additives that are known to those skilled in the art. BSA or other molecules which act as blocking agents or detergents or surfactants may also improve the methods described herein. BSA or other similar reagents known to those skilled in the art may improve a PCR reaction performed in a glass or quartz chamber by reducing the attraction of DNA and other reagents to the surfaces of the reaction chamber. Other additives may be used which exhibit molecular crowding effects to improve the time to hybridization. Other molecules, reagents, chemicals, solutions known to those skilled in the art which may improve the time to hybridization may also be used. An example of such may be nucleic acid binding proteins or minor groove binders.

Those skilled in the art will recognize that modifications to the reporter dye, such as the well-known method of adding sulfate groups, will alter the hydrophilicity of the dye molecules, which may lead to less non-specific binding to the encoded magnetic particles.

3. Two Probe Competition

Other embodiments employ the use of two probes per target nucleic acid sequence. One probe is attached to a bead and may be labeled with a fluorophore. A complimentary "free-floating" probe is also added that contains either a quencher or a fluorophore pair such that FRET may occur. In this instance, the probe on the bead may contain a fluorophore at the 3' end, while being attached to the bead at the 5' end. The free-floating probe will be able to quench the signal associated with the fluorophore on the bead by being designed as a reverse compliment of the same, and having a quenching moiety at its 5' end, such that it is in close proximity to the fluorophore, and therefore achieves a decrease in signal upon hybridization to the probe. These probes will also be present during PCR amplification or some other amplification event. At the target detection phase of the PCR cycle, the free-floating probe will leave the probe attached to the bead and will hybridize to the target sequence. The probe attached to the bead will be designed such that it exhibits less favorable binding as well as a lower melting temperature with the free-floating probe, compared to the free-floating probe with the target sequence. As the target sequence increases in concentration, as the PCR reaction continues, a significant increase in signal associated with the beads may be observed. The same effect of a measurable increase in signal may be obtained by a similar method of designing the probe that is attached to the bead to exhibit favorable binding of the target sequence compared to the binding kinetics of the target sequence with the free-floating probe. Differences in binding kinetics may be obtained by designing the free-floating and the fixed probe to be of differing lengths with respect to one another, or by inserting a base or more than one base on one of the probes that is a mismatch with respect to the sequence on the other probe but not with respect to the target sequence.

4. Incorporated Quenching Molecules

Figure 8:
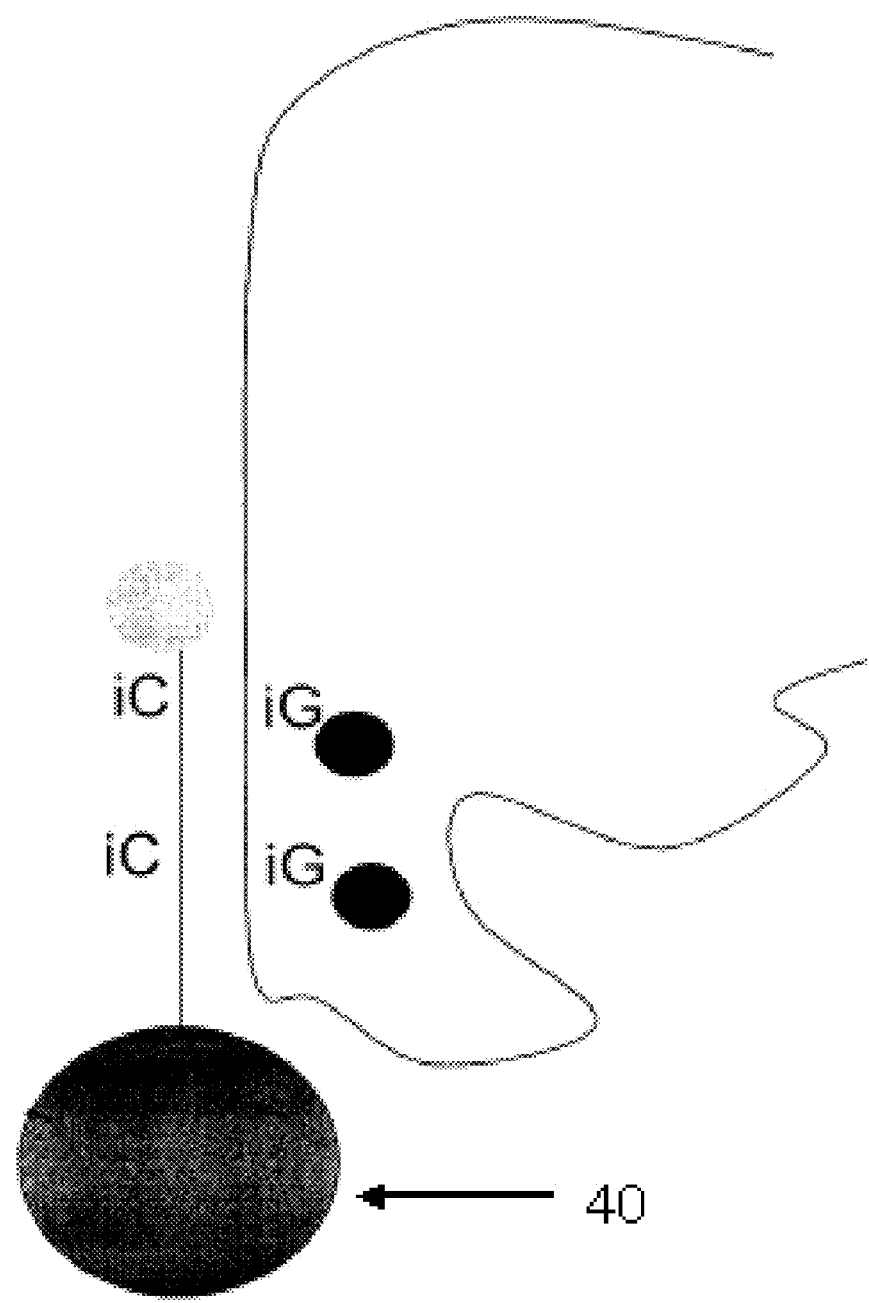
FIG. 8 illustrates a detection chemistry in which quenching molecules are incorporated into a newly synthesized DNA strand and a complementary probe is labeled with a fluorochrome attached to the surface of a bead.

FIG. 8 illustrates an example in which quenching molecules are incorporated into a newly synthesized DNA strand by pre-coupling nucleotides to quenching molecules. This the pre-coupled nucleotide/quencher will be available in the PCR reaction mix and will be incorporated into the amplification products. A complementary probe labeled with a fluorochrome attached to the surface of the bead 40 will result in a system in which fluorescent signal decreases as more and more of the target oligonucleotides sequence is produced. For example, one could combine in a chamber a sample comprising the plurality of nucleic acid targets, a plurality of primer pairs for priming amplification of the plurality of nucleic acid targets, a mixture of dNTPs in which a portion of the dNTPs are coupled to quencher molecules, and a plurality of fluorescently labeled probes complementary to the plurality of nucleic acid targets, wherein the probes are immobilized on a plurality of encoded magnetic beads such that the identity of each probe is known from the encoded magnetic bead on which it is immobilized. An amplification cycle is performed to form amplification products for each of the plurality of nucleic acid targets amplified with the plurality of primer pairs. Because a portion of the dNTPs in the amplification reaction are coupled to quencher molecules, the amplification products will incorporate these quencher molecules. The amplification products are then hybridized to the probes immobilized on the encoded magnetic beads, and a magnetic field is applied to a surface of the chamber to draw the encoded magnetic beads and the amplification products hybridized to the probes immobilized on the encoded magnetic beads to the surface of the chamber. Signals from the encoded magnetic beads and signals from the labeled probes are then detected. Because the amplification products incorporate quencher molecules, the fluorescent signal from the probes decreases as more and more of the amplification product is produced. The magnetic field may be removed from the surface of the chamber prior to performing a further amplification cycle. The amplification and detection may be repeated the desired number of times to obtain real-time quantitative data on the reaction.

5. Direct Hybridization

PCR may be performed wherein the primers used to form amplified sequences or amplicons are labeled with a fluorochrome (e.g., Cy3) or other substance that allows for detection. Labeling may be at, for example, the 5-prime end of the primer. Using primers that are labeled allows formation of labeled amplicons. The amplified nucleic acid sequences that are labeled may hybridize to and be captured by oligonucleotide probes that are coupled to the distinguishable particles. No current, commercial real-time PCR methods employ the use of direct hybridization methods.

Figure 11:
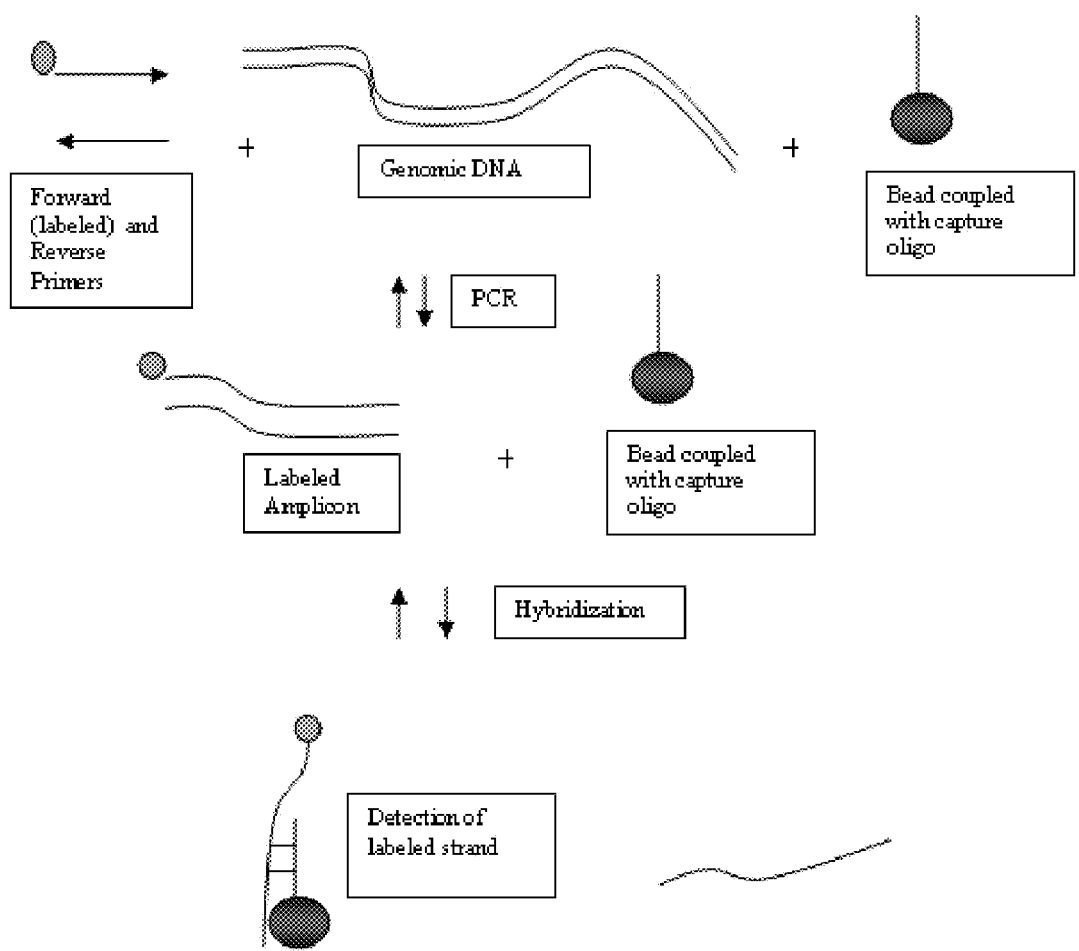
FIG. 11 illustrates a direct hybridization detection chemistry in which one primer of a primer pair is labeled at its 5' end with a reporter molecule.
Figure 12:
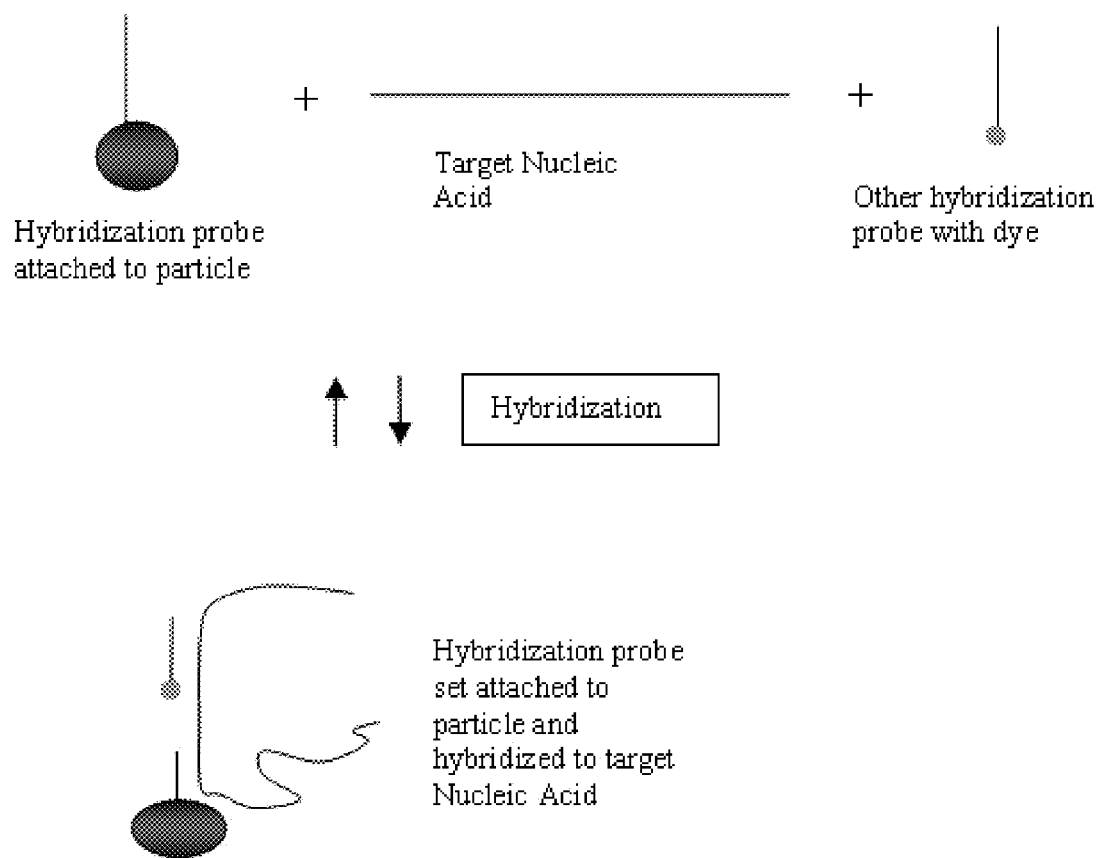
FIG. 12 illustrates a two probe detection chemistry.

An embodiment using a direct hybridization approach is illustrated in FIG. 11. As shown in FIG. 11, one primer of a primer pair is labeled at its 5' end with a reporter molecule such as the fluorophore Cy3. The primer pair amplifies a target sequence from the sample DNA present in the PCR to form a labeled amplicon. Also present in the PCR is a magnetic, encoded bead coupled to a probe that is complementary to the labeled strand of the amplicon. The 3' end of the immobilized probe may be blocked (with a phosphate group or a 3' inverted dT, for example) to prevent the polymerase extension of the probe. After the desired number of PCR cycles, a magnetic field is applied to the chamber to pull the magnetic, encoded beads to a surface of the chamber for detection. This step is performed under hybridization conditions such that labeled amplicons will hybridize to their complementary probes and as such, will be also be pulled to a surface of the chamber. The presence of the labeled amplicons is detected by the detection of the label (e.g. a fluorescent signal from a Cy3 label) at the surface of chamber. Although, the FIG. 11 illustrates a single-plex reaction, it is to be understood that this method can be applied to multiplex PCR reactions as well. The encoded beads, the labels on the amplicons, and combinations thereof, can be used to distinguish large numbers of different amplicons in the same reaction.

6. Tagged Primers

In another embodiment, the present invention provides a method of amplifying and detecting a plurality of nucleic acid targets in a sample comprising combining in a chamber a sample comprising the plurality of nucleic acid targets; a plurality of primer pairs for priming amplification of the plurality of nucleic acid targets, wherein each primer pair comprises a first primer comprising a target specific sequence, a tag sequence 5' of the target specific sequence, and a blocker between the target specific sequence and the tag sequence, and a second primer comprising a target specific sequence; a labeling agent; and a plurality of probes (anti-tags) complementary to the tag sequences of the plurality of primer pairs, wherein the probes are immobilized on a plurality of encoded magnetic beads such that the identity of each probe is known from the encoded magnetic bead on which it is immobilized. An amplification cycle is performed to form tagged and labeled amplification products for each of the plurality of nucleic acid targets amplified with the plurality of primer pairs. The tagged and labeled amplification products are hybridized to the probes immobilized on the encoded magnetic beads, and a magnetic field is applied to a surface of the chamber to draw the encoded magnetic beads and the tagged and labeled amplification products hybridized to the probes immobilized on the encoded magnetic beads to the surface of the chamber. Signals from the encoded magnetic beads and signals from the tagged and labeled amplification products are then detected using, for example, an imaging system such as those described herein. The magnetic field may be removed from the surface of the chamber prior to performing a further amplification cycle. The amplification and detection may be repeated the desired number of times to obtain real-time quantitative data on the reaction. In certain aspects, the labeling agent may be a reporter molecule attached to the second primer of the primer pair. In other aspects, the labeling agent may be an intercalating dye.

As mentioned above, complementary tag sequences (i.e., tags and anti-tags) may be used in the primers and probes. A number of approaches have been developed that involve the use of oligonucleotide tags attached to a solid support that can be used to specifically hybridize to the tag complements that are coupled to primers, probe sequences, target sequences, etc. The proper selection of non-hybridizing tag and anti-tag sequences is useful in assays, particularly assays in a highly parallel hybridization environment, that require stringent non-cross hybridizing behavior.

Certain thermodynamic properties of forming nucleic acid hybrids are considered in the design of tag and anti-tag sequences. The temperature at which oligonucleotides form duplexes with their complementary sequences known as the $T_m$ (the temperature at which 50% of the nucleic acid duplex is dissociated) varies according to a number of sequence dependent properties including the hydrogen bonding energies of the canonical pairs A-T and G-C (reflected in GC or base composition), stacking free energy and, to a lesser extent, nearest neighbor interactions. These energies vary widely among oligonucleotides that are typically used in hybridization assays. For example, hybridization of two probe sequences composed of 24 nucleotides, one with a 40% GC content and the other with a 60% GC content, with its complementary target under standard conditions theoretically may have a 10° C. difference in melting temperature (Mueller et al., 1993). Problems in hybridization occur when the hybrids are allowed to form under hybridization conditions that include a single hybridization temperature that is not optimal for correct hybridization of all oligonucleotide sequences of a set. Mismatch hybridization of non-complementary probes can occur, forming duplexes with measurable mismatch stability (Santalucia et al., 1999). Mismatching of duplexes in a particular set of oligonucleotides can occur under hybridization conditions where the mismatch results in a decrease in duplex stability that results in a higher $T_m$ than the least stable correct duplex of that particular set. For example, if hybridization is carried out under conditions that favor the AT-rich perfect match duplex sequence, the possibility exists for hybridizing a GC-rich duplex sequence that contains a mismatched base having a melting temperature that is still above the correctly formed AT-rich duplex. Therefore, design of families of oligonucleotide sequences that can be used in multiplexed hybridization reactions must include consideration for the thermodynamic properties of oligonucleotides and duplex formation that will reduce or eliminate cross hybridization behavior within the designed oligonucleotide set.

There are a number of different approaches for selecting tag and anti-tag sequences for use in multiplexed hybridization assays. The selection of sequences that can be used as zip codes or tags in an addressable array has been described in the patent literature in an approach taken by Brenner and co-workers (U.S. Pat. No. 5,654,413, incorporated herein by reference). Chetverin et al (WO 93/17126, U.S. Pat. Nos. 6,103,463 and 6,322,971, incorporated herein by reference) discloses sectioned, binary oligonucleotide arrays to sort and survey nucleic acids. These arrays have a constant nucleotide sequence attached to an adjacent variable nucleotide sequence, both bound to a solid support by a covalent linking moiety. Parameters used in the design of tags based on subunits are discussed in Barany et al. (WO 9731256, incorporated herein by reference). A multiplex sequencing method has been described in U.S. Pat. No. 4,942,124, incorporated herein by reference. This method uses at least two vectors that differ from each other at a tag sequence.

U.S. Pat. No. 7,226,737, incorporated herein by reference, describes a set of 210 non-cross hybridizing tags and anti-tags. U.S. Published Application No. 2005/0191625, incorporated herein by reference, discloses a family of 1168 tag sequences with a demonstrated ability to correctly hybridize to their complementary sequences with minimal cross hybridization. U.S. Application No. 60/984,982, incorporated herein by reference, describes the use of tags, anti-tags, and capture complexes in the amplification of nucleic acid sequences.

A population of oligonucleotide tag or anti-tag sequences may be conjugated to a population of primers or other polynucleotide sequences in several different ways including, but not limited to, direct chemical synthesis, chemical coupling, ligation, amplification, and the like. Sequence tags that have been synthesized with target specific primer sequences can be used for enzymatic extension of the primer on the target for example in PCR amplification. A population of oligonucleotide tag or anti-tag sequences may be conjugated to a solid support by, for example, surface chemistries on the surface of the support.

As discussed above, one primer of a primer pair used in an amplification reaction comprises a tag sequence. Following the initial extension of the primer comprising the tag sequence, the tagged extension product may serve as a template for the other primer of the primer pair. It would be undesirable, however, for the extension on such a template to proceed through the tag region as this could interfere with the hybridization of the tag sequence with the anti-tag sequence of the probe. Accordingly, a blocker may be positioned between the target specific sequence and the tag sequence of the primer. Blocker moieties prevent the polymerase from extending into the tag sequence region, which allows the tag sequence to remain single-stranded during amplification and therefore free to hybridize to its complementary anti-tag sequence in the capture complex.

A blocker moiety refers to any moiety that when linked (e.g., covalently linked) between a first nucleotide sequence and a second nucleotide sequence is effective to inhibit and preferably prevent extension of either the first or second nucleotide sequence but not both the first and second nucleotide sequence. There are a number of molecules that may be used as blocker moieties. Non-limiting examples of blocker moieties include C6-20 straight chain alkylenes and iSp18 (which is an 18-atom hexa-ethyleneglycol). Blocker moieties may include, for example, at least one deoxy ribofuranosyl naphthalene or ribofuranosyl naphthalene moiety, which may be linked to the adjacent nucleotides via a 3'-furanosyl linkage or preferably via a 2'-furanosyl linkage. A blocker moiety may be an oligonucleotide sequence that is in the opposite orientation as the target specific sequence. Accordingly, in certain aspects of the invention a primer's tag sequence may be both the tag and the blocker, where the target specific sequence is in the 5' to 3' orientation but the tag sequence is in the 3' to 5' orientation. In this orientation the tag sequence is not extendable by the polymerase enzyme. Various blocker moieties and their use are described in U.S. Pat. No. 5,525,494, which is incorporated herein by reference.

If a blocker moiety is not used, steps may be taken to permit the hybridization of the tag sequence with the anti-tag sequence. For example, an anti-tagged primer may be substituted for the tagged and blocked primer in the amplification. In which case, the polymerase is allowed to extend into the anti-tag sequence region, creating the complementary tag sequence. The double-stranded amplification product which contains an anti-tag/tag region is then denatured prior to hybridization to the anti-tag coupled to the solid substrate.

7. Primers Attached to Particles

In certain embodiments of the invention, primers that are themselves attached to the surface of the magnetically responsive particle may be used. In such embodiments, hybridization probes attached to the beads would not be required to capture the amplicons since the amplicons would be synthesized on the beads. Typically, only one primer of each primer pair would be attached to the particle. The other primer of the primer pair would be "free floating." Such primers may also exhibit properties that allow them to be spectrally distinguishable upon extension, such as with primers that also act as molecular beacons, whereupon a change in signal is observed upon extension of the primer which changes the proximity of a fluorophore and quencher. Other detection chemistries, such as labeling the free-floating primer, incorporating labeled dNTPs into the amplicon, or using DNA intercalating agents, may also be used with these embodiments.

8. Hydrolysis Probes

Another method of target nucleic acid detection takes advantage of the exonuclease activity of some polymerases. In this embodiment, a fluorophore and quencher pair, or a FRET pair may be modifications of a single probe that is attached to a particle (e.g., a bead). One of these fluorochromes may also be attached to the surface of the magnetic bead, with the other fluorochrome being attached to the probe which is affixed to the surface of the particle, such that both fluorochromes interact by virtue of their close spatial proximity to one another. Upon hybridization of the target sequence to the probe, another primer is located downstream of the probe such that upon extension of the primer, the quenching moiety (or fluorescent moiety) is cleaved, yielding a measurable change in signal.

9. SimpleProbes®

Other embodiments may incorporate the use of SimpleProbes® or probes that are equivalent to SimpleProbes®, which are attached to beads for the purpose of viewing data in real-time. These probes are described in U.S. Pat. No. 6,635,427. SimpleProbes® may be attached to superparamagnetic microspheres using an amino modified C12 linker or by some other linker, or another covalent binding interaction. By attaching these probes to beads, the beads may be present during the PCR reaction, such that by binding to the intended target sequences, a double-stranded product is formed, allowing detection and analysis of the nucleic acid sequences in a highly multiplexed real-time PCR format.

10. Immuno-PCR

Immuno-PCR may be used to detect an antigen, cell, endospore, or any other molecule or protein of interest that can be detected by an antibody wherein said antibody is linked to a nucleic acid sequence. Existing methods of immuno-PCR are disclosed in U.S. Pat. No. 5,665,539; Sano, T. et al., Science, 258:120-122 (1992); and Sims, P W et al., Anal Biochem. 281:230-232 (2000), each of which is incorporated by reference. Existing methods, however, are limited in multiplexing ability to detect Immuno-PCR in real-time. In one embodiment, the present invention provides a method that can greatly increases the multiplexing ability to detect Immuno-PCR in real-time by first linking capture antibodies or aptamers to a particle that is magnetic (e.g., superparamagnetic) in nature, wherein the particle is able to react and bind to the target molecule of interest. This particle need not be encoded to be spectrally identifiable. After reaction occurs, or during the reaction, or prior to the reaction, the magnetic particles, which can be nanoparticles or microparticles, may be brought into the detection and amplification chamber. The particles, which are linked to the capture antibodies or aptamers, may be drawn to the surface of the chamber by applying a magnetic field. These particles and the molecules bound or otherwise attached thereto, may undergo a washing procedure, which may include flowing a volume of aqueous solution over the particles, which are held in place by magnetic forces, washing away excess target molecule if need be.

A detection antibody or detection aptamer may be introduced into the reaction chamber and allowed to react and bind to the target molecule, which is also bound by the capture antibody or aptamer, which is in turn linked to the magnetic particles. The detection antibody or detection aptamer is linked to a nucleic acid sequence, which is capable of forming an amplifiable nucleic acid product. The detection antibody need not be introduced while in the detection chamber which is capable of application of a magnetic field, but may be introduced in a separate reaction vessel, and then subsequently introduced into the reaction vessel which is capable of application of a magnetic field. The detection antibody need not be introduced with the target molecule or the target/capture/particle complex prior to a wash procedure. Once the target/capture/particle complex or target/capture/particle/detection complex (capture sandwich complex) is introduced into the detection chamber which is capable of application of a magnetic field, this complex may be drawn to the surface of the chamber, if the particles have not already been drawn to the surface of the chamber in any number of various derivations of methods of forming or washing the target/capture/particle complex, or any parts thereof which have not been fully complexed. Once drawn to the surface of the chamber, this complex may be washed by any number of reagents or buffers or aqueous solutions known in the art for accomplishing such. Buffers that may commonly be used may include but are not limited by using PBS, BSA, PBS/BSA, water, PCR buffer, etc. Washing in this instance may improve the assay by removing excess detection antibody or aptamer, which may increase specificity. The capture antibody or capture aptamer, need not be attached to a particle capable of being drawn to a surface if washing is not desired.

The capture sandwich complex may be used in a PCR reaction or real-time PCR reaction wherein encoded magnetic beads are also present. In this embodiment, the capture sandwich complex or plurality of capture sandwich complexes would have been introduced into a detection chamber which is capable of thermal cycling, having been drawn and held to a surface of the chamber by a magnetic field in order to perform a washing procedure. After washing, the encoded beads, which are coupled with nucleic acid probes suitable for nucleic acid target detection would be introduced thereto in a medium also comprising all the reagents and components necessary to perform a Polymerase Chain Reaction or other method of nucleic acid amplification. The solution would also contain any number of reagents necessary for multiplexed detection of real-time PCR as described in other embodiments herein. For example, the plurality of detection antibodies or detection aptamers are linked to nucleic acid sequences which are comprised of different combinations of sequences so as to allow multiplexed detection of the nucleic acid sequences such that detection of such plurality of sequences could be related back to the detection or quantification of the target molecule by virtue of its association with the detection antibody or detection aptamer.

For example, once that capture sandwich complex and PCR reagents as well as encoded magnetic beads have been combined the subsequent methods may include any number of embodiments for multiplexed amplification and detection described herein. For example, In one embodiment, the present invention provides a method of amplifying and detecting a plurality of nucleic acid targets in a sample comprising: (a) combining in a chamber a sample comprising the plurality of nucleic acid targets, a plurality of primer pairs for priming amplification of the plurality of nucleic acid targets, a labeling agent, and a plurality of probes complementary to the plurality of nucleic acid targets, wherein the probes are immobilized on a plurality of encoded magnetic beads such that the identity of each probe is known from the encoded magnetic bead on which it is immobilized; (b) performing an amplification cycle to form labeled amplification products for each of the plurality of nucleic acid targets amplified with the plurality of primer pairs; (c) hybridizing the labeled amplification products to the probes immobilized on the encoded magnetic beads; (d) applying a magnetic field to a surface of the chamber to draw the encoded magnetic beads and the labeled amplification products hybridized to the probes immobilized on the encoded magnetic beads to the surface of the chamber; (e) detecting the encoded magnetic beads and the labeled amplification products; (f) removing the magnetic field from the surface of the chamber prior to performing a further amplification cycle; and (g) repeating steps (b) through (f) at least once; wherein the plurality of nucleic acid targets in the sample are amplified and detected. In certain aspects of the invention, steps (b) through (f) are repeated between 10 to 40 times.

11. Nucleic Acid Analogs

The nucleic acids used in the methods disclosed herein may include nucleotide isomers or base analogs such as "Locked Nucleic Acids" or others. A nucleic acid sequence may comprise, or be composed entirely of, an analog of a naturally occurring nucleotide. Nucleotide analogs are well known in the art. A non-limiting example is a "peptide nucleic acid," also known as a "PNA," "peptide-based nucleic acid analog," or "PENAM," described in U.S. Pat. Nos. 5,786,461, 5,891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Another non-limiting example is a locked nucleic acid or "LNA." An LNA monomer is a bi-cyclic compound that is structurally similar to RNA nucleosides. LNAs have a furanose conformation that is restricted by a methylene linker that connects the 2'-O position to the 4'-C position, as described in Koshkin et al., 1998a and 1998b and Wahlestedt et al., 2000.

Yet another non-limiting example is a "polyether nucleic acid," described in U.S. Pat. No. 5,908,845, incorporated herein by reference. In a polyether nucleic acid, one or more nucleobases are linked to chiral carbon atoms in a polyether backbone.

12. Hybridization

As used herein, "hybridization," "hybridizes" or "capable of hybridizing" is understood to mean the forming of a double or triple stranded molecule or a molecule with partial double or triple stranded nature. The term "anneal" as used herein is synonymous with "hybridize." The term "hybridization," "hybridizes" or "capable of hybridizing" encompasses the terms "stringent conditions" or "high stringency" and the terms "low stringency" or "low stringency conditions."

As used herein "stringent conditions" or "high stringency" are those conditions that allow hybridization between or within one or more nucleic acid strands containing complementary sequences, but preclude hybridization of non-complementary sequences. Such conditions are well known to those of ordinary skill in the art, and are preferred for applications requiring high selectivity. Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acids, the length and nucleobase content of the target sequences, the charge composition of the nucleic acids, and to the presence or concentration of formamide, tetramethylammonium chloride or other solvents in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Non-limiting examples of low stringency conditions include hybridization performed at about 0.15 M to about 0.9 M NaCl at a temperature range of about 20° C. to about 50° C. Of course, it is within the skill of one in the art to further modify the low or high stringency conditions to suite a particular application.

E. Encoded Particles

Although certain embodiments are described herein with respect to encoded microspheres (i.e., beads), it is to be understood that the illumination subsystems, systems, and methods may also be used with other particles such as microparticles, gold or other metal nanoparticles, quantum dots, or nanodots. The particles are preferably super paramagnetic. Examples of microspheres, beads, and particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference herein.

Excitation of dyes or fluorochromes within or on the surface of encoded particles may be accomplished by laser light, diode light, arc lamp, heat, radioactive emission, chemiluminescence, electroluminescence, chemielectroluminescence, or any other method known to those skilled in the art.

In certain embodiments, the present invention is used in conjunction with Luminex® xMAP® and MagPlex™ technologies. The Luminex xMAP technology allows the detection of nucleic acid products immobilized on fluorescently encoded microspheres. By dyeing microspheres with 10 different intensities of each of two spectrally distinct fluorochromes, 100 fluorescently distinct populations of microspheres are produced. These individual populations (sets) can represent individual detection sequences and the magnitude of hybridization on each set can be detected individually. The magnitude of the hybridization reaction is measured using a third reporter, which is typically a third spectrally distinct fluorophore. The reporter molecule signals the extent of the reaction by attaching to the molecules on the microspheres. As both the microspheres and the reporter molecules are labeled, digital signal processing allows the translation of signals into real-time, quantitative data for each reaction. The Luminex technology is described, for example, in U.S. Pat. Nos. 5,736,330, 5,981,180, and 6,057,107, all of which are specifically incorporated by reference. Luminex® MagPlex™ microspheres are superparamagnetic microspheres that are fluorescently encoded using the xMAP® technology discussed above. The microspheres contain surface carboxyl groups for covalent attachment of ligands (or biomolecules).

F. Kits

The present invention also provides kits containing components for use with the amplification and detection methods disclosed herein. Any of the components disclosed here in may be combined in a kit. In certain embodiments the kits comprise a plurality of primer pairs for priming amplification of a plurality of nucleic acid targets, and a plurality of probes complementary to the plurality of nucleic acid targets, wherein the probes are immobilized on a plurality of encoded magnetic beads such that the identity of each probe is known from the encoded magnetic bead on which it is immobilized. In certain embodiments, the kit also comprises a labeling agent. In certain embodiments the kits comprise probes that are not attached to encoded magnetic beads. In some embodiments the kit comprises an imaging chamber, which may be a disposable imaging chamber, for use in an imaging system.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include packaging for containing the various containers in close confinement for commercial sale. Such packaging may include cardboard or injection or blow molded plastic packaging into which the desired vials, bottles, etc. are retained.

When the components of the kit are provided in one or more liquid solutions, the liquid solution may be an aqueous solution, with a sterile aqueous solution being particularly preferred. However, certain components of the kit may be provided as dried powder(s). When reagents and/or components are provided as a dry powder, the powder can be reconstituted by the addition of a suitable solvent. It is envisioned that the solvent may also be provided in another container means.

A kit may also include instructions for employing the kit components. Instructions may include variations that can be implemented.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1. Example 1

The Stability of Magnetic Microspheres Under PCR Cycling Conditions

This study demonstrates the robust stability of the Luminex super paramagnetic microspheres in PCR cycling conditions. It also demonstrates that an amplicon can be captured and detected at various stages of the PCR reaction as the concentration thereof increases. This study also shows that a two-probe system is a viable design for real-time PCR detection using magnetic microspheres. Hybridization probes (US 2001/6174670) also use a two-probe system.

Experimental Design: A two probe system was used to detect the generation of a Factor V gene amplicon while in the presence of magnetic microspheres that were coupled with target specific nucleotide probes. A target specific probe (FV Probe Ano) was attached to bead set 22. This probe was not fluorescently labeled. Another probe was included in the mix, which was not attached to a bead set, but was target specific, and labeled with a Cy3 fluorophore on the 3' end. A second bead (bead set 27), coupled to an oligonucleotide sequence that is not specific to the target, was also added as a negative control.

A PCR cocktail was prepared using the following reagents and concentrations:

|   |   | 1X |
|---|---|---|
| (Invitrogen) | 10X Buffer | 5 μl |
| (Invitrogen) | dNTP (10 mM) | 1 μl |

-continued

| | | 1X |
|---|---|---|
| (Invitrogen) | MgCl$_2$ (50 mM) | 8 µl |
| (IDT DNA) | Primer | 1 µl |
| UCLA #25 | Genomic template | 1 µl |
| (Invitrogen) | Platinum Taq | 0.4 µl |
| (IDT DNA) | Probe B | 0.66 µl |
| 13-60022 | Bead 22 | 3 µl |
| 13-60027 | Bead 27 | 3 µl |
| Ambion | H$_2$O | 27.6 µl |

Primers were used in optimized asymmetric concentrations, wherein the primer amplifying the target sequence (FV Rev) was in a final concentration of 400 nM compared with the forward primer (FV Fwd52), which was in a final concentration of 50 nM in the PCR cocktail. The concentration of magnesium chloride in this reaction was optimized at a higher concentration than normally would be expected from those skilled in the art. Because a heatable detection chamber was not available, a proof-of-concept experiment was set up such that the PCR cocktail was made, excluding genomic template. The cocktail was aliquoted into 16 equal volumes of 48 µL each. Genomic template was added to each of these aliquots and they were removed from the Perkin Elmer 9700 thermal cycler at different cycle numbers of the PCR reaction. Immediately upon removing the aliquots from the thermal cycler, and without any further reagent additions to the individual reactions, the aliquots were placed on a separate heater at 95° C. for 30 seconds and then at 52° C. for 3 minutes. The aliquots were then immediately analyzed on a Luminex 100 instrument without any further modifications. Both Luminex Magplex microsphere sets added were in a concentration of approximately 5000 microspheres per reaction.

The cycling conditions for this reaction were as follows:
Heat Denaturation Step; 95° C. for 5 min.
Cycling Steps (for 43 cycles): 95° C. for 30 s, 45° C. for 45 s, 72° C. for 45 s.

The oligonucleotide sequences used in this study were ordered from IDT and are as follows:

```
Primers:
FY Rev:
                                      (SEQ ID NO: 1)
TGTTATCACACTGGTGCTAAAAAGG FY Fwd 52:
                                      (SEQ ID NO: 2)
ACTACAGTGACGTGG
Probes:
Probe B short:
                                      (SEQ ID NO: 3)
/3Cy3sp/ATAATGGGCATTTCCTTCAAGAGAACAGTA FY Probe Ano:
                                      (SEQ ID NO: 4)
/5AmMC12/TCTGGCTAGAACATGTTAGGTCTCCTGGCT/3InvdT/

AT-29:
                                      (SEQ ID NO: 5)
/5AmMC12/AAAGAAAGGATTTGTAGTAAGATT
```

The Factor V Leiden genomic gene sequence (gi:2769646 and gi:488109) is shown in FIG. 13.

The data in Table 1 shows an increase in signal as the number of cycles in the PCR reaction increases. The data shows an increase in signal for the specific bead set (22), and no significant increase in signal for the non-specific bead set (27). The signal here is shown as Median Fluorescent Intensity (MFI) from the Luminex Analyzer. This MFI was obtained by measuring the reporter signal from approximately 100 individually coupled magnetic beads and calculating the median.

TABLE 1

| Cycle # | MFI for Bead 22 | MFI for Bead 27 |
|---|---|---|
| 0 | 5 | 5.5 |
| 3 | 7 | 4 |
| 6 | 13 | 8 |
| 9 | 10 | 10.5 |
| 12 | 11 | 8 |
| 15 | 7 | 3 |
| 18 | 11 | 11.5 |
| 21 | 19 | 8 |
| 24 | 27 | 15.5 |
| 27 | 35.5 | 12 |
| 30 | 45 | 11 |
| 33 | 48.5 | 8 |
| 36 | 47 | 13.5 |
| 39 | 47 | 16.5 |
| 43 | 47 | 14 |
| 43 | 49 | 11.5 |

Figure 14:
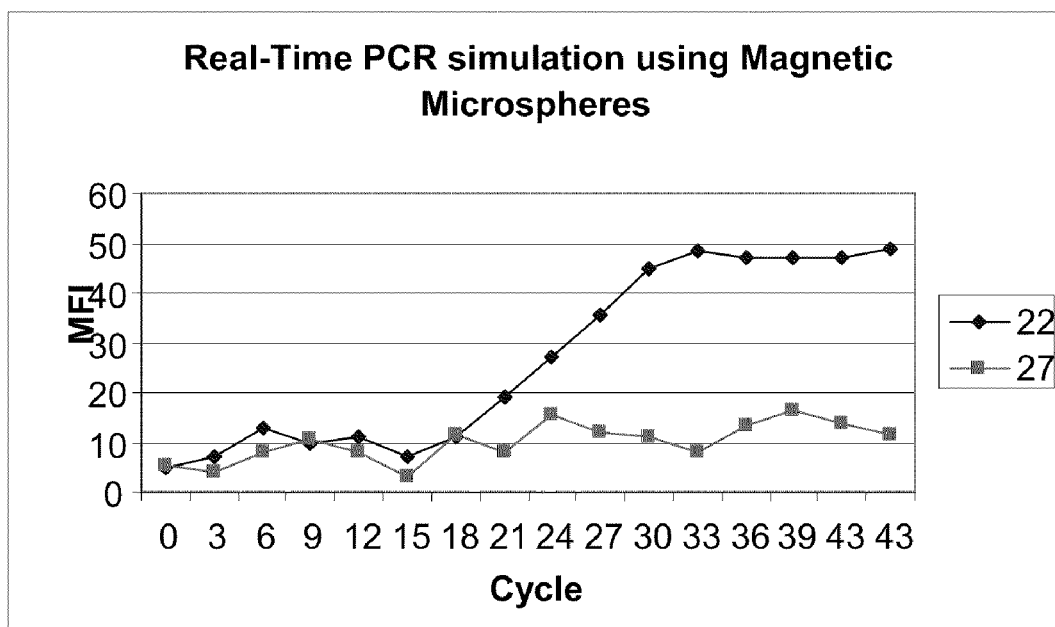
FIG. 14 is a graph of Median Fluorescent Intensity (MFI) (y-axis) and cycle number (x-axis) during PCR.

The data in Table 1 is graphically represented in FIG. 14. As can be seen in FIG. 14, the shape of the curve from bead set 22 is the shape that one would expect from a typical real-time PCR reaction. This curve displays the baseline, the exponential, and the plateau phases indicative of a PCR reaction.

Beads were coupled to capture probes using the following protocol:

1. Bring a fresh aliquot of −20° C., desiccated Pierce EDC powder to room temperature.
2. Resuspend the amine-substituted oligonucleotide ("probe" or "capture" oligo) to 1 mM (1 nanomole/µL) in dH$_2$O.
3. Resuspend the stock uncoupled Luminex microspheres according to the instructions described in the Product Information Sheet provided with the microspheres.
4. Transfer 5.0×10$^6$ of the stock microspheres to a USA Scientific microcentrifuge tube.
5. Pellet the stock microspheres by microcentrifugation at ≧8000×g for 1-2 minutes.
6. Remove the supernatant and resuspend the pelleted microspheres in 50 µL of 0.1 M MES, pH 4.5 by vortex and sonication for approximately 20 seconds.
7. Prepare a 1:10 dilution of the 1 mM capture oligo in dH$_2$O (0.1 nanomole/µL).
8. Add 2 µL (0.2 nanomole) of the 1:10 diluted capture oligo to the resuspended microspheres and mix by vortex.
9. Prepare a fresh solution of 10 mg/mL EDC in dH$_2$O. (Note: Return the EDC powder to desiccant to re-use for the second EDC addition.)
10. One by one for each coupling reaction, add 2.5 µL of fresh 10 mg/mL EDC to the microspheres (25 µg or ≅[0.5 µg/µL]$_{final}$) and mix by vortex.
11. Incubate for 30 minutes at room temperature in the dark.
12. Prepare a second fresh solution of 10 mg/mL EDC in dH$_2$O. (Note: The aliquot of EDC powder should now be discarded.)
13. One by one for each coupling reaction, add 2.5 µL of fresh 10 mg/mL EDC to the microspheres and mix by vortex.
14. Incubate for 30 minutes at room temperature in the dark.
15. Add 1.0 mL of 0.02% Tween-20 to the coupled microspheres.

16. Pellet the coupled microspheres by microcentrifugation at ≧8000×g for 1-2 minutes.

17. Remove the supernatant and resuspend the coupled microspheres in 1.0 mL of 0.1% SDS by vortex.

18. Pellet the coupled microspheres by microcentrifugation at ≧8000×g for 1-2 minutes.

19. Remove the supernatant and resuspend the coupled microspheres in 100 μL of TE, pH 8.0 by vortex and sonication for approximately 20 seconds.

20. Enumerate the coupled microspheres by hemacytometer:
   a. Dilute the resuspended, coupled microspheres 1:100 in dH$_2$O.
   b. Mix thoroughly by vortex.
   c. Transfer 10 μL to the hemacytometer.
   d. Count the microspheres within the 4 large corners of the hemacytometer grid.
   e. Microspheres/μL=(Sum of microspheres in 4 large corners)×2.5×100 (dilution factor).
   f. Note: maximum is 50,000 microspheres/μL.

21. Store coupled microspheres refrigerated at 2-8° C. in the dark.

2. Example 2

Amplification Detection Using Tagged Primers

The following example demonstrates that a nucleic acid amplification signal can be measured in real-time using the tagged primer method. This example also demonstrates that these measurements can be performed using a imaging system comprising a quartz imaging chamber and a magnet that can be moved adjacent to the quartz imaging chamber to magnetically pull the superparamagnetic particles to a two dimensional surface of the chamber opposite a charge coupled device (CCD) detector (see e.g., FIGS. 1 and 2) in the presence of, and without modification to, the Polymerase Chain Reaction solution, and that the measurements thereof are comparable to the Luminex 200 system. The imaging system comprising the quartz chamber and magnet may be considered a "static" imaging system since the detector takes an image of the particles and any molecules bound to them while they are immobilized on the surface of the chamber by the magnetic field. In contrast, the Luminex 200 system may be considered a "flow" system since the particles are not immobilized during detection.

MTHFR Exon 7 gene sequence. Two Luminex MagPlex microsphere sets (Bead sets) were included in the PCR cocktail, during the PCR reaction. The probe attached to Bead set 43 was complementary to the 5' tag sequence on the primer LUA-MEU-TF, whereas the probe coupled to Bead set 12 was not complementary to the tag sequence of the primer in this reaction and thus served as a negative control. Both Luminex Magplex microsphere sets added were in a concentration of approximately 5000 microspheres per reaction.

A PCR cocktail was prepared using the following concentrations and reagents:

| | 1x vol. μL | |
|---|---|---|
| Master Mix | 25 | HotStar TAQ Plus Master Mix 2X, Qiagen |
| H$_2$O | 21 | RNASE FREE Water, Qiagen |
| Primer | 1 | IDT |
| Template | 1 | Purified Human DNA Sample from UCLA |
| Beads | 2 | Luminex Magplex microspheres |
| total | 50 | |

The cycling conditions for this reaction were as follows:
Heat Denaturation Step; 95° C. for 5 min.
Cycling Steps (for 36 cycles): 94° C. for 30 s, 55° C. for 30 s, 72° C. for 30 s.

The oligonucleotide sequences used in this experiment were ordered from IDT and were as follows:

```
Primers:
LUA-MEU-TF:
                                       (SEQ ID NO: 16)
CAAACAAACATTCAAATATCAATC/iSp18/CAAGGAGGAGCTGCTGAAG
ATG LUA-MED-TF:
                                       (SEQ ID NO: 17)
/5Cy3/CACTTTGTGACCATTCCGGTTTG Probes:
Bead Set 43: Bead ME tf:
                                       (SEQ ID NO: 18)
/5AmMC12/GATTGATATTTGAATGTTTGTTTG Bead Set 12: W12822:
                                       (SEQ ID NO: 19)
/5AmMC12/ CAA CAG TGG AGG AAA GCC/3InvdT/
```

Target sequence:

```
MTHFR Exon 7 (MRE7)    [gi: 17444393]     112 bp
                                       (SEQ ID NO: 20)
GGAGGAGCTGCTGAAGATGTGGGGGGAGGAGCTCACCAGTGAAGAAAGTGTCTTTGAAGTCTTTGTTCTTC
CTCCTCGACGACTTCTACACCCCCCTCCTCGAGTGGTCACTTCTTCACAGAAACTTCAGAAACA
AGAATACCTCTCGGGAGAACCAAACCGGAATGGTCACAAAGTGA
```

Experimental Design:

In this design, two primers were used, wherein one of the primers was modified with a Cy3 fluorophore at its 5' end. The other primer was modified with a Carbon 18 spacer positioned between the target specific region and a tag sequence complimentary to a specific probe (anti-tag) sequence attached to a superparamagnetic microsphere. In this case the primer LUA-MEU had a tag sequence on the 5' side of the C18 spacer (iSp18-IDT) that was complimentary to the Bead ME tf probe sequence that was coupled to bead set 43. In this study the primer sets were designed to amplify a region of the In this experiment the primer concentrations and Magnesium Chloride concentrations did not need to be optimized. This was due to the nature of the design of the amplification primers wherein the amplified product contains a single stranded overhang corresponding to the tag sequence. The C18 spacer blocks extension by the polymerase, such that the tag sequence complimentary to the probe on bead set 43 cannot serve as a template for second strand synthesis. Accordingly, the single stranded tag sequence on the 5' end of the amplification product was able to hybridize to the probe without competition from a reverse complimentary strand as occurs in the direct hybridization model.

In this study a PCR cocktail was made without template to be more than enough volume to be aliquoted into 32 separate PCR tubes at a volume of 50 uL each. This PCR cocktail included the two sets of Luminex MagPlex microspheres. Once mixed and aliquoted, 16 of the PCR reactions were mixed with genomic DNA, and 16 tubes were kept as no template (nt) reactions to serve as negative PCR controls. 8 positive samples and 8 negative samples were analyzed using the Luminex LX200 instrument. Additionally, 8 positive and 8 negative samples were analyzed using the "static" imaging instrument described above. In each case of a set of 8 samples, each sample was removed from the thermal cycler at various stages of the PCR reaction. These samples were removed from the thermal cycler at the following cycles: 0, 5, 10, 15, 20, 25, 30, 35. The reactions were stored temporarily at room temperature in the dark until the thermal cycling was completed.

Then the samples were placed on a 95° C. heater for 1 minute followed by 10 minutes at 37° C.

These samples were also run on a Reliant Gel System Gel Cat. No. 54929 to check for amplification specificity.

Data obtained from the "static" imaging instrument are included in Table 2:

TABLE 2

|  | Bead Regions | | | | | |
|---|---|---|---|---|---|---|
|  | 43 Count | 12 Count | 43 RP1 Median | 12 RP1 Median | Well | Cycles |
| No Template | 111 | 177 | 234 | 232 | A-1 | 0 |
| Reactions | 196 | 130 | 239 | 237 | B-1 | 5 |
|  | 150 | 109 | 229 | 225 | C-1 | 10 |
|  | 177 | 135 | 233 | 235 | D-1 | 15 |
|  | 194 | 123 | 248 | 248 | E-1 | 20 |
|  | 181 | 128 | 251 | 246 | F-1 | 25 |
|  | 207 | 125 | 245 | 250 | G-1 | 30 |
|  | 161 | 129 | 254 | 253 | H-1 | 35 |
| Genomic | 201 | 115 | 241 | 239 | A-2 | 0 |
| DNA added | 160 | 112 | 242 | 239 | B-2 | 5 |
|  | 173 | 117 | 245 | 245 | C-2 | 10 |
|  | 162 | 89 | 244 | 242 | D-2 | 15 |
|  | 164 | 114 | 241 | 242 | E-2 | 20 |
|  | 175 | 138 | 246 | 243 | F-2 | 25 |
|  | 199 | 124 | 265 | 228 | G-2 | 30 |
|  | 167 | 118 | 306 | 223 | H-2 | 35 |

For the "static" imaging instrument, each sample was dispensed into the quartz imaging chamber and the encoded magnetic beads were pulled to the back of the chamber and held in place during analysis. This data displays the representative median values from the reporter wavelengths. Both bead sets were able to classify using the classification wavelengths without any problem. Notice the increase in signal at cycles 30 and 35 from bead set 43. This increase in signal is correlative to the gel data with regard to amplification size and intensity.

Data obtained from the Luminex 200 Instrument (Table 3) using an identical sample set up as the samples that were analyzed on the "static" imaging instrument (Table 2).

TABLE 3

| Data Type: Median | | | | | | |
|---|---|---|---|---|---|---|
|  |  | Location | Cycles | Bead 12 median | Bead 43 median | Total Events |
| No Template | 1 | (1, A1) | 0 | 5 | 4 | 253 |
| Reactions | 2 | (1, B1) | 5 | 0 | 6.5 | 230 |
|  | 3 | (1, C1) | 10 | 3.5 | 6 | 243 |
|  | 4 | (1, D1) | 15 | 5 | 3.5 | 212 |
|  | 5 | (1, E1) | 20 | 3 | 4 | 233 |
|  | 6 | (1, F1) | 25 | 0 | 2 | 245 |
|  | 7 | (1, G1) | 30 | 5.5 | 8 | 261 |
|  | 8 | (1, H1) | 35 | 4.5 | 0 | 268 |
| Genomic | 9 | (1, A2) | 0 | 4 | 4.5 | 240 |
| DNA added | 10 | (1, B2) | 5 | 4.5 | 4 | 239 |
|  | 11 | (1, C2) | 10 | 5 | 5 | 218 |
|  | 12 | (1, D2) | 15 | 6.5 | 7 | 217 |
|  | 13 | (1, E2) | 20 | 4.5 | 0 | 239 |
|  | 14 | (1, F2) | 25 | 6.5 | 7 | 228 |
|  | 15 | (1, G2) | 30 | 0.5 | 26 | 232 |
|  | 16 | (1, H2) | 35 | 4 | 51 | 224 |

The data correlated with the data from the gel with regard to amplification size and intensity. A similar pattern of signal increase was also shown using the "static" imaging system format.

3. Example 3

Multiplex of 8

In this example, the Direct Hybridization method was used with 8 primer sets and 14 bead sets. An excess of bead sets were used to show that the amplification products do not non-specifically hybridize to bead sets containing unrelated probes.

A PCR cocktail was made including the following reagents:

TABLE 4

|  |  | 1x vol. µL | 45 |
|---|---|---|---|
| Qiagen hotstart plus 2x | Master Mix | 25 | 1125 |
| H$_2$O Ambion nuclease free | H$_2$O | 17 | 765 |
| 8 plex ordered from IDT | Primer | 1 | 45 |
| Coriell Sample 13033 | Template | 1 | 45 |
| Luminex MagPlex microspheres | Beads | 3 | 135 |
| 50 mM mgCl$_2$ Qiagen |  | 3 | 135 |
|  | total | 50 | 2250 |

This cocktail, including the Luminex MagPlex microspheres with probe sequences attached thereto, was aliquoted into 40 PCR tubes at 50 µL each. Then 20 of the reactions had approximately 100 ng of genomic DNA added to them. These reactions were cycled on a BioRad iCycler thermal cycler. The primers were designed to amplify specific regions of the cystic fibrosis CFTR gene. Primer sequences for each of 8 primer sets used for this reaction are included in Table 5, including the final concentrations in each 50 µL reaction.

TABLE 5

Primer compositions

| Set name | modification | sequence | scale | bp | purification | Final Conc. (nM) |
|---|---|---|---|---|---|---|
| 1 E20U | None | TTG AGA CTA CTG AAC ACT GAA GG (SEQ ID NO: 21) | 100 nmol | 23 | desalt | 75 |
| 1 CE20D | /5Cy3/ | TTC TGG CTA AGT CCT TTT GC (SEQ ID NO: 22) | 100 nmol | 20 | HPLC | 125 |
| 2 E11U | None | TCA GAT TGA GCA TAC TAA AAG TGA C (SEQ ID NO: 23) | 100 nmol | 25 | desalt | 75 |
| 2 CE11D | /5Cy3/ | GAA CTA TAT TGT CTT TCT CTG CAA AC (SEQ ID NO: 24) | 100 nmol | 26 | HPLC | 125 |
| 3 E11U2 | None | AAG TTT GCA GAG AAA GAC AAT ATA G (SEQ ID NO: 25) | 100 nmol | 25 | desalt | 100 |
| 3 CE11D2 | /5Cy3/ | GAA TGA CAT TTA CAG CAA ATG C (SEQ ID NO: 26) | 100 nmol | 22 | HPLC | 200 |
| 4 E4U | None | TTT GTA GGA AGT CAC CAA AGC (SEQ ID NO: 27) | 100 nmol | 21 | desalt | 75 |
| 4 CE4D | /5Cy3/ | GAG CAG TGT CCT CAC AAT AAA GAG (SEQ ID NO: 28) | 100 nmol | 24 | HPLC | 125 |
| 5 CE21U | /5Cy3/ | TGC TAT AGA AAG TAT TTA TTT TTT CTG G (SEQ ID NO: 29) | 100 nmol | 28 | HPLC | 125 |
| 5 E21D | None | AGC CTT ACC TCA TCT GCA AC (SEQ ID NO: 30) | 100 nmol | 20 | desalt | 75 |
| 6 CE7U | /5Cy3/ | GAA CAG AAC TGA AAC TGA CTC G (SEQ ID NO: 31) | 100 nmol | 22 | HPLC | 200 |
| 6 E7D3 | None | CAG GGA AAT TGC CGA GTG (SEQ ID NO: 32) | 100 nmol | 18 | desalt | 100 |
| 7 CC7U | /5Cy3/ | GAC TTG TCA TCT TGA TTT CTG G (SEQ ID NO: 33) | 100 nmol | 22 | HPLC | 125 |
| 7 C7D | None | TTT GGT GCT AGC TGT AAT TGC (SEQ ID NO: 34) | 100 nmol | 21 | desalt | 75 |
| 8 BE9U | /5Cy3/ | TCA CTT CTT GGT ACT CCT GTC C (SEQ ID NO: 35) | 100 nmol | 22 | HPLC | 125 |
| 8 E9D | None | CAA AAG AAC TAC CTT GCC TGC (SEQ ID NO: 36) | 100 nmol | 21 | desalt | 75 |

The cycling conditions for this reaction were as follows:
Heat Denaturation Step: 95° C. for 10 min.
Cycling Steps (for 36 cycles): 94° C. for 30 s, 56° C. for 90 s, 72° C. for 90 s.
Individual PCR samples were removed at various cycles during the PCR reaction. These tubes were removed during the 56° C. step at their respective cycle numbers. Both "no template" and "template positive" samples were removed simultaneously at the following cycle numbers: 5, 8, 12, 16, 20, 24, 28, 30, 36, and 36 again. These samples that were pulled off the thermal cycler were stored in the dark at room temperature until the completion of all 36 cycles. Without any further modifications to the samples regarding addition of reagents, these samples were heated to 95° C. for 1 minute, and then incubated at 44° C. for 15 minutes and then analyzed on a Luminex 200 instrument and on a "static" imaging system as described above. Although a heatable detection chamber was not available at the time, the design of this experiment shows that it is possible to perform this reaction in real-time, if the general procedures described herein are adapted to analysis in a detection chamber capable of thermal cycling.

The bead sets used in the reactions and the probes that were coupled to them are contained in Table 6.

TABLE 6

| Bead Set name | modification | sequence | scale | bp | purification | Target Primer Set |
|---|---|---|---|---|---|---|
| 12 W12822 | /5AmMC12/ /3InvdT/ | CAA CAG TGG AGG AAA GCC (SEQ ID NO: 37) | 100 nmol | 18 | desalt | |

TABLE 6-continued

| Bead Set | name | modification | sequence | scale | bp | purification | Target Primer Set |
|---|---|---|---|---|---|---|---|
| 19 | G1717 | /5AmMC12/ /3InvdT/ | TTG GTA ATA GGA CAT CTC CA (SEQ ID NO: 38) | 100 nmol | 20 | desalt | 2 |
| 18 | R560 | /5AmMC12/ /3InvdT/ | CTT TAG CAA GGT GAA TAA CT (SEQ ID NO: 39) | 100 nmol | 20 | desalt | 3 |
| 20 | R117 | /5AmMC12/ /3InvdT/ | AGG AGG AAC GCT CTA TCG CG (SEQ ID NO: 40) | 100 nmol | 20 | desalt | 4 |
| 22 | N1303 | /5AmMC12/ /3InvdT/ | GGG ATC CAA GTT TTT TCT AA (SEQ ID NO: 41) | 100 nmol | 20 | desalt | 5 |
| 25 | 1078T2 | /5AmMC12/ /3InvdT/ | CAC CAC AAA GAA CCC TGA (SEQ ID NO: 42) | 100 nmol | 18 | desalt | 6 |
| 36 | A455 | /5AmMC12/ /3InvdT/ | CCA GCA ACC GCC AAC AAC TG (SEQ ID NO: 43) | 100 nmol | 20 | desalt | 8 |
| 38 | 3659C2 | /5AmMC12/ /3InvdT/ | TTG ACT TOG TAG GTT TAC (SEQ ID NO: 44) | 100 nmol | 18 | desalt | none |
| 35 | G278952 | /5AmMC12/ /3InvdT/ | TGG AAA GTG AGT ATT CCA TGT C (SEQ ID NO: 45) | 100 nmol | 22 | desalt | none |
| 37 | 2184A7 | /5AmMC12/ /3InvdT/ | GAA ACA AAA AAA CAA TC (SEQ ID NO: 46) | 100 nmol | 17 | desalt | none |
| 39 | G18982 | /5AmMC12/ /3InvdT/ | TAT TTG AAA GGT ATG TTC TTT G (SEQ ID NO: 47) | 100 nmol | 22 | desalt | none |
| 42 | G31202 | /5AmMC12/ /3InvdT/ | CTT CAT CCA GGT ATG TAA AAA T (SEQ ID NO: 48) | 100 nmol | 22 | desalt | none |
| 44 | G85 | /5AmMC12/ /3InvdT/ | ATT TGA TGA AGT ATG TAC CTA T (SEQ ID NO: 49) | 100 nmol | 22 | desalt | none |
| 43 | C3849 | /5AmMC12/ /3InvdT/ | GTC TTA CTC GCC ATT TTA AT (SEQ ID NO: 50) | 100 nmol | 20 | desalt | 7 |

The Cystic Fibrosis gene sequences (SEQ ID NO: 8-15) used in this experiment are given in FIG. 15. The results from the reaction were confirmed by analysis on a gel.

Data was collected using a Luminex 200 instrument, while at 44° C. Data collected is represented in Table 7. All template positive samples whose values are distinguishable from the noise are shaded in Table 7. Further optimization techniques known to those skilled in the art may be used to modify the reaction conditions and further improve the signal-to-noise ratio. The bead sets whose MFI values were expected to be target specific to the amplicon rose above the noise toward the latter end of the reaction. The bead sets whose probes were expected to be non-specific or negative did not.

TABLE 7

| Sample | Analyte 12 | Analyte 18 | Analyte 19 | Analyte 20 | Analyte 22 | Analyte 25 | Analyte 35 | Analyte 36 | Analyte 37 | Analyte 38 | Analyte 39 | Analyte 42 | Analyte 43 | Analyte 44 | Total Event |
|---|---|---|---|---|---|---|---|---|---|---|---|---|---|---|---|
| blank | 6 | 0 | 2 | 4 | 2 | 3 | 3 | 2 | 2 | 2 | 4 | 1 | 3 | 3 | 148 |
| 5− | 30 | 22.5 | 28 | 18 | 25 | 22 | 28.5 | 27 | 26 | 18 | 27 | 26 | 31 | 29 | 1892 |
| 5+ | 30 | 34 | 44 | 17 | 34 | 27 | 38 | 43 | 24.5 | 39.5 | 39 | 33 | 29.5 | 37 | 2012 |
| 8− | 30 | 16 | 17 | 20 | 13 | 21 | 23 | 15 | 25.5 | 27 | 29.5 | 22 | 24 | 19.5 | 2069 |
| 8+ | 30.5 | 29.5 | 29.5 | 34 | 25.5 | 25 | 31 | 31 | 25 | 42 | 36.5 | 31 | 24 | 27 | 1905 |
| 12− | 20 | 13.5 | 5 | 16 | 21.5 | 16.5 | 15 | 14 | 18 | 32.5 | 21 | 9.5 | 7 | 22 | 1747 |
| 12+ | 46 | 29 | 21 | 24 | 34 | 47 | 28.5 | 20 | 33.5 | 61.5 | 22 | 41 | 21 | 37 | 2023 |
| 16− | 64 | 39 | 19 | 27.5 | 55 | 29 | 27 | 58 | 41.5 | 62.5 | 68 | 37.5 | 36 | 46 | 1734 |
| 16+ | 52 | 47 | 45 | 21 | 34 | 39.5 | 48 | 28.5 | 39.5 | 46 | 49.5 | 49 | 45 | 34 | 2256 |
| 20− | 32 | 18.5 | 33 | 45.5 | 24 | 23.5 | 26 | 27.5 | 31.5 | 27 | 20 | 28.5 | 33 | 35.5 | 1832 |
| 20+ | 50 | 37 | 32 | 44 | 47.5 | 38 | 24.5 | 40 | 34 | 63 | 64 | 36 | 31.5 | 56.5 | 1806 |
| 24− | 43 | 35 | 39.5 | 32.5 | 29 | 33 | 46.5 | 32 | 24 | 27 | 33.5 | 26 | 20 | 33 | 1789 |
| 24+ | 56 | 34.5 | 27 | 41 | 34 | 25.5 | 14 | 54 | 19 | 14 | 21.5 | 14 | 19 | 14 | 1852 |
| 28− | 23 | 40.5 | 30 | 29.5 | 16.5 | 19 | 21 | 42.5 | 0 | 15 | 25 | 15 | 17 | 24.5 | 2026 |
| 28+ | 78 | 101.5 | 72 | 66.5 | 54 | 78 | 20 | 134 | 19 | 21 | 31.5 | 17 | 37 | 26.5 | 1938 |
| 30− | 46 | 23.5 | 40 | 23 | 35 | 25.5 | 29 | 35 | 6.5 | 17.5 | 34 | 18.5 | 10.5 | 29 | 1867 |
| 30+ | 102 | 120 | 82 | 77 | 107 | 84 | 28 | 110 | 25.5 | 59.5 | 48 | 51.5 | 47.5 | 46 | 1838 |
| 32− | 13 | 13 | 24.5 | 17 | 20.5 | 19.5 | 14 | 28 | 23 | 20 | 10.5 | 25 | 14 | 20.5 | 1673 |
| 32+ | 15.8 | 113 | 116 | 118.5 | 115 | 87 | 35 | 180 | 26 | 43 | 33 | 49 | 80 | 36 | 1844 |
| 36− | 48.5 | 18.5 | 31 | 24 | 17.5 | 34 | 33 | 33 | 20 | 44 | 34 | 41 | 16 | 32.5 | 1757 |
| 36+ | 184 | 120 | 120 | 109.5 | 153 | 83 | 54 | 230 | 31.5 | 36 | 65.5 | 49 | 94 | 43 | 1790 |

Data was collected using the "static" imaging system, while at 44° C. Net data collected using the "static" imaging system is represented in Table 8. All positive samples whose values are distinguishable from the noise are highlighted in Table 8. The raw data from the "static" imaging system that was used to create Table 8 is represented in Table 9. Table 8 was calculated by taking the average MFI from data points of all beads sets with template negative samples for all cycles and subtracting that average from all data points. In the case where the resulting sum of that calculation was negative, all negative numbers were converted to zero. Some of the lower cycle numbers contained spurious results, which can be considered outliers.

TABLE 8

| Cycle | pos/neg | Bead Sets |  |  |  |  |  |  |  |  |  |  |  |  |  |
|---|---|---|---|---|---|---|---|---|---|---|---|---|---|---|---|
|  |  | 12 | 18 | 19 | 20 | 22 | 25 | 35 | 36 | 37 | 38 | 39 | 42 | 43 | 44 |
|  |  | Net RP1 Median |  |  |  |  |  |  |  |  |  |  |  |  |  |
| 36 | − | 0 | 0 | 0 | 0 | 0 | 0 | 0 | 5 | 5 | 2 | 12 | 0 | 0 | 0 |
| 36 | + | 180 | 121 | 121 | 118 | 123 | 78 | 24 | 214 | 16 | 28 | 17 | 16 | 21 | 17 |
| 36 | − | 0 | 0 | 0 | 0 | 0 | 0 | 0 | 0 | 0 | 0 | 0 | 0 | 0 | 0 |
| 36 | + | 214 | 152 | 146 | 133 | 158 | 107 | 39 | 253 | 28 | 42 | 27 | 38 | 109 | 12 |
| 30 | − | 0 | 0 | 0 | 0 | 0 | 0 | 0 | 0 | 0 | 0 | 0 | 0 | 0 | 0 |
| 30 | + | 126 | 154 | 80 | 74 | 130 | 72 | 11 | 208 | 34 | 22 | 25 | 9 | 26 | 11 |
| 28 | − | 0 | 0 | 8 | 0 | 4 | 9 | 29 | 14 | 25 | 22 | 21 | 4 | 16 | 17 |
| 28 | + | 74 | 141 | 40 | 54 | 85 | 66 | 0 | 161 | 13 | 4 | 12 | 17 | 40 | 8 |
| 24 | − | 13 | 34 | 28 | 23 | 34 | 19 | 34 | 41 | 35 | 57 | 33 | 39 | 21 | 33 |
| 24 | + | 93 | 71 | 71 | 63 | 45 | 78 | 54 | 125 | 49 | 74 | 55 | 71 | 53 | 60 |
| 20 | − | 38 | 30 | 52 | 66 | 53 | 62 | 77 | 76 | 56 | 89 | 58 | 64 | 59 | 54 |
| 20 | + | 48 | 53 | 69 | 32 | 28 | 42 | 59 | 71 | 62 | 62 | 82 | 65 | 33 | 57 |
| 16 | − | 9 | 0 | 9 | 0 | 0 | 0 | 7 | 9 | 29 | 11 | 27 | 7 | 9 | 4 |
| 16 | + | 0 | 0 | 4 | 0 | 1 | 0 | 0 | 10 | 26 | 16 | 9 | 12 | 12 | 19 |
| 12 | − | 11 | 7 | 2 | 6 | 0 | 0 | 0 | 7 | 0 | 19 | 23 | 17 | 0 | 15 |
| 12 | + | 36 | 50 | 54 | 61 | 49 | 59 | 57 | 71 | 77 | 67 | 102 | 103 | 92 | 85 |
| 8 | − | 16 | 35 | 51 | 54 | 26 | 29 | 22 | 44 | 38 | 34 | 32 | 32 | 33 | 37 |
| 8 | + | 38 | 46 | 58 | 39 | 51 | 33 | 47 | 46 | 81 | 63 | 69 | 47 | 50 | 54 |
| 5 | − | 16 | 44 | 35 | 34 | 26 | 27 | 49 | 39 | 74 | 78 | 56 | 53 | 50 | 57 |
| 5 | + | 8 | 32 | 23 | 17 | 0 | 8 | 33 | 29 | 25 | 30 | 34 | 22 | 28 | 23 |

The raw data from the "static" imaging system that was used to create Table 8 is represented in Table 9.

TABLE 9

| Cycle | pos/neg | Bead Sets |  |  |  |  |  |  |  |  |  |  |  |  |  |
|---|---|---|---|---|---|---|---|---|---|---|---|---|---|---|---|
|  |  | 12 | 18 | 19 | 20 | 22 | 25 | 35 | 35 | 37 | 38 | 39 | 42 | 43 | 44 |
|  |  | Net RP1 Median |  |  |  |  |  |  |  |  |  |  |  |  |  |
| 36 | + | 562 | 514 | 514 | 531 | 516 | 471 | 417 | 607 | 409 | 421 | 410 | 409 | 484 | 410 |
| 36 | − | 387 | 376 | 392 | 377 | 368 | 375 | 364 | 398 | 398 | 395 | 405 | 373 | 377 | 388 |
| 36 | − | 230 | 241 | 221 | 238 | 230 | 224 | 233 | 232 | 241 | 232 | 222 | 226 | 229 | 237 |
| 36 | + | 607 | 545 | 539 | 526 | 551 | 500 | 432 | 656 | 421 | 435 | 420 | 431 | 502 | 405 |
| 30 | − | 361 | 358 | 368 | 375 | 370 | 362 | 383 | 371 | 367 | 392 | 382 | 385 | 366 | 389 |
| 30 | + | 519 | 547 | 473 | 467 | 523 | 465 | 404 | 599 | 427 | 415 | 418 | 402 | 419 | 404 |
| 28 | − | 389 | 388 | 401 | 381 | 397 | 402 | 422 | 407 | 418 | 415 | 414 | 397 | 409 | 410 |
| 28 | + | 467 | 536 | 433 | 447 | 481 | 459 | 380 | 554 | 406 | 397 | 405 | 410 | 433 | 401 |
| 24 | − | 407 | 427 | 421 | 416 | 427 | 412 | 427 | 434 | 428 | 450 | 426 | 432 | 414 | 426 |
| 24 | + | 486 | 464 | 464 | 456 | 438 | 471 | 447 | 518 | 442 | 467 | 448 | 464 | 446 | 453 |
| 20 | − | 431 | 423 | 445 | 459 | 446 | 455 | 470 | 469 | 449 | 482 | 451 | 457 | 452 | 447 |
| 20 | + | 441 | 446 | 462 | 425 | 421 | 435 | 452 | 464 | 455 | 455 | 475 | 458 | 426 | 450 |
| 16 | − | 402 | 392 | 402 | 392 | 387 | 373 | 400 | 402 | 422 | 404 | 420 | 400 | 402 | 397 |
| 16 | + | 381 | 383 | 397 | 383 | 394 | 388 | 389 | 403 | 419 | 409 | 402 | 405 | 405 | 412 |
| 12 | − | 404 | 400 | 395 | 399 | 388 | 380 | 384 | 400 | 388 | 412 | 416 | 410 | 387 | 408 |
| 12 | + | 429 | 443 | 447 | 454 | 442 | 452 | 450 | 464 | 470 | 460 | 495 | 496 | 485 | 478 |
| 8 | − | 409 | 428 | 444 | 447 | 419 | 422 | 415 | 437 | 431 | 427 | 425 | 425 | 426 | 430 |
| 8 | + | 431 | 439 | 451 | 432 | 444 | 426 | 440 | 439 | 474 | 456 | 462 | 440 | 443 | 447 |
| 5 | − | 409 | 437 | 428 | 427 | 419 | 420 | 442 | 432 | 467 | 471 | 449 | 446 | 443 | 450 |
| 5 | + | 401 | 425 | 416 | 410 | 387 | 401 | 426 | 422 | 418 | 423 | 427 | 415 | 421 | 416 |

\*\*\*

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,942,124
U.S. Pat. No. 4,996,143
U.S. Pat. No. 5,210,015

U.S. Pat. No. 5,432,272
U.S. Pat. No. 5,436,134
U.S. Pat. No. 5,487,972
U.S. Pat. No. 5,525,494
U.S. Pat. No. 5,532,129
U.S. Pat. No. 5,538,848
U.S. Pat. No. 5,539,082
U.S. Pat. No. 5,565,322
U.S. Pat. No. 5,654,413
U.S. Pat. No. 5,656,493
U.S. Pat. No. 5,658,751
U.S. Pat. No. 5,665,539
U.S. Pat. No. 5,714,331
U.S. Pat. No. 5,716,784
U.S. Pat. No. 5,719,262
U.S. Pat. No. 5,736,330
U.S. Pat. No. 5,736,336
U.S. Pat. No. 5,766,855
U.S. Pat. No. 5,773,571
U.S. Pat. No. 5,786,461
U.S. Pat. No. 5,866,336
U.S. Pat. No. 5,891,625
U.S. Pat. No. 5,908,845
U.S. Pat. No. 5,925,517
U.S. Pat. No. 5,981,180
U.S. Pat. No. 5,994,056
U.S. Pat. No. 6,030,787
U.S. Pat. No. 6,046,807
U.S. Pat. No. 6,057,107
U.S. Pat. No. 6,103,463
U.S. Pat. No. 6,139,800
U.S. Pat. No. 6,174,670
U.S. Pat. No. 6,268,222
U.S. Pat. No. 6,322,971
U.S. Pat. No. 6,366,354
U.S. Pat. No. 6,411,904
U.S. Pat. No. 6,449,562
U.S. Pat. No. 6,514,295
U.S. Pat. No. 6,524,793
U.S. Pat. No. 6,528,165
U.S. Pat. No. 6,592,822
U.S. Pat. No. 6,635,427
U.S. Pat. No. 6,939,720
U.S. Pat. No. 7,205,105
U.S. Pat. No. 7,226,737
U.S. Patent Publn. 2000/6103476
U.S. Patent Publn. 2000/6140054
U.S. Patent Publn. 2000/6140496
U.S. Patent Publn. 2000/6150097
U.S. Patent Publn. 2001/6171785
U.S. Patent Publn. 2001/6174670
U.S. Patent Publn. 2001/6174670
U.S. Patent Publn. 2001/6270967
U.S. Patent Publn. 2003/6569627
U.S. Patent Publn. 2003/6617106
U.S. Patent Publn. 2005/0164219
U.S. Patent Publn. 2005/0191625
U.S. Patent Publn. 2005/0233335
U.S. Patent Publn. 2006/0019253
U.S. Patent Publn. 2006/0211028
U.S. Patent Publn. 2006/0211028
U.S. Patent Publn. 2007/0020672
U.S. Patent Publn. 2007/7205105
U.S. patent Ser. No. 11/270,786
U.S. patent Ser. No. 11/534,166
Bengtsson et al., *Nucleic Acids Res.*, 31:e45, 2003.
Bernard et al, *Am. J. Pathol.*, 153:1055-1061, 1998.
Bernard et al, *Anal Biochem.*, 255:101-107, 1998.
Bustin et al., *J. Biomol. Tech.*, 15:155-166, 2004.
Bustin, *J. Mol. Endocrinol.*, 29(1):23-39, 2002.
Cardullo et al., *Proc. Natl. Acad. Sci. USA*, 85:8790-8804, 1988.
Chen et al, *J. Virol. Methods*, 122(1):57-61, 2004.
Dorak, In: *Real-time PCR*, Bios Advanced Methods, 1$^{st}$ Ed., Taylor & Francis, 2006.
Egholm et al., *Nature*, 365(6446):566-568, 1993.
Espy et al, *Clin. Microbiol. Rev.*, 19(1):165-256, 2006.
Guo et al., *Nat. Biotechnol.*, 4:331-335, 1997.
Higuchi et al., *Biotechnol.*, 10:412-417, 1992.
Higuchi et al., *Biotechnol.*, 11:1026-1030, 1993.
Ishiguro et al, *Anal Biochemistry*, 229(2): 207-213, 1995.
Johnson et al, *Nucl. Acids Res.*, 32:1937-1941, 2004.
Koshkin and Dunford, *J. Biol. Chem.*, 273(11):6046-6049, 1998a.
Koshkin and Wengel, *J. Org. Chem.*, 63(8):2778-2781, 1998b.
Lay and Wittwer, *Clin. Chem.*, 1997; 43: 2262-2267, 1997.
Morrison et al., *Anal. Biochem.*, 183:231-244, 1989.
Morrison et al., *Biochemistry*, 32:3095-3104, 1993.
Moser et al, *Nucl. Acids Res.*, 31:5048-5053, 2003.
Mueller et al., *Current Protocols in Mol. Biol.*; 15:5, 1993.
Nazarenko et al., *Nucleic Acids Res.*, 25(12):2516-2521, 1997.
Nazarenko et al., *Nucleic Acids Res.*, 30(9):37, 2002.
Nygren et al, *Biopolymers*, 46:39-51, 1998.
PCT Appln. PCT/EP/01219
PCT Appln. WO 92/20702
PCT Appln. WO 93/17126
PCT Appln. WO 9731256
Sano, T. et al., *Science*, 258:120-122, 1992.
Santalucia et al., *Biochemistry*; 38:3468-3477, 1999.
Sherrill et al., *J. Am. Chem. Soc.*, 126:4550-4556, 2004.
Sims, P W et al, *Anal Biochem.* 281:230-232, 2000.
Wahlestedt et al., *Proc. Natl. Acad. Sci. USA*, 97(10):5633-5638, 2000.
Whitcombe et al., *Nat. Biotechnol.*, 17:804-807, 1999.
Wilhelm and Pingoud, *Chem. BioChem*, 4:1120-1128, 2003.
Wittwer et al., *Biotechniques*, 22:130-138, 1997.
Zipper et al., *Nucleic Acids Res.*, 32(12):103, 2004.

What is claimed is:

1. A method of amplifying and detecting a plurality of nucleic acid targets in a sample comprising:
    (a) combining in a chamber a sample comprising the plurality of nucleic acid targets, a plurality of primer pairs for priming amplification of the plurality of nucleic acid targets, a labeling agent, and a first plurality of probes complementary to the plurality of nucleic acid targets, wherein the probes are immobilized on a plurality of encoded magnetic beads such that the identity of each probe is known from the encoded magnetic bead on which it is immobilized;
    (b) performing an amplification cycle to form labeled amplification products for each of the plurality of nucleic acid targets amplified with the plurality of primer pairs;
    (c) hybridizing the labeled amplification products to the probes immobilized on the encoded magnetic beads;
    (d) applying a magnetic field to a surface of the chamber to draw the encoded magnetic beads and the labeled amplification products hybridized to the probes immobilized on the encoded magnetic beads to the surface of the chamber;
    (e) detecting a signal from the encoded magnetic beads and a signal from the labeled amplification products;
    (f) removing the magnetic field from the surface of the chamber prior to performing a further amplification cycle; and
    (g) repeating steps (b) through (f) at least once;
wherein the plurality of nucleic acid targets in the sample are amplified and detected.

2. The method of claim 1, further comprising correlating the signal from the labeled amplification product with the concentration of the nucleic acid target in the sample.

3. The method of claim 1, wherein the plurality of primer pairs is further defined as between 8 to 500 distinct primer pairs.

4. The method of claim 1, wherein the labeling agent is attached to one primer of each of the primer pairs.

5. The method of claim 1, wherein the chamber is a quartz chamber.

6. The method of claim 1, wherein the labeling agent is a fluorescent dye.

7. The method of claim 1, wherein the labeling agent is a fluorescence resonance energy transfer pair.

8. The method of claim 1, further comprising combining in the chamber a second plurality of probes complementary to the plurality of nucleic acid targets, wherein the second plurality of probes are not immobilized on the plurality of encoded magnetic beads and further wherein the second plurality of probes are complementary to different regions on the plurality of nucleic acid targets than the first plurality of probes.

9. The method of claim 8, wherein one member of a fluorescence resonance energy transfer pair is attached to the first plurality of probes immobilized on the encoded magnetic beads and the other member of the fluorescence resonance energy transfer pair is attached to the second plurality of probes that are not immobilized on the encoded magnetic beads.

10. The method of claim 1, wherein the labeling agent is a fluorophore and quencher pair.

11. The method of claim 1, wherein the labeling agent is a DNA intercalating agent.

12. The method of claim 1, wherein the encoded magnetic beads are encoded with fluorescent dyes.

13. The method of claim 12, wherein the encoded magnetic beads are encoded with different fluorescent intensities.

14. The method of claim 12, wherein the encoded magnetic beads are encoded with different fluorescent emission wavelengths.

15. The method of claim 1, wherein the encoded magnetic beads are superparamagnetic.

16. The method of claim 1, wherein applying the magnetic field comprises placing a permanent magnet adjacent to the surface of the chamber.

17. The method of claim 1, wherein applying the magnetic field comprises turning on an electromagnet adjacent to the surface of the chamber.

18. The method of claim 1, wherein the magnetic field is applied during a primer annealing phase of the amplification cycle.

19. The method of claim 1, wherein the magnetic field is applied during a primer extension phase of the amplification cycle.

20. The method of claim 1, wherein the magnetic field is applied following the amplification cycle.

21. The method of claim 1, wherein detecting the encoded magnetic beads and the labeled amplification products comprises imaging fluorescent wavelengths emitted from the encoded magnetic beads and the labeled amplification products.

22. The method of claim 1, wherein removing the magnetic field comprises removing a permanent magnet from a position adjacent to the surface of the chamber.

23. The method of claim 1, wherein removing the magnetic field comprises turning off an electromagnet adjacent to the surface of the chamber.

24. The method of claim 1, wherein steps (b) through (f) are repeated between 10 to 40 times.

25. The method of claim 1, wherein the plurality of probes comprise a blocked 3' hydroxyl group.

26. The method of claim 25, wherein the 3' hydroxyl group is blocked with a phosphate group.

27. The method of claim 25, wherein the 3' hydroxyl group is blocked with a 3' inverted dT.

28. A method of amplifying and detecting a plurality of nucleic acid targets in a sample comprising:
    (a) combining in a chamber a sample comprising the plurality of nucleic acid targets, a plurality of primer pairs for priming amplification of the plurality of nucleic acid targets, and a plurality of molecular beacons complementary to the plurality of nucleic acid targets, wherein the molecular beacons are immobilized on a plurality of encoded magnetic beads such that the identity of each molecular beacon is known from the encoded magnetic bead on which it is immobilized;
    (b) performing an amplification cycle to form amplification products for each of the plurality of nucleic acid targets amplified with the plurality of primer pairs;
    (c) hybridizing the amplification products to the molecular beacons immobilized on the encoded magnetic beads;
    (d) applying a magnetic field to a surface of the chamber to draw the encoded magnetic beads and the amplification products hybridized to the molecular beacons immobilized on the encoded magnetic beads to the surface of the chamber;
    (e) detecting a signal from the encoded magnetic beads and a signal from the molecular beacons;
    (f) removing the magnetic field from the surface of the chamber prior to performing a further amplification cycle; and
    (g) repeating steps (b) through (f) at least once;
wherein the plurality of nucleic acid targets in the sample are amplified and detected.

29. A method of amplifying and detecting a nucleic acid target in a sample comprising:
    (a) combining in a chamber a sample comprising the nucleic acid target, a primer pair for priming amplification of the nucleic acid target, and a probe set complementary to the nucleic acid target, wherein the probe set comprises a first probe immobilized on a magnetic bead, and a second probe comprising a label;
    (b) performing an amplification cycle to form amplification products for the nucleic acid target amplified with the primer pair;
    (c) hybridizing the amplification products to the probe set;
    (d) applying a magnetic field to a surface of the chamber to draw the magnetic bead and the amplification products hybridized to the probe immobilized on the encoded magnetic bead to the surface of the chamber;
    (e) detecting a signal from the second probe hybridized to the amplification products;
    (f) removing the magnetic field from the surface of the chamber prior to performing a further amplification cycle; and
    (g) repeating steps (b) through (f) at least once;
wherein the nucleic acid target in the sample is amplified and detected.

30. The method of claim 29, wherein the magnetic bead is an encoded magnetic bead.

31. The method of claim 29, further defined as a method of amplifying and detecting a plurality of nucleic acid targets comprising:

(a) combining in the chamber a sample comprising a plurality of nucleic acid targets, a plurality of primer pairs for priming amplification of the plurality of nucleic acid targets, and a plurality of probe sets complementary to the plurality of nucleic acid targets, wherein each probe set comprises a first probe immobilized on an encoded magnetic bead such that the identity of the first probe is known from the encoded magnetic bead on which it is immobilized, and a second probe comprising a label;

(b) performing an amplification cycle to form amplification products for each of the plurality of nucleic acid targets amplified with the plurality of primer pairs;

(c) hybridizing the amplification products to the probe sets;

(d) applying a magnetic field to a surface of the chamber to draw the encoded magnetic beads and the amplification products hybridized to the probes immobilized on the encoded magnetic beads to the surface of the chamber;

(e) detecting a signal from the encoded magnetic beads and a signal from the second probe hybridized to the amplification products;

(f) removing the magnetic field from the surface of the chamber prior to performing a further amplification cycle; and (g) repeating steps (b) through (f) at least once;

wherein the plurality of nucleic acid targets in the sample are amplified and detected.

32. A method of amplifying and detecting a nucleic acid target in a sample comprising:

(a) combining in a chamber a sample comprising the nucleic acid target, a primer pair for priming amplification of the nucleic acid target, a dNTP coupled to a quencher molecule, and a fluorescently labeled probe complementary to the nucleic acid target, wherein the probe is immobilized on a magnetic beads;

(b) performing an amplification cycle to form amplification products of the nucleic acid target, the amplification products comprising quencher molecules;

(c) hybridizing the amplification products to the probe immobilized on the magnetic bead;

(d) applying a magnetic field to a surface of the chamber to draw the magnetic bead and the amplification products hybridized to the probe immobilized on the encoded magnetic bead to the surface of the chamber;

(e) detecting a signal from the labeled probe, wherein a decrease in the signal from the labeled probe indicates hybridization of the labeled probe to the amplification products comprising quencher molecules;

(f) removing the magnetic field from the surface of the chamber prior to performing a further amplification cycle; and (g) repeating steps (b) through (f) at least once;

wherein the nucleic acid target in the sample is amplified and detected.

33. The method of claim 32, wherein the magnetic bead is an encoded magnetic bead.

34. The method of claim 32, further defined as a method of amplifying and detecting a plurality of nucleic acid targets comprising:

(a) combining in the chamber a sample comprising the plurality of nucleic acid targets, a plurality of primer pairs for priming amplification of the plurality of nucleic acid targets, a dNTP coupled to a quencher molecule, and a plurality of fluorescently labeled probes complementary to the plurality of nucleic acid targets, wherein the probes are immobilized on a plurality of encoded magnetic beads such that the identity of each probe is known from the encoded magnetic bead on which it is immobilized;

(b) performing an amplification cycle to form amplification products comprising quencher molecules for each of the plurality of nucleic acid targets amplified with the plurality of primer pairs;

(c) hybridizing the amplification products to the probes immobilized on the encoded magnetic beads;

(d) applying a magnetic field to a surface of the chamber to draw the encoded magnetic beads and the amplification products hybridized to the probes immobilized on the encoded magnetic beads to the surface of the chamber;

(e) detecting a signal from the encoded magnetic beads and a signal from the labeled probes, wherein a decrease in the signal from the labeled probes indicates hybridization of the labeled probes to the amplification products comprising quencher molecules;

(f) removing the magnetic field from the surface of the chamber prior to performing a further amplification cycle; and (g) repeating steps (b) through (f) at least once;

wherein the plurality of nucleic acid targets in the sample are amplified and detected.

35. A method of amplifying and detecting a plurality of nucleic acid targets in a sample comprising:

(a) combining in a chamber a sample comprising the plurality of nucleic acid targets; a plurality of primer pairs for priming amplification of the plurality of nucleic acid targets, wherein each primer pair comprises a first primer comprising a target specific sequence, a tag sequence 5' of the target specific sequence, and a blocker between the target specific sequence and the tag sequence, and a second primer comprising a target specific sequence; a labeling agent; and a plurality of probes complementary to the tag sequences of the plurality of primer pairs, wherein the probes are immobilized on a plurality of encoded magnetic beads such that the identity of each probe is known from the encoded magnetic bead on which it is immobilized;

(b) performing an amplification cycle to form tagged and labeled amplification products for each of the plurality of nucleic acid targets amplified with the plurality of primer pairs;

(c) hybridizing the tagged and labeled amplification products to the probes immobilized on the encoded magnetic beads;

(d) applying a magnetic field to a surface of the chamber to draw the encoded magnetic beads and the tagged and labeled amplification products hybridized to the probes immobilized on the encoded magnetic beads to the surface of the chamber;

(e) detecting the encoded magnetic beads and the tagged and labeled amplification products;

(f) removing the magnetic field from the surface of the chamber prior to performing a further amplification cycle; and (g) repeating steps (b) through (f) at least once;

wherein the plurality of nucleic acid targets in the sample are amplified and detected.

36. The method of claim 35, wherein the labeling agent is a reporter molecule attached to the second primer of the primer pair.

37. The method of claim 35, wherein the labeling agent is an intercalating dye.

* * * * *

SEQUENCE LISTING

<160> NUMBER OF SEQ ID NOS: 50

<210> SEQ ID NO 1
<211> LENGTH: 25
<212> TYPE: DNA
<213> ORGANISM: Artificial
<220> FEATURE:
<223> OTHER INFORMATION: Artificial primer

```
<400> SEQUENCE: 1
tgttatcaca ctggtgctaa aaagg                                         25

<210> SEQ ID NO 2
<211> LENGTH: 15
<212> TYPE: DNA
<213> ORGANISM: Artificial
<220> FEATURE:
<223> OTHER INFORMATION: Artificial primer

<400> SEQUENCE: 2
actacagtga cgtgg                                                    15

<210> SEQ ID NO 3
<211> LENGTH: 31
<212> TYPE: DNA
<213> ORGANISM: Artificial
<220> FEATURE:
<223> OTHER INFORMATION: Artificial primer

<400> SEQUENCE: 3
ataatggggc atttccttca agagaacagt a                                  31

<210> SEQ ID NO 4
<211> LENGTH: 30
<212> TYPE: DNA
<213> ORGANISM: Artificial
<220> FEATURE:
<223> OTHER INFORMATION: Artificial primer

<400> SEQUENCE: 4
tctggctaga acatgttagg tctcctggct                                    30

<210> SEQ ID NO 5
<211> LENGTH: 24
<212> TYPE: DNA
<213> ORGANISM: Artificial
<220> FEATURE:
<223> OTHER INFORMATION: Artificial primer

<400> SEQUENCE: 5
aaagaaagga tttgtagtaa gatt                                          24

<210> SEQ ID NO 6
<211> LENGTH: 300
<212> TYPE: DNA
<213> ORGANISM: Homo sapiens

<400> SEQUENCE: 6
cacagaaaat gatgcccagt gcttaacaag accatactac agtgacgtgg acatcatgag    60
agacatcgcc tctgggctaa taggactact tctaatctgt aagagcagat ccctggacag   120
gcgaggaata caggtatttt gtccttgaag taacctttca gaaattctga gaatttcttc   180
tggctagaac atgttaggtc tcctggctaa ataatggggc atttccttca agagaacagt   240
aattgtcaag tagtcctttt tagcaccagt gtgataacat ttattctttt ttttttttg    300

<210> SEQ ID NO 7
<211> LENGTH: 300
<212> TYPE: DNA
<213> ORGANISM: Homo sapiens

<400> SEQUENCE: 7
gtgtctttta ctacgggtca cgaattgttc tggtatgatg tcactgcacc tgtagtactc    60
```

```
tctgtagcgg agacccgatt atcctgatga agattagaca ttctcgtcta gggacctgtc    120
cgctccttat gtccataaaa caggaacttc attggaaagt ctttaagact cttaaagaag    180
accgatcttg tacaatccag aggaccgatt tattacccccg taaaggaagt tctcttgtca    240
ttaacagttc atcaggaaaa atcgtggtca cactattgta aataagaaaa aaaaaaaaac    300
```

<210> SEQ ID NO 8
<211> LENGTH: 145
<212> TYPE: DNA
<213> ORGANISM: Homo sapiens

<400> SEQUENCE: 8

```
cagctttttt gagactactg aacactgaag gagaaatcca gatcgatggt gtgtcttggg     60
attcaataac tttgcaacag tggaggaaag cctttggagt gataccacag gtgagcaaaa    120
ggacttagcc agaaaaaagg caact                                          145
```

<210> SEQ ID NO 9
<211> LENGTH: 114
<212> TYPE: DNA
<213> ORGANISM: Homo sapiens

<400> SEQUENCE: 9

```
tcaaattcag attgagcata ctaaaagtga ctctctaatt ttctattttt ggtaatagga     60
catctccaag tttgcagaga aagacaatat agttcttgga aaggtggaa tcac           114
```

<210> SEQ ID NO 10
<211> LENGTH: 149
<212> TYPE: DNA
<213> ORGANISM: Homo sapiens

<400> SEQUENCE: 10

```
atctccaagt ttgcagagaa agacaatata gttcttggag aaggtggaat cacactgagt     60
ggaggtcaac gagcaagaat ttctttagca aggtgaataa ctaattattg gtctagcaag    120
catttgctgt aaatgtcatt catgtaaaa                                      149
```

<210> SEQ ID NO 11
<211> LENGTH: 160
<212> TYPE: DNA
<213> ORGANISM: Homo sapiens

<400> SEQUENCE: 11

```
tccccttttg taggaagtca ccaaagcagt acagcctctc ttactgggaa gaatcatagc     60
ttcctatgac ccggataaca aggaggaacg ctctatcgcg atttatctag cataggctt     120 atgccttctc tttattgtga ggacactgct cctacaccca                          160
```

<210> SEQ ID NO 12
<211> LENGTH: 118
<212> TYPE: DNA
<213> ORGANISM: Homo sapiens

<400> SEQUENCE: 12

```
ttttttgcta tagaaagtat ttattttttc tggaacattt agaaaaaact tggatcccta     60
tgaacagtgg agtgatcaag aaatatggaa agttgcagat gaggtaaggc tgctaact      118
```

<210> SEQ ID NO 13
<211> LENGTH: 165
<212> TYPE: DNA
<213> ORGANISM: Homo sapiens

<400> SEQUENCE: 13
ttttatagaa cagaactgaa actgactcgg aaggcagcct atgtgagata cttcaatagc      60
tcagccttct tcttctcagg gttctttgtg gtgtttttat ctgtgcttcc ctatgcacta     120
atcaaaggaa tcatcctccg gaaaatattc accaccatct cattc                    165

<210> SEQ ID NO 14
<211> LENGTH: 169
<212> TYPE: DNA
<213> ORGANISM: Homo sapiens

<400> SEQUENCE: 14
aatttcagtt gacttgtcat cttgatttct ggagaccaca aggtaatgaa aataattac      60 aagagtcttc catctgttgc agtattaaaa tggcgagtaa gacaccctga aaggaaatgt    120
tctattcatg gtacaatgca attacagcta gcaccaaatt caacactgt                169

<210> SEQ ID NO 15
<211> LENGTH: 123
<212> TYPE: DNA
<213> ORGANISM: Homo sapiens

<400> SEQUENCE: 15
taatttctca cttcttggta ctcctgtcct gaaagatatt aatttcaaga tagaaagagg      60
acagttgttg gcggttgctg gatccactgg agcaggcaag gtagttcttt tgttcttcac    120
tat                                                                   123

<210> SEQ ID NO 16
<211> LENGTH: 46
<212> TYPE: DNA
<213> ORGANISM: Artificial
<220> FEATURE:
<223> OTHER INFORMATION: Artificial primer

<400> SEQUENCE: 16
caaacaaaca ttcaaatatc aatccaagga ggagctgctg aagatg                    46

<210> SEQ ID NO 17
<211> LENGTH: 23
<212> TYPE: DNA
<213> ORGANISM: Artificial
<220> FEATURE:
<223> OTHER INFORMATION: Artificial primer

<400> SEQUENCE: 17
cactttgtga ccattccggt ttg                                             23

<210> SEQ ID NO 18
<211> LENGTH: 24
<212> TYPE: DNA
<213> ORGANISM: Artificial
<220> FEATURE:
<223> OTHER INFORMATION: Artificial primer

<400> SEQUENCE: 18
gattgatatt tgaatgtttg tttg                                            24

<210> SEQ ID NO 19
<211> LENGTH: 18
<212> TYPE: DNA
<213> ORGANISM: Artificial
<220> FEATURE:
<223> OTHER INFORMATION: Artificial primer

<400> SEQUENCE: 19
caacagtgga ggaaagcc                                                    18

<210> SEQ ID NO 20
<211> LENGTH: 180
<212> TYPE: DNA
<213> ORGANISM: Homo sapiens

<400> SEQUENCE: 20
ggaggagctg ctgaagatgt gggggagga gctcaccagt gaagaaagtg tctttgaagt        60
ctttgttctt cctcctcgac gacttctaca ccccccctcct cgagtggtca cttctttcac    120
agaaacttca gaaacaagaa tacctctcgg gagaaccaaa ccggaatggt cacaaagtga    180

<210> SEQ ID NO 21
<211> LENGTH: 23
<212> TYPE: DNA
<213> ORGANISM: Artificial
<220> FEATURE:
<223> OTHER INFORMATION: Artificial primer

<400> SEQUENCE: 21
ttgagactac tgaacactga agg                                              23

<210> SEQ ID NO 22
<211> LENGTH: 20
<212> TYPE: DNA
<213> ORGANISM: Artificial
<220> FEATURE:
<223> OTHER INFORMATION: Artificial primer

<400> SEQUENCE: 22
ttctggctaa gtccttttgc                                                  20

<210> SEQ ID NO 23
<211> LENGTH: 25
<212> TYPE: DNA
<213> ORGANISM: Artificial
<220> FEATURE:
<223> OTHER INFORMATION: Artificial primer

<400> SEQUENCE: 23
tcagattgag catactaaaa gtgac                                            25

<210> SEQ ID NO 24
<211> LENGTH: 26
<212> TYPE: DNA
<213> ORGANISM: Artificial
<220> FEATURE:
<223> OTHER INFORMATION: Artificial primer

<400> SEQUENCE: 24
gaactatatt gtctttctct gcaaac                                           26

<210> SEQ ID NO 25
<211> LENGTH: 25
<212> TYPE: DNA
<213> ORGANISM: Artificial
<220> FEATURE:
<223> OTHER INFORMATION: Artificial primer

<400> SEQUENCE: 25
aagtttgcag agaaagacaa tatag                                            25

```
<210> SEQ ID NO 26
<211> LENGTH: 22
<212> TYPE: DNA
<213> ORGANISM: Artificial
<220> FEATURE:
<223> OTHER INFORMATION: Artificial primer

<400> SEQUENCE: 26
gaatgacatt tacagcaaat gc                                               22

<210> SEQ ID NO 27
<211> LENGTH: 21
<212> TYPE: DNA
<213> ORGANISM: Artificial
<220> FEATURE:
<223> OTHER INFORMATION: Artificial primer

<400> SEQUENCE: 27
tttgtaggaa gtcaccaaag c                                                21

<210> SEQ ID NO 28
<211> LENGTH: 24
<212> TYPE: DNA
<213> ORGANISM: Artificial
<220> FEATURE:
<223> OTHER INFORMATION: Artificial primer

<400> SEQUENCE: 28
gagcagtgtc ctcacaataa agag                                             24

<210> SEQ ID NO 29
<211> LENGTH: 28
<212> TYPE: DNA
<213> ORGANISM: Artificial
<220> FEATURE:
<223> OTHER INFORMATION: Artificial primer

<400> SEQUENCE: 29
tgctatagaa agtatttatt ttttctgg                                         28

<210> SEQ ID NO 30
<211> LENGTH: 20
<212> TYPE: DNA
<213> ORGANISM: Artificial
<220> FEATURE:
<223> OTHER INFORMATION: Artificial primer

<400> SEQUENCE: 30
agccttacct catctgcaac                                                  20

<210> SEQ ID NO 31
<211> LENGTH: 22
<212> TYPE: DNA
<213> ORGANISM: Artificial
<220> FEATURE:
<223> OTHER INFORMATION: Artificial primer

<400> SEQUENCE: 31
gaacagaact gaaactgact cg                                               22

<210> SEQ ID NO 32
<211> LENGTH: 18
<212> TYPE: DNA
<213> ORGANISM: Artificial
<220> FEATURE:
<223> OTHER INFORMATION: Artificial primer

<400> SEQUENCE: 32
```

-continued cagggaaatt gccgagtg                                             18

<210> SEQ ID NO 33
<211> LENGTH: 22
<212> TYPE: DNA
<213> ORGANISM: Artificial
<220> FEATURE:
<223> OTHER INFORMATION: Artificial primer

<400> SEQUENCE: 33
gacttgtcat cttgatttct gg                                        22

<210> SEQ ID NO 34
<211> LENGTH: 21
<212> TYPE: DNA
<213> ORGANISM: Artificial
<220> FEATURE:
<223> OTHER INFORMATION: Artificial primer

<400> SEQUENCE: 34
tttggtgcta gctgtaattg c                                         21

<210> SEQ ID NO 35
<211> LENGTH: 22
<212> TYPE: DNA
<213> ORGANISM: Artificial
<220> FEATURE:
<223> OTHER INFORMATION: Artificial primer

<400> SEQUENCE: 35
tcacttcttg gtactcctgt cc                                        22

<210> SEQ ID NO 36
<211> LENGTH: 21
<212> TYPE: DNA
<213> ORGANISM: Artificial
<220> FEATURE:
<223> OTHER INFORMATION: Artificial primer

<400> SEQUENCE: 36
caaaagaact accttgcctg c                                         21

<210> SEQ ID NO 37
<211> LENGTH: 18
<212> TYPE: DNA
<213> ORGANISM: Artificial
<220> FEATURE:
<223> OTHER INFORMATION: Artificial primer

<400> SEQUENCE: 37
caacagtgga ggaaagcc                                             18

<210> SEQ ID NO 38
<211> LENGTH: 20
<212> TYPE: DNA
<213> ORGANISM: Artificial
<220> FEATURE:
<223> OTHER INFORMATION: Artificial primer

<400> SEQUENCE: 38
ttggtaatag gacatctcca                                           20

<210> SEQ ID NO 39
<211> LENGTH: 20
<212> TYPE: DNA
<213> ORGANISM: Artificial

```
<220> FEATURE:
<223> OTHER INFORMATION: Artificial primer

<400> SEQUENCE: 39
ctttagcaag gtgataact                                          20

<210> SEQ ID NO 40
<211> LENGTH: 20
<212> TYPE: DNA
<213> ORGANISM: Artificial
<220> FEATURE:
<223> OTHER INFORMATION: Artificial primer

<400> SEQUENCE: 40
aggaggaacg ctctatcgcg                                         20

<210> SEQ ID NO 41
<211> LENGTH: 20
<212> TYPE: DNA
<213> ORGANISM: Artificial
<220> FEATURE:
<223> OTHER INFORMATION: Artificial primer

<400> SEQUENCE: 41
gggatccaag tttttctaa                                          20

<210> SEQ ID NO 42
<211> LENGTH: 18
<212> TYPE: DNA
<213> ORGANISM: Artificial
<220> FEATURE:
<223> OTHER INFORMATION: Artificial primer

<400> SEQUENCE: 42
caccacaaag aaccctga                                           18

<210> SEQ ID NO 43
<211> LENGTH: 20
<212> TYPE: DNA
<213> ORGANISM: Artificial
<220> FEATURE:
<223> OTHER INFORMATION: Artificial primer

<400> SEQUENCE: 43
ccagcaaccg ccaacaactg                                         20

<210> SEQ ID NO 44
<211> LENGTH: 18
<212> TYPE: DNA
<213> ORGANISM: Artificial
<220> FEATURE:
<223> OTHER INFORMATION: Artificial primer

<400> SEQUENCE: 44
ttgacttggt aggtttac                                           18

<210> SEQ ID NO 45
<211> LENGTH: 22
<212> TYPE: DNA
<213> ORGANISM: Artificial
<220> FEATURE:
<223> OTHER INFORMATION: Artificial primer

<400> SEQUENCE: 45
tggaaagtga gtattccatg tc                                      22
```

```
<210> SEQ ID NO 46
<211> LENGTH: 17
<212> TYPE: DNA
<213> ORGANISM: Artificial
<220> FEATURE:
<223> OTHER INFORMATION: Artificial primer

<400> SEQUENCE: 46
gaaacaaaaa aacaatc                                                      17

<210> SEQ ID NO 47
<211> LENGTH: 22
<212> TYPE: DNA
<213> ORGANISM: Artificial
<220> FEATURE:
<223> OTHER INFORMATION: Artificial primer

<400> SEQUENCE: 47
tatttgaaag gtatgttctt tg                                                22

<210> SEQ ID NO 48
<211> LENGTH: 22
<212> TYPE: DNA
<213> ORGANISM: Artificial
<220> FEATURE:
<223> OTHER INFORMATION: Artificial primer

<400> SEQUENCE: 48
cttcatccag gtatgtaaaa at                                                22

<210> SEQ ID NO 49
<211> LENGTH: 22
<212> TYPE: DNA
<213> ORGANISM: Artificial
<220> FEATURE:
<223> OTHER INFORMATION: Artificial primer

<400> SEQUENCE: 49
atttgatgaa gtatgtacct at                                                22

<210> SEQ ID NO 50
<211> LENGTH: 20
<212> TYPE: DNA
<213> ORGANISM: Artificial
<220> FEATURE:
<223> OTHER INFORMATION: Artificial primer

<400> SEQUENCE: 50
gtcttactcg ccattttaat                                                   20
```